US012653689B2

(12) United States Patent
Messerli

(10) Patent No.: US 12,653,689 B2
(45) Date of Patent: Jun. 16, 2026

(54) FLEXIBLE SPINAL IMPLANT FOR SUPPORTING VERTEBRAL STRUCTURES

(71) Applicant: Lenoss Medical, Inc., Bristol, RI (US)

(72) Inventor: Dom Messerli, Bristol, RI (US)

(73) Assignee: Lenoss Medical, Inc., Bristol, RI (US)

( * ) Notice: Subject to any disclaimer, the term of this patent is extended or adjusted under 35 U.S.C. 154(b) by 0 days.

(21) Appl. No.: 19/349,605

(22) Filed: Oct. 3, 2025

(65) Prior Publication Data

US 2026/0096900 A1 Apr. 9, 2026

Related U.S. Application Data

(63) Continuation of application No. PCT/US2024/040965, filed on Aug. 5, 2024.

(60) Provisional application No. 63/530,926, filed on Aug. 4, 2023.

(51) Int. Cl.
*A61F 2/44* (2006.01)
*A61F 2/30* (2006.01)

(52) U.S. Cl.
CPC ...... *A61F 2/44* (2013.01); *A61F 2002/30242* (2013.01); *A61F 2002/30327* (2013.01); *A61F 2002/30518* (2013.01); *A61F 2002/4415* (2013.01)

(58) Field of Classification Search
None
See application file for complete search history.

(56) References Cited

U.S. PATENT DOCUMENTS

| | | | |
|---|---|---|---|
| 2,556,783 A | 6/1951 | Wallace | |
| 2,649,092 A | 8/1953 | Wallace | |
| 3,517,128 A | 6/1970 | Hines | |
| 3,713,447 A | 1/1973 | Adair | |
| 3,799,172 A | 3/1974 | Szpur | |
| 4,611,581 A | 9/1986 | Steffee | |
| 4,808,163 A | 2/1989 | Laub | |
| 5,275,610 A | 1/1994 | Ederbach | |
| 5,370,611 A | 12/1994 | Niezink et al. | |
| 5,370,661 A | 12/1994 | Branch | |

(Continued)

FOREIGN PATENT DOCUMENTS

| | | |
|---|---|---|
| CN | 307934558 S | 3/2023 |
| EP | 0621020 A1 | 10/1994 |

(Continued)

OTHER PUBLICATIONS

[No Author Listed] "Spider Kyphoplasty and Vertebroplasty System", Sintea-Plustek, Jul. 20, 2011, 2 pages.

(Continued)

*Primary Examiner* — Eduardo C Robert
*Assistant Examiner* — Christina Negrellirodriguez
(74) *Attorney, Agent, or Firm* — Fish & Richardson P.C.

(57) ABSTRACT

A spinal implant device includes a unitary strand extending from a first end to a second end. The unitary strand includes an exterior surface defining an infill volume with an infill structure. The exterior surface extends from the first end to the second end. A first bead is formed in the strand has a first diameter. The second bead is formed in the strand has a second diameter. At least one joint is formed in the strand between the first bead and the second bead. The at least one joint has a third diameter that is less than the first diameter and less than the second diameter.

22 Claims, 47 Drawing Sheets

(56) References Cited

U.S. PATENT DOCUMENTS

| | | | |
|---|---|---|---|
| 5,454,365 A | 10/1995 | Bonutti | |
| 5,554,101 A | 9/1996 | Matula et al. | |
| 5,678,572 A | 10/1997 | Shaw et al. | |
| 5,690,678 A | 11/1997 | Johnson | |
| 5,702,454 A | 12/1997 | Baumgartner | |
| 5,756,127 A | 5/1998 | Grisoni et al. | |
| 5,782,831 A | 7/1998 | Sherman et al. | |
| 5,878,886 A | 3/1999 | Marshall | |
| 6,235,043 B1 | 5/2001 | Reiley et al. | |
| 6,248,110 B1 | 6/2001 | Reiley et al. | |
| 6,277,120 B1 | 8/2001 | Lawson | |
| 6,325,802 B1 | 12/2001 | Frigg | |
| 6,423,083 B2 | 7/2002 | Reiley et al. | |
| 6,491,714 B1 | 12/2002 | Bennett | |
| 6,676,665 B2 | 1/2004 | Foley et al. | |
| 6,679,886 B2 | 1/2004 | Weikel et al. | |
| 6,849,080 B2 | 2/2005 | Lee et al. | |
| 7,044,954 B2 | 5/2006 | Reiley et al. | |
| 7,114,501 B2 | 10/2006 | Johnson et al. | |
| 7,351,262 B2 | 4/2008 | Bindseil et al. | |
| 7,641,664 B2 | 1/2010 | Pagano | |
| 7,722,612 B2 | 5/2010 | Sala et al. | |
| 7,771,458 B2 | 8/2010 | Biedermann et al. | |
| 7,815,643 B2 | 10/2010 | Johnson et al. | |
| 8,118,874 B2 | 2/2012 | Vresilovic et al. | |
| 8,353,911 B2 | 1/2013 | Goldin | |
| 8,486,082 B2 | 7/2013 | Geisert | |
| D697,209 S | 1/2014 | Walthall et al. | |
| 8,673,010 B2 | 3/2014 | Compton et al. | |
| 9,289,240 B2 | 3/2016 | Messerli | |
| 10,219,851 B1 | 3/2019 | Messerli | |
| 10,307,188 B2 | 6/2019 | Harshman et al. | |
| 10,881,520 B2 | 1/2021 | Messerli | |
| 10,993,756 B2 | 5/2021 | Messerli | |
| 11,406,508 B2 | 8/2022 | Messerli | |
| 12,029,463 B2 | 7/2024 | Messerli | |
| 2002/0026197 A1 | 2/2002 | Foley et al. | |
| 2002/0068974 A1 | 6/2002 | Kuslich et al. | |
| 2002/0143328 A1 | 10/2002 | Shluzas et al. | |
| 2002/0183752 A1 | 12/2002 | Steiner et al. | |
| 2003/0088249 A1 | 5/2003 | Furderer | |
| 2003/0187449 A1 | 10/2003 | McCleary et al. | |
| 2004/0059338 A1 | 3/2004 | Ebner | |
| 2004/0073308 A1 | 4/2004 | Kuslich et al. | |
| 2004/0078080 A1 | 4/2004 | Thramann et al. | |
| 2004/0097930 A1 | 5/2004 | Justis et al. | |
| 2004/0177847 A1 | 9/2004 | Foley et al. | |
| 2005/0070911 A1 | 3/2005 | Carrison et al. | |
| 2005/0113929 A1* | 5/2005 | Cragg | A61F 2/442 606/279 |
| 2005/0131548 A1 | 6/2005 | Boyer et al. | |
| 2005/0182417 A1 | 8/2005 | Pagano | |
| 2005/0209629 A1 | 9/2005 | Kerr et al. | |
| 2005/0278023 A1 | 12/2005 | Zwirkoski | |
| 2006/0089715 A1 | 4/2006 | Truckai et al. | |
| 2006/0095138 A1 | 5/2006 | Truckai et al. | |
| 2006/0100706 A1 | 5/2006 | Shadduck et al. | |
| 2006/0122625 A1 | 6/2006 | Truckai et al. | |
| 2006/0122650 A1 | 6/2006 | Truckai et al. | |
| 2007/0005140 A1* | 1/2007 | Kim | A61F 2/441 623/17.11 |
| 2007/0162132 A1 | 7/2007 | Messerli | |
| 2007/0208426 A1* | 9/2007 | Trieu | A61F 2/442 623/17.14 |
| 2008/0287951 A1 | 11/2008 | Stoneburner et al. | |
| 2008/0300636 A1 | 12/2008 | Carli et al. | |
| 2009/0005821 A1 | 1/2009 | Chirico et al. | |
| 2009/0319045 A1* | 12/2009 | Truncale | A61L 27/48 623/23.73 |
| 2010/0331842 A1 | 12/2010 | Milbank | |
| 2011/0144643 A1 | 6/2011 | Lorenz et al. | |
| 2014/0309636 A1 | 10/2014 | Meek et al. | |
| 2016/0015521 A1 | 1/2016 | Tornel et al. | |
| 2019/0290345 A1 | 9/2019 | Messerli | |
| 2022/0087728 A1 | 3/2022 | Messerli | |
| 2025/0064489 A1 | 2/2025 | Harshman et al. | |
| 2025/0073982 A1 | 3/2025 | Globerman et al. | |
| 2025/0099142 A1 | 3/2025 | Hestad | |
| 2025/0099149 A1 | 3/2025 | Vale et al. | |
| 2025/0099150 A1 | 3/2025 | Messerli | |
| 2025/0120800 A1 | 4/2025 | Sostek et al. | |
| 2025/0161054 A1 | 5/2025 | Hamzey et al. | |

FOREIGN PATENT DOCUMENTS

| | | | |
|---|---|---|---|
| EP | 1308134 S | 7/2003 | |
| EP | 2932926 A2 | 10/2015 | |
| JP | H 06154258 A | 6/1994 | |
| JP | 1130599 A | 11/2001 | |
| JP | D1139461 S | 3/2002 | |
| JP | 2003126108 A | 5/2003 | |
| WO | WO 2001/054598 A1 | 2/2001 | |
| WO | WO 2004/047689 A1 | 6/2004 | |
| WO | WO 2004/086934 A2 | 10/2004 | |
| WO | WO 2004/108019 A2 | 12/2004 | |
| WO | WO 2005/027734 A2 | 3/2005 | |
| WO | WO 2005/092248 A1 | 10/2005 | |
| WO | WO 2005/041796 A1 | 12/2005 | |
| WO | WO 2007/012070 A2 | 1/2007 | |

OTHER PUBLICATIONS

[No Author Listed] "Xvoid Cavity Creation System", Stryker, 1 page.

Amazon.com [online], "Excellerations Early STEM Toy, Connecting, Fun, Linking, Pop Beads for Toddlers, Snap Lock Beads Set in Storage Bin, Pack of 28," Dec. 2, 2011, retrieved on Mar. 5, 2025, retrieved from URL <https://www.amazon.com/Excellerations-Together-Toddlers-Preschoolers-FUNPOP/dp/B006H9FBOC?th=1>, 2 pages.

Angelinvestboston.com [online], "Dom Messerli on Angel Invest Boston," May 23, 2023, retrieved on Mar. 6, 2025, retrieved from URL <https://www.angelinvestboston.com/dom-messerli-treating-spinal-fractures-better>, 1 page.

Businesswire.com [online] "CurvaFix Receives FDA Clearance for Smaller-diameter, Indramedullary Implant for Pelvic Fracture Fixation," Nov. 1, 2022, retrieved on Mar. 6, 2025, retrieved from URL <https://www.businesswire.com/news/home/20221101005531/en/CurvaFix-Receives-FDA-Clearance-for-Smaller-diameter-Intramedullary-Implant-for-Pelvic-Fracture-Fixation>, 3 pages.

Curiteva.com [Online], "Inspire C," 2023, retrieved on Mar. 5, 2025, retrieved from URL <https://curiteva.com/inspirec/>, 3 pages.

Ebay.com [online], "Electronic Battleship Replacement Pieces," Jan. 2, 2025, retrieved on Jun. 4, 2025, retrieved from URL <https://www.ebay.com/itm/333089886209>, 2 pages.

Extended European Search Report in European Appln. No. 23177487.8, mailed on Jan. 30, 2024, 11 pages.

Fürderer et al., "Vertebral body stenting," Der Orthopäde. Apr. 2002, 31(4):356-61 (with English translation).

Gaitanis et al., "Balloon Kyphoplasty for the treatment of pathological vertebral compression fractures," Eur Spine Journal, Apr. 2005, 14(3):250-260.

International Preliminary Report on Patentability in International Appln. No. PCT/US2019/022862, mailed on Oct. 8, 2020, 9 pages.

International Search Report and Written Opinion in International Appln. No. PCT/US2019/022862, mailed on Jul. 2, 2019, 17 pages.

International Search Report and Written Opinion in International Appln. No. PCT/US2024/040965, mailed on Nov. 20, 2024, 19 pages.

Izimed.com [online], "Kiva VCF Treatment System," 2025 retrieved on Mar. 4, 2025, retrieved from URL <https://izimed.com/kiva>, 5 pages.

Jang et al., "Pulmonary embolism of polymethylmethacrylate after percutaneous vertebroplasty: a report of three cases," Spine, Oct. 2002, 27(19):E416-E418.

Kim et al., "Sunflower Kyphoplasty: A New Restoration Method for Vertebral Compression Fracture," Korean J Pain, Nov. 2004, 17(2):166-169 (with English abstract).

(56) References Cited

OTHER PUBLICATIONS

Lenoss.com [online], "Lenoss Medical OsteoPearl Overview," Apr. 11, 2022, retrieved on Mar. 6, 2025, retrieved from URL <https://lenoss.com/osteopearl-technology/>, 3 pages.

Lieberman et al., "Initial outcome and efficacy of kyphoplasty in the treatment of painful osteoporotic vertebral compression fractures," Spine, Jul. 15, 2001, 26(14):1631-1637.

Lifenethealth.org [online], "Oragraft," 2020, retrieved on Jun. 4, 2025, retrieved from URL <https://www.lifenethealth.org/sites/default/files/product-specification-pdf/ribs/68-65-031.pdf?>, 2 pages.

Magerl et al., "A comprehensive classification of thoracic and lumbar injuries," Eur Spine Journal, Aug. 1994, 3(4):184-201.

Office Action in Canadian Appln. No. 3,094,800, mailed on May 21, 2025, 4 pages.

Office Action in U.S. Appl. No. 12/068,799 mailed on Jan. 19, 2011, 10 pages.

*Orthophoenix LLC,* v. *Sintea Plustek LLC*; John and/or Jane Does 1-100, "Orthophoenix's Complaint for Patent Infringement," Case [Unassigned], filed on Jun. 4, 2013, 23 pages.

Poriferous.com [online], "Osteotomy Gap Filler," retrieved Jun. 4, 2025, retrieved from URL <https://poriferous.com/product/gap-filler/>, 2 pages.

Preliminary Amendment in US20080300636, dated Feb. 12, 2008, 7 pages.

Spineart.com [online], "Tektona Vertebral Fragment Reduction," retrieved on Mar. 31, 2025, retrieved from URL <http://spineart. com/product-platforms/trauma/7/product/tektona%C2%AE/689>, 1 page.

Todaysmedicaldevelopments.com [online], "Luna 360 Interbody Fusion System," Dec. 6, 2014, retrieved on Mar. 5, 2025, retrieved from URL <https://www.todaysmedicaldevelopments.com/news/medical-device-design-benvenue-fda-clearance-luna-12614/>, 2 pages.

Truumees, "Comparing kyphoplasty and vertebroplasty," Advances in Osteoporotic Fracture Management, 2002, 1(4):114-23.

Turnto10.com [online], "There's a new implant developed in Rhode Island to treat spine fractures," Feb. 23, 2022, retrieved on Mar. 7, 2025, retrieved from URL <https://turnto10.com/features/health-landing-page/theres-a-new-implant-developed-in-rhode-island-to-treat-spine-fractures-osteo-pearls-hea>, 4 pages.

Unicarebiomedical.com [online],"Revoss Matrix," retreived on Jun. 4, 2025, retrieved from URL <https://www.unicarebiomedical.com/pdf/revoss-matrix-flyer.pdf>, 1 page.

Vimeo.com [online], "Lenoss Medical OsteoPearl Overview," Apr. 11, 2022, retrieved Mar. 6, 2025, retrieved from URL <https://lenoss.com/osteopearl-technology/>, 2 pages.

Vimeo.com [online], "Pearl Intro and Insertion," Apr. 11, 2022, retrieved on Mar. 6, 2025, retrieved from URL <https://vimeo.com/698174873?autoplay=1 &muted=1&stream_id=Y2xpcHN8MTY4MjgxODAxfGlkOmRlc2N8eyJyZW1vdmVfdm9kX3RpdGxlyl6ZmFsc%E2%80%A6>, 2 pages.

International Preliminary Report on Patentability in International Appln. No. PCT/US2024/040965, mailed on Feb. 19, 2026, 11 pages.

* cited by examiner

200

```
┌─────────────────────────────────────┐
│ SOAKING A DEHYDRATED IMPLANT IN A   │
│ SOLUTION FOR LESS THAN 10 MINUTES TO│
│ FORM A PARTIALLY REHYDRATED IMPLANT │
└─────────────────────────────────────┘
                  │
                  ▼
┌─────────────────────────────────────┐
│ INSERTING THE PARTIALLY REHYDRATED  │
│ IMPLANT INTO A CAVITY OF A BONE TO  │
│ FORM A REHYDRATED IMPLANT           │
└─────────────────────────────────────┘
```

| EXTRUDING, BY A 3D PRINTER, A SHELL OF A FIRST PORTION OF THE FLEXIBLE SPINAL IMPLANT, THE SHELL FORMING AN EXTERIOR SURFACE OF THE IMPLANT, WHEREIN THE SHELL OF THE FIRST PORTION DEFINES A FIRST INTERNAL VOLUME |
|---|

↓

| INFILLING, BY THE 3D PRINTER, THE FIRST INTERNAL VOLUME OF THE FIRST PORTION OF THE IMPLANT WITH A BONE-LIKE INFILL PATTERN |
|---|

450

PRINTING INDIVIDUAL LINKS
WITH ATTACHMENT STRUCTURES
USING A 3D PRINTING SYSTEM

CONNECTING THE INDIVIDUAL LINKS
AT THE ATTACHMENT STRUCTURES
TO FORM A FOLDABLE CHAIN

INSERTING THE FOLDABLE
CHAIN INTO A BODY

710

FLEXIBLE SPINAL IMPLANT FOR SUPPORTING VERTEBRAL STRUCTURES

CROSS-REFERENCE TO RELATED APPLICATION

Pursuant to 35 U.S.C. § 119(e), this application is a continuation of International Application PCT/US2024/040965, with an international filing date of Aug. 5, 2024, which claims the benefit of U.S. Provisional Application Ser. No. 63/530,926, filed Aug. 4, 2023. The disclosure of the prior application is considered part of the disclosure of this application and is incorporated in its entirety into this application.

FIELD

This disclosure relates generally to surgical instrumentation and methods for supporting and expanding structures in the body such as, for example, surgical implants and methods for manufacturing and inserting implants into the body.

BACKGROUND

There are medical treatments that include transversely displacing and inserting implants to support damaged or collapsed structures in the body. For example, kyphoplasty is a procedure used to treat painful vertebral compression fractures in the spinal column, which are a common result of osteoporosis. Doctors displace portions of the fractured bone to create a space and then fill the space with cement or another filler, such as an implant.

SUMMARY

This disclosure describes surgical implants, surgical implant assemblies, methods for manufacturing surgical implants, and methods for using the surgical implants to support collapsed structures in the body.

In certain aspects, spinal implant device includes a unitary strand extending from a first end to a second end. The unitary strand includes an exterior surface defining an infill volume with an infill structure. The exterior surface extends from the first end to the second end. A first bead is formed in the strand has a first diameter. The second bead is formed in the strand has a second diameter. At least one joint is formed in the strand between the first bead and the second bead. The at least one joint has a third diameter that is less than the first diameter and less than the second diameter.

In some implants, the infill structure of the internal volume is a gyroid infill structure and/or is a honey comb infill structure.

The infill structure can extend from the first end of the unitary strand to the second end of the unitary strand.

In some implants, the at least one joint includes a plurality of filaments. In some implants, the filaments have a diameter of about 0.5 mm to about 30 mm. The plurality of filaments can include at least four filaments. Some plurality of filaments have five filaments in a cross shape.

The unitary strand, the at least one joint, and/or the beads can be formed by formed by PEEK, PEKK, or a combination thereof.

Some spinal implant devices also include a set of radiopaque markers arranged in the unitary strand. The set of markers may include a first marker embedded in the first bead. The set of markers may also include a second marker embedded in a second bead. Some first and/or second markers are a tantalum sphere, a tantalum pin, omnipek, and/or a ligating clip.

In some implants, the first bead has a first modulus of elasticity, the second bead has a second modulus of elasticity, and the joint has a third modulus of elasticity. The third modulus of elasticity may be less than the first and the second modulus of elasticity. The first modulus of elasticity may be equal to the second modulus of elasticity.

In some implants, the infill structure includes a bead infill structure and a joint infill structure. The bead infill structure may be different from the joint infill structure or the same as the joint infill structure.

In some implants, the exterior surface includes a mesh has multiple openings configured to receive new bone growth.

In certain aspects, spinal implant device includes a chain formed by multiple connected links. Each link of the multiple links is formed by an osteoconductive material and includes a socket at a first end of the link and a joint. The socket has a socket body with a socket radius and opening defined by the socket body. The socket body has an outer face and a smooth inner face. The opening of the socket body extends from the outer face to the inner face and has an opening radius. A socket recess is defined by the inner face of the socket body and has a recess has a recess radius. The opening connects to the socket recess to receive an adjacent link. The joint extends from the socket boy to a second end of the link. The joint includes a ball at the second end of the link, and a shaped body extending between the ball and socket body to connect the ball of the link with the socket body of the link. The ball has a ball radius less than the socket radius and greater than the opening radius. The socket recess is sized to receive a ball from another link.

In some implant devices, each link of the multiple links includes an external surface defining an internal volume. The internal volume has an infill pattern. In some spinal implant devices, the infill pattern is a gyroid infill pattern and/or is a honeycomb infill pattern.

In some spinal implant devices, the socket radius is about ½ cm to about ⅔ cm, or about ⅚ cm. Some socket radii are double the ball radius.

In some spinal implant devices, the shaped body can have a length and a height. For example, the shaped body height can be two thirds of the socket radius.

In some spinal implant devices, the multiple connected links include a first link with a first ball and first socket inserted into a second link has a second ball and socket. The first ball may be arranged in a socket recess defined by an inner face of the second socket. The first ball can be distanced from the inner surface by a distance. The distance is about 8% of the socket radius or about 10% of the socket radius.

Some shaped bodies include a pivot and the ball is rotatable around the pivot. In some spinal implant devices, the shaped body has a first portion and a second portion and the pivot connects first portion to the second portion. In some spinal implant devices, the first portion of the shaped body of the joint extends from the socket body and the second portion of the shaped body extends from the ball of the joint. The pivot can be arranged in the second portion of the shaped body. Some pivots of the joint are adjacent to the ball of the joint. The pivot may be a first pivot and the shaped body may include a second pivot. In some spinal implant devices, the second pivot is a living hinge. The first pivot and/or second pivot may be a hinge, a living hinge, a flexible material, a revolute joint, a ball joint, and/or roller joint.

In some spinal implant devices, the shaped body has a first portion, an intermediary portion, and a second portion. The first pivot can connect first portion to the intermediary portion and the second pivot connects the intermediary portion to the second portion.

Some links are or include titanium.

In some spinal implant devices, the socket includes at least three arced protrusions extending from the joint. The at least three arced protrusions define the recess. In some spinal implant devices, the socket includes at least four arced protrusions. In some spinal implant devices, the socket further includes slots defined between the at least three arced protrusions. In some spinal implant devices, the slots are sized to receive the body of a link. In some spinal implant devices, the slots each include a guide portion and a locking portion. In some spinal implant devices, the socket includes a fillet arranged on a wall of the socket defining the recess. The fillet may protrude into the recess.

Some spinal implant devices can include a set of radio-opaque markers where each marker attaches to a corresponding link. The set of markers may include a first marker attached to a first link of the chain. In some spinal implant devices, the first marker is omnipek or is a ligating clip. Some spinal implant devices can include a second marker attached to a second link of the chain. A ball of the first link can be arranged in a socket of the second link. The second marker may be omnipek or a ligating clip.

In some spinal implant devices, the shaped body includes a flexible portion, and the ball is rotatable around the flexible portion. A pivot may be arranged adjacent the ball.

In certain aspects, a spinal implant device includes a foldable chain extending from a first end to a second end. The chain includes multiple rotatably connected links formed by at least one osteoconductive material. The multiple connected links includes a first link and a second link. The first link includes a first socket at a proximal end of the first link, and a first joint extending from the first socket to a distal end of the first link. The first joint includes a first insert at the distal end and a first shaped body extending between the first insert and first socket body to connect the first insert of the first link and first socket of the first link. The second link includes a second socket at a proximal end of the second link, and a second joint extending from the second socket to a distal end of the second link. The second link includes a second insert at the distal end and a shaped body extending between the second insert and the second socket. The second insert is arranged in the first socket. The second shaped body connects the second insert of the second link and second socket of the second link has a first pivot. The second insert and the first pivot form a rotatable connection. The chain is configured to fold at least at the rotatable connection.

In some implants, the first link includes a first external surface defining a first internal volume. The first internal volume has a first infill pattern. The first infill pattern can be a gyroid infill pattern and/or a honeycomb infill pattern.

In some implants, the second link includes a second external surface defining a second internal volume. The second internal volume can have a second infill pattern. In some implants, the second infill pattern is a gyroid infill pattern and/or a honeycomb infill pattern.

The first socket can include a first socket body with a first socket radius. The first socket body has a first outer face and a smooth first inner face and a first opening defined by the first socket body. The first opening extends from the first outer face to the first inner face. The first opening has a first opening radius. The first socket also includes a first socket recess defined by the smooth first inner face of the first socket body, the first recess has a first recess radius. The first opening connects to the first socket recess. Some first insert have a first insert radius less than the first socket radius and greater than the first opening radius. Some first inserts are discs or balls. Some first socket radii are double the first insert radius. The second insert can be distanced from the first inner surface by a distance. The distance may be about 8% of the first socket radius or about 10% of the first socked radius. In some implants, the first socket radius is about ⅙ cm to about ⅓, or about ⅚ cm. The first shaped body may have a first length and a first height. The first body height can be two thirds of the first socket radius. Some first shaped bodies include a first pivot and the first insert is rotatable around the first pivot. In some implants, the first pivot is a hinge and/or a living hinge, a flexible material, a ball joint, a roller joint, a revolute joint, and/or a roller joint.

In some implants with a pivot, the first shaped body has a proximal portion and a distal portion. The proximal portion of the first shaped body of the first joint can extend from the first socket body. The distal portion of the first shaped body can extend from the first insert of the first joint. In some implants, the first pivot is arranged in the distal portion of the first shaped body. In some implants, the first pivot of the joint is adjacent to the first insert of the first joint.

Some second inserts are discs or balls. Some second socket radii are double the second insert radius. The second insert can be distanced from the second inner surface by a distance. The distance may be about 8% of the second socket radius or about 10% of the second socked radius. In some implants, the second socket radius is about ⅙ cm to about ⅓, or about ⅚ cm. The second shaped body may have a second length and a second height. The second body height can be two thirds of the second socket radius. Some second shaped bodies include a second pivot and the second insert is rotatable around the second pivot. In some implants, the second pivot is a hinge and/or a living hinge, a flexible material, a ball joint, a roller joint, a revolute joint, and/or a roller joint.

In some implants with a pivot, the second shaped body has a proximal portion and a distal portion. The proximal portion of the second shaped body of the second joint can extend from the second socket body. The distal portion of the second shaped body can extend from the second insert of the second joint. In some implants, the second pivot is arranged in the distal portion of the second shaped body. In some implants, the second pivot of the joint is adjacent to the second insert of the second joint.

In some implants with a second pivot, the second shaped body has a proximal portion and a distal portion. The proximal portion of the second shaped body of the second joint can extend from the second socket body. The distal portion of the second shaped body can extend from the second insert of the second joint. In some implants, the second pivot is arranged in the distal portion of the second shaped body. In some implants, the second pivot of the joint is adjacent to the second insert of the second joint. The second opening connects to the second socket recess. In some implants, the second insert has a second insert radius less than the second socket radius and greater than the second opening radius. In some implants, the second insert has a second insert radius less than the second socket radius and greater than the second opening radius. The second insert has a second insert radius less than the second socket radius and greater than the second opening radius. In some implants, the second pivot is arranged in the distal portion of the second shaped body. In some implants, the second pivot of the joint is adjacent to the second insert of the second joint.

In certain aspects, a spinal implant device includes a monolithic strand extending from a first end to a second end. The monolithic strand formed by a dehydrated biological material. The monolithic strand includes an exterior surface defining an interior volume of the monolithic strand, and a demineralized layer of the material extending into the interior volume from the exterior surface. The demineralized layer extending from the first end of the strand to the second end of the strand. The strand also includes a first bead formed in the strand having a first diameter and a first core of mineralized material, a second bead formed in the strand having a second diameter and a second core of mineralized material, and at least one joint formed in the strand between the first bead and the second bead. The at least one joint has a third diameter. The third diameter is less than the first diameter and less than the second diameter.

In some implant devices, the material is a cortical bone. In some implant devices, the dehydrated, demineralized material is dehydrated, demineralized bone.

In some implant devices, the demineralized layer encompasses a first core. In some implant devices, the first core is a mineralized bone.

In some implant devices, the demineralized layer is a demineralized bone.

In some implant devices, the demineralized layer encompasses a second core. The second core can be a mineralized bone.

In some implant devices, the first bead includes at least a portion of the demineralized layer.

In some implant devices, the dehydrated, mineralized material swells in the presence of a liquid.

In some implant devices, the dehydrated material is a swellable dehydrated material.

In some implant devices, the dehydrated material is a freeze-dried material.

In some implant devices, the dehydrated material is a freeze-dried cortical bone.

In some implant devices, the first diameter is about 3.2 mm to about 3.7 mm.

In some implant devices, the second diameter is about 3.2 mm to about 3.7 mm.

In some implant devices, the third diameter is about 0.5 mm to about 3 mm.

In some implant devices, the monolithic strand is a milled bone. In some implant devices, the bone is a femur bone. In some implant devices, the milled bone includes cortical bone.

In some implant devices, the joint has a square cross-sectional area.

In some implant devices, the at least one joint is formed of cortical bone.

In certain aspects, a method is disclosed for inserting an expandable implant, the method includes soaking a dehydrated implant in a solution for less than 10 minutes to form a partially rehydrated implant, and inserting the partially rehydrated implant into a cavity of a bone to form a rehydrated implant.

In some methods, the rehydrated implant has a rehydrated volume greater than a dehydrated volume of the dehydrated implant. The rehydrated volume can be at least 20% larger than the dehydrated volume, at least 30% larger than the dehydrated volume, and/or about 40% larger than the dehydrated volume. In some methods, the rehydrated implant has a partially rehydrated volume, and the partially rehydrated volume is less than the rehydrated volume.

In some methods, soaking the dehydrated implant in a solution for less than 10 minutes includes soaking the dehydrated implant for at least 30 seconds, for at least 1 minute, for at least 90 seconds and/or for at least 2 minutes.

In some methods, the implant is a spinal implant. In some methods, the cavity of the bone is in a vertebrae. The implant may be formed by a cortical bone.

In some methods, the implant has a demineralized surface and a plurality of internal volumes spaced evenly along an elongated body of the implant. In some methods, each of the internal volumes include a core of mineralized cortical bone.

In some methods, the partially rehydrated implant is more flexible than the dehydrated implant.

In certain aspects, a method is disclosed for forming a monolithic strand. The method includes milling at least one rod from a cortical bone; shaping the rod of cortical bone into a monolithic strand having at least one bead, demineralizing a surface of the monolithic strand, and dehydrating the monolithic strand.

In some methods, dehydrating the monolithic strand includes reducing the volume of the monolithic strand by at least 10%, by at least 20%, by at least 30%, and/or by about 40%.

In some methods, dehydrating the monolithic strand includes freeze drying the monolithic strand.

In some methods, demineralizing the surface of the monolithic strand includes inserting the monolithic strand into an acid treatment, for example, a hydrochloric acid treatment.

In some methods, the demineralized surface is permeable to water.

In some methods, milling the at least one rod from the cortical bone includes milling multiple rods from the cortical bone and milling the multiple rods into a set of monolithic strands, each set of monolithic strands having at least one bead.

In some methods, the monolithic strand includes plurality of beads, each bead in the plurality of beads connected by a flexible joint.

In some methods, the cortical bone is a femur bone.

In certain aspects, a method is disclosed for manufacturing a flexible spinal implant. The method includes extruding, by a 3D printer, a shell of a first portion of the flexible spinal implant. The shell forms an exterior surface of the implant and defines a first internal volume. The method also includes infilling, by the 3D printer, the first internal volume of the first portion of the implant with a bone-like infill pattern.

In some methods, the bone-like infill pattern is a honeycomb pattern.

In some methods, the bone-like infill pattern is a gyroid pattern.

In some methods, the flexible spinal implant has a unitary strand extending along a first axis.

In some methods, an extruder nib of the 3D printer is oriented perpendicular to the first axis.

In some methods, the first portion extends from the first end of the implant to the second end of the implant.

In some methods, the first portion forms a first half of the implant.

In some methods, the first half the implant includes at least two partially formed beads and at least one partially formed joint connecting the at least two partially formed beads.

In some methods, the first half of the implant includes a first partially formed barrel, a second partially formed barrel, and a partially formed joint connecting the first partially formed barrel to the second partially formed barrel.

In some methods, the first half of the implant has an open end oriented towards the nib of the 3D printer.

Some methods also include printing the shell of the first portion and the infill of the first portion, simultaneously.

Some methods also include extruding a second half of the implant to form a flexible, unitary spinal implant.

Some methods also include extruding a second portion of the shell of the implant. The second shell of the implant defining an interior volume. The method also includes infilling the interior volume with the bone-like infill pattern. Some methods also include extruding a plurality of layers of the second portion, each layer of the plurality of layers includes a layer of the external shell and a layer of an infill pattern. Some methods also include extruding final layer of the second portion of the shell to form the second half of the implant.

In some methods, an extruder nib of the 3D printer is oriented parallel to the first axis. In some methods, the first portion of the implant forms a first end of a unitary strand of the flexible spinal implant. In some methods, the shell of the first portion is a series of external layers of at least one bead of the flexible spinal implant The shell of the first portion may have a closed first end centered on the first axis and an open second end centered on the first axis. In some methods, infilling the first internal volume with the bone-like infill pattern includes infilling the shell of the first portion along the first axis from the closed end of the external layer to the open end of the external layer. The infill pattern can include a series of internal layers. The series of internal layers may be arranged adjacent to corresponding external layers of the shell.

Some methods also include closing, the open second end of the external layer to form the at least one bead. Some methods also include, extruding a joint extending from the closed end of the external layer. The joint may be centered on the first axis. In some methods, the joint is a set of filaments. In some methods, the set of filaments are arranged in a cross pattern. In some methods, extruding the joint extending from the closed end of the at least one bead includes extruding a shell of the joint and infilling the shell of the joint with a bone-like pattern. 213. The method can also include extruding a second portion of a shell of the implant extending from the joint. In some methods, second portion of the shell is a second external layer of at least one bead, where the second external layer having a closed first end centered on the first axis and an open second end centered on the first axis. Some methods also include infilling the second portion of the shell along the first axis from the closed end of the second external layer to the open end of the second external layer. Some methods also include closing, the open second end of the second external layer to form the at least one bead of the second portion of the implant.

In some methods, the first portion is a joint of a link of the implant and the implant includes multiple connected links.

In some methods, the first portion is a socket of a link of the implant and the implant includes multiple connected links. Some methods also include extruding a second portion of the link. The second portion may be a shaped body of a joint of the link.

Some methods also include extruding a third portion of the link, wherein the third portion is an insert of the joint, wherein the shaped body connects the first portion of the link to the second portion of the link.

Some methods also include extruding a second portion of the link. The second portion can have a shell defining an internal volume of the second portion and the internal volume of the second portion has the bone-like infill. The second portion may be a joint. In some methods, the shell of the second portion forms a plurality of openings and the openings expose the bone-like infill.

In some methods, the first portion is a partially formed socket at a first end of the link and a partially formed joint at the second end of the link. The first end of the link and the second end of the link can define a first axis and a nib of the 3D printer can be oriented perpendicular to the first axis. In some methods, the first portion is a first half of the link. The method can also include extruding a second half of the link. The second half of the link may have the bone-like infill pattern. In some methods, the shell of the first portion forms a plurality of openings, wherein the apertures expose the bone-like infill.

Implant devices, systems, and methods for providing a flexible strand of biocompatible material that can be partially and rehydrated to greater volumes is disclosed. In this configuration, a monolithic strand formed by milling, shaping, demineralizing, and dehydrating (e.g., by freeze-drying) can be swollen immediately prior to insertion into a body in a pre-soaking step. The dehydrated monolithic strand can be stored at room temperature, for example on a shelf in a hospital. In the pre-soaking stage, the implant is inserted into a saline bath for a predetermined period of time (e.g., about 3 minutes). The implant devices increases from a dehydrated volume to a partially rehydrated volume and increases the flexibility of the implant device, in particular the flexibility of joints. The partially hydrated, flexible implant device can be inserted into a cavity of a body and further swollen, in situ, to a rehydrated volume, thereby to support surrounding structures and, in some cases, expanding the structures from the interior of the cavity. The rehydrated strand increases in volume, for example, by about 40% from the dehydrated volume to the rehydrated volume. This expansion, in situ, provides structural support within a cavity, fractur reduction, and vertebral height restoration.

In addition, the implant device with a monolithic strand has a demineralized layer which can increase new bone formation through enhanced osteoconduction and osteoinduction. The implant renders osteogenic when hydrated in situ with a patient's own blood. The flexible strand can provide a less invasive implementation to augment a vertebrae fracture with new bone. Further, the monolithic strand can include or be formed by cortical bone which can increase stability and compressive strength.

Other implants can be formed by 3D printing methods and systems rather than by milling, shaping, demineralizing, and dehydrating a cortical bone. In 3D printed strands or chains, the implants can include specially printed surfaces (exteriors) and infill structures to increase surface area available for osteointegration and osteoconduction. The infill structures, for example, can imitate or mimic the structure of a cortical bone or cancellous bone to promote osteointegration and osteoconduction. Further, the implants can provide smooth surfaces at locations of the implant that experience high levels of friction. For example, where the implant is formed by connected links which attached to each other by ball-and-socket attachment structures, the sockets can include smooth inner surfaces to decrease wear and material degradation. Additionally, the implant can have customized or adjustable modulus of elasticity between different portions of the implant.

The details of one or more embodiments of these devices and methods are set forth in the accompanying drawings and the description below. Other features, objects, and advantages of these devices and methods will be apparent from the description and drawings, and from the claims.

DESCRIPTION OF DRAWINGS

FIG. 9 is a flowchart of a method for inserting an expandable implant into a body.

DETAILED DESCRIPTION

Figure 1A:
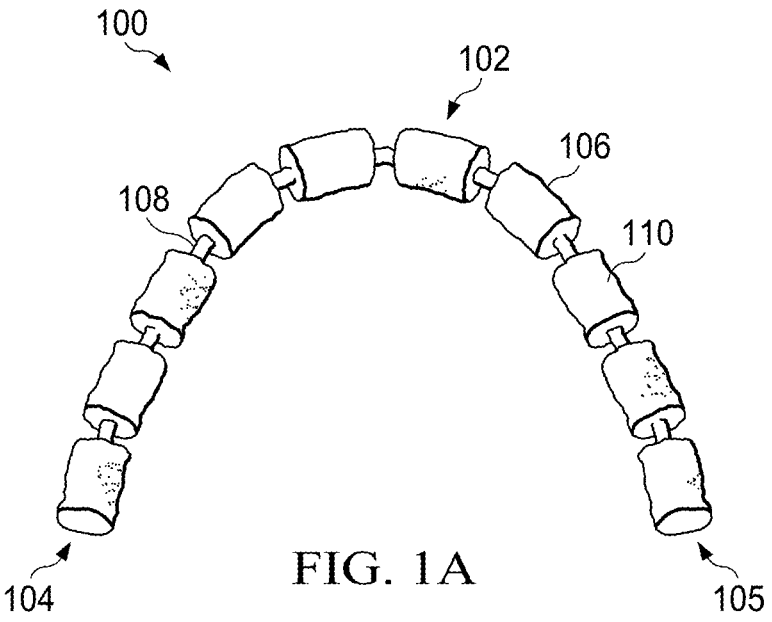
FIGS. 1A and 1B are perspective views of a flexible spinal implant device with a monolithic strand in a dehydrated state and a rehydrated state.

This specification describes assemblies, implant devices, and methods for supporting collapsed structures in the body. These systems and methods can be used for restoring bone, particularly for maintaining bone alignment after displacement in the spine of a human or other animal.

Some assemblies include an implant device with a monolithic elongated body formed by either a unitary strand or formed by a chain of interconnected links. The elongated body includes large diameter sections, described as beads and/or sockets, connected to each other by small diameter sections, described as joints and/or shaped bodies. The joints are flexible or rotatable so that the elongated body is collapsible and folds when compressed. The implant can then be manipulated as needed to form a thin, elongated string or to form a dense cluster or mass. In the folded configuration, the elongated body folds at the joints to move the beads towards each other, thereby forming dense cluster of beads capable of supporting collapsed structures like collapsed bones while still providing open macro spaces between the beads for vascular through flow and delivery of patients own nutrients, bmp's etc. to the implant. Further, the cluster of beads can form a variety of regular or irregular shapes in the partially rehydrated or rehydrated state. In use, a surgeon expands a collapsed vertebrae then inserted the implant device into the expanded vertebrae to support the vertebrae in the expanded position. In use, a surgeon inserts the implants into the collapsed vertebrae and through implant impaction, increases the height and/or restores the height of the vertebrae. In situ swelling further expands the vertebra and creates a sturdy mass to support the loads exerted to the spine and/or vertebrae.

The implant device is inserted as a linear string (or individual beads) through a cannula, then randomly folds in the vertebrae to form a dense support with macro spaces for vascular through and inflow. The implant device can be used, for example, to support the structure of a collapsed vertebrae during surgery and comprises an osteoconductive material and/or osteoinductive material to promote natural bone growth. When combined with the patient's own blood and nutrients, the implant can be rendered osteogenic.

The monolithic strand can be formed using biological materials, through bone milling, or using inorganic materials, through 3D printing. In a monolithic (unitary, single material) strand, the beads and joints are integrally connected and are generally sculpted and shaped from a single piece of material. In some implants, the unitary strands are formed by extruding or printing an elongated strand of joints and bead. The extruded or printed strands are infilled with at least one bone-like infill pattern which can mirror the structure of a cortical bone or a cancellous bone. The bone-like infill pattern can promote bone growth during the healing process.

The linked chain is formed by 3-D printing each individual link in connection with each other by attachment structures (e.g., a ball-and-socket). The attachment structures are printed within each other in in configurations that are not achievable by present machining methods. The attachment structures are therefore in permanent attachment, engagement, or connection with each other directly after or during printing. The attachment structures are mounted on or formed by each of the links. For example, a first link has a first attachment structure, e.g., a socket, and a second link has a second attachment structure, e.g., a ball insert. The ball and socket attachment structures form a rotatable connection between the first and second links. The chain of connected links can collapse, condense, or fold along the link connections to form a dense structure capable of supporting a collapsed bone. Some chains have an identical attachment structures on the links whereas other chains may have unique attachment structures connecting each link. For example, a first and second link can be attached by a ball and socket connection, whereas the second and third link may be attached using a socket and disc connection. Further, the attachment structures can be customized to resist axial movement within the connection (e.g., close fit between the ball and socket) or permit a known amount of axial movement (e.g., a disc and socket connection in which the disc can move axially within the socket).

The implant is printed as a connected chain in a single printing run. In one exemplary method, a first half of each link is printed so that a half-formed ball of the link lays in a smooth inner surface of half-formed socket of another link. A second half of the ball may be printed over the first half to form a completed ball of the link arranged in a half-formed socket of a second link. The second half of the socket of the other link is then printed around the fully formed ball to form a ball-and-socket rotatable connection with a predetermined gap. Upon completion of printing, the ball has a radius larger than any (e.g., one or more) opening of the socket. In this configuration, the ball is permanently installed in the socket. The printing can via layers, (e.g., one small layer at the time). A cross sectional layer will include portions of the socket and the ball. Layers will be printed on top of each other or sometimes a powder is melted into a layer and then a new layer is melted. As such, the links of the implant may be formed to have the attachment structures connected to adjacent links upon completion of the printing of the implant. In some implants, an individual link may be printed onto a formed chain to elongate the formed chain by a single link. In some implants, individual links are printed then connected by attachment structures to form the elongated body at a customized chain length.

The flexible implant device may be used to treat disease and pathological conditions in general orthopedic applications such as long bone infections, comminuted complex fractures, tumor resections and osteotomies, joint fusions such as sacro iliac joints, intervertebral joints. Additionally, the device can be used to treat disease and pathological conditions in spinal applications, such as, for example, degenerative disc disease, collapsed intervertebral discs, vertebral body tumor or fractures, vertebral body resections or generally unstable vertebral bodies. Fusions of sacro iliac joints. In other embodiments, a flexible implant device may be used in maxillofacial applications or in non-fusion nucleus replacement procedures.

Figure 1B:
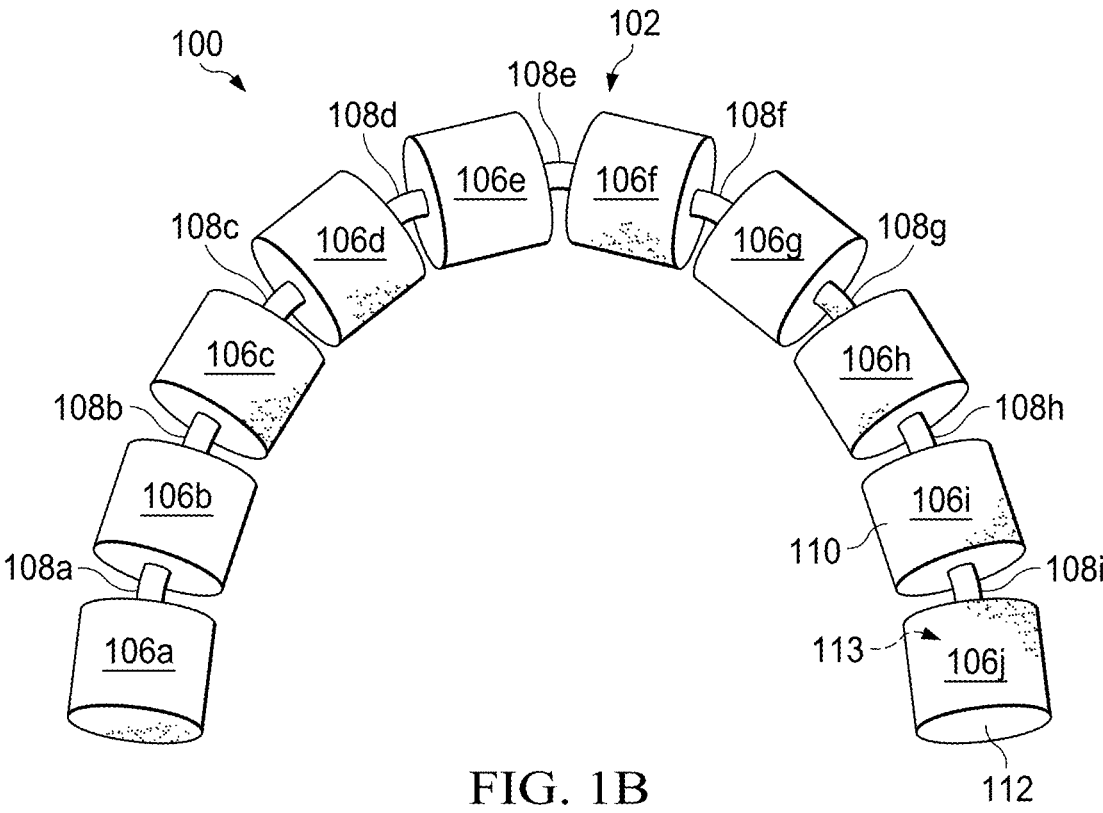

FIGS. 1A and 1B are perspective views of a flexible spinal implant device 100 with a monolithic strand 102 in a dehydrated state and a rehydrated state. The monolithic strand 102 is an elongated body extending from a first end 104 to a second end 105. The strand 102 is fabricated and shaped from a single piece of bone which has been at least partially demineralized and at least partially dehydrated (e.g., freeze-dried). The implant device 100 is a single piece of shaped cortical bone milled from a femur (or tibia, radius, ulna, humerus) bone, however, other implant devices can be single pieces of shaped cancellous bone or a naturally occurring combination of cortical (compact) bone and cancellous (spongy, trabecular) bone. The single piece of bone material can be sourced from any available bone with cortical and/or cancellous bone material. Cortical bone has a dense, rigid, load bearing structure, whereas cancellous bone has a webbed structure of interconnected rods-like structures.

The monolithic strand 102 includes a series of large-diameter bodies spaced equally along the strand 102. In the device 100, the large-diameter bodies are masses or beads of a biocompatible material. The strand 102 also includes a series of small-diameter sections arranged between adjacent beads 106. In the device 100, the small diameter sections are joints 108. The beads 106 and joints 108 are integrally formed and are shaped from a single piece of bone, for example cortical bone and/or cancellous bone. In some spinal implant devices, the strand can include or be embedded with biocompatible material, for example a biocompatible polymer, metal, ceramic, composite, or any combination thereof. Further, some implant devices have osteoinductive properties and/or are made at least partly from osteoinductive materials. In some implants, the elongated body (e.g., strand) can be soaked with a substance to provide therapeutic effects such as osteogenesis, chemotherapeutic agents, infectious treatment agents such as antibiotics or pain relief agents. The beads 106 are uniform in shape in the rehydrated state, however, some strands many have non-uniformly shaped beads.

In the presence of a presoaking fluid (e.g., saline, or another fluid including a fluid with medicament, medicament agents, or other therapeutic agents), the implant may be configured to release a medicament or therapeutic agent prior to, during, or after insertion into the body. The strand 102 swells and expands to increase in all dimensions (e.g., length, width, and height) at equal rates or at inequal rates, thus increasing in total strand volume. The rate of expansion or swelling can be adjusted by the amount of fluid present and/or the length of time in the pre-soaking fluid. For example, submerging the implant device 100 in a fluid results in a higher expansion rate than misting the implant device 100 or steaming the implant device. In some strands, only one or two dimension of the strand increase in the presence of saline at the same rate. In some strands, at least two dimension increase in the presence of saline, but the at least two dimensions increase at different rates. Implant devices formed by a combination of cancellous and cortical bone material may swell non-uniformly. For example, as cancellous bone has a hinge porosity (about 70% to 80%), fluid can permeate and rehydrate a cancellous portion of the strand more quickly than a cortical portion of the strand. Thus, beads, joints, and/or portions thereof formed by the cancellous bone may swell at a faster rate than beads, joints, or portions thereof formed by the cortical bone.

In the dehydrated state, the strand 102 has a dehydrated volume. In the rehydrated state, the strand 102 has a rehydrated volume, greater than the dehydrated volume, for example, a volume of the strand prior to a dehydration stage (e.g., a freeze drying stage), during manufacturing of the strand. The strand 102 also has a partially rehydrated volume (not shown) which is less than the rehydrated volume but greater than the dehydrated volume. In the implant device 100, the rehydrated volume is about 20% greater than the dehydrated volume.

The beads 106 include a first bead 106a, a second bead 106b, a third bead 106c, a fourth bead 106d, a fifth bead 106e, a sixth bead 106f, a seventh bead 106g, and eighth bead 106h, a ninth bead 106i, and a tenth bead 106j. The first and second beads 106a, 106b are connected by a first joint 108a. The second and third beads 106b, 106c are connected by a second joint 108b. The third and fourth beads 106c, 106d are connected by a third joint 108c. The fourth and fifth beads 106d, 106e are connected by a fourth joint 108d. The fifth and sixth beads 106e, 106f are connected by a fifth joint 108e. The sixth and seventh beads 106f, 106g are connected by a sixth joint 108f. The seventh and eighth beads 106g, 106h are connected by a seventh joint 108g. The eighth and ninth beads 106h, 106i are connected by an eighth joint 108h. The ninth and tenth beads 106i, 106j are connected by a ninth joint 108j. Some implant are formed as a collection of at least one loose bead without joints.

While the device 100 is described to have ten beads, some devices have less than ten beads or more than then beads. Additionally, some devices have more than nine joints or less than nine joints. The strand 102 has been described as a single strand of elongated body, however, some devices may be woven plaits or planes of singles strands. Some devices can include a tassel having multiple strands extending form a single connector. Some devices may be a single strand of elongated material with an equal number of joints and beads, forming a closed shape, for example a circle (loop, ring), ellipse, oval, square, rectangle, or triangle. Some devices may include branching or forked strands or individual, unattached beads.

The strand 102 has an exterior surface 110 extending from the first end 104 to the second end 105. The exterior surface 110 defines an interior volume 113 of the strand 102. During manufacturing, the strand 102 is treated with a demineralizing treatment which forms a demineralized layer 112 of demineralized material (demineralized bone). The demineralizing stage is further detailed with reference to FIG. 13. The exterior surface 110 defines an edge of the demineralized layer 1128. The demineralized layer 112 extends from the exterior surface 110 into the interior volume 113 of the strand 102. In some cases, the demineralized layer and/or exterior surface is a coating encompassing the elongated body of the strand. In some cases, the exterior surface of the strand is a coating, and the demineralized layer is arranged in the interior volume of the implant device. In some implants, the strand, or a portion of the strand can be coated, imputed, or imbibed with a therapeutic agent or medicament.

Figure 2A:
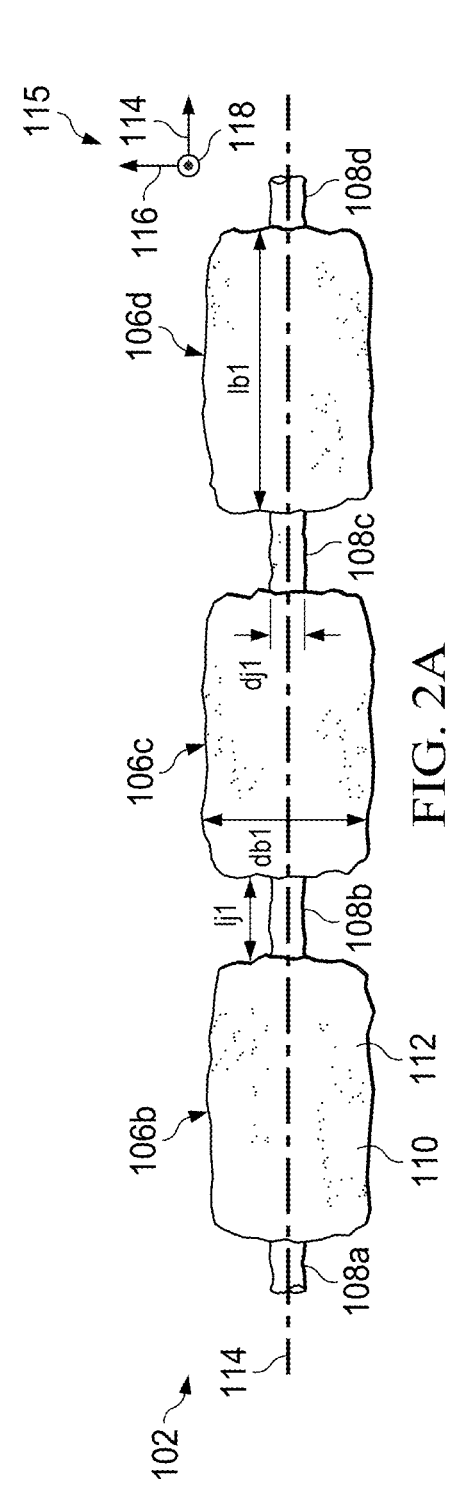
FIG. 2A is close-up front view of the second, third, and fourth beads of the spinal implant device in the dehydrated state.

FIG. 2A is close-up front view of the second, third, and fourth beads 106b-d of the spinal implant device 100 in the dehydrated state. The strand 102 is oriented in a space defined by three intersecting axes as indicated in an orientation icon 115. The terms "height," "width," and "length" herein are distances or dimensions measured along the three perpendicular axes. For example, the first end 104 of the strand 102 and the second end 105 of the strand 102 define a length (first) axis 114, a height (second) axis 116 is perpendicular to the length axis, and the width (third) 118 axis is perpendicular to both the length axis 114 and the height axis 116.

The strand 102 has a dehydrated linear length l1 measured from the first end 104 to the second end 105 may be made as long as practical for a particular application. For implantation into a bone may be about 50 top about 70 mm (e.g., about 62.6 mm) in length. Other strands may have other lengths, for example less than about 1 mm, between about 1 mm and about 100 mm, at least 1 mm, at least 5 mm, at least 10 mm, at least 20 mm, at least 25 mm, at least 30 mm, at least 40 mm, at least 50 mm, at least 75 mm at least 100 mm, at least 150 mm, at least 200 mm, at least 250 mm, at least 300 mm, at least 350 mm, at least 400 mm, at least 450 mm, at least 5 cm, at least 5.5 cm, at least 6 cm, at least 6.5 cm, at least 7 cm, at least 7.5 cm, at least 8 cm, at least 8.5 cm, at least 9 cm, at least 9.5 cm, or at least 10 cm.

Each bead 106a-j of the plurality of beads 106 includes a dehydrated diameter db1 and a dehydrated length lb1. In the implant device 100, the dehydrated bead diameter db1 is about equal for each bead 106a-j. Additionally, dehydrated length lb1 is about equal for each of the beads 106a-j. The dehydrated bead diameter db1 is about 1 mm to about 15 mm, for example, about 2 mm to about 8 mm, or about 4 mm to about 6 mm. The dehydrated length lb1 of the beads 106 is about The dehydrated bead diameter db1 is about 0.5 mm to about 50 mm, for example, about 1 mm to about 25 mm, about 4 mm to about 10 mm, about 5 mm to about 40 mm, about 2 mm to about 15 mm, about 1 mm to about 8 mm, about 0.5 mm to about 5, bout 2 mm to about 6 mm, about 3 mm to about 5 mm, about 1 mm to about 4 mm, or about 2 mm to about 4 mm.

In some cases, the dehydrated diameter of each bead is at least partially based on the biological material forming the bead (e.g., cortical bone or cancellous bone) and/or on the moisture content of the bead. In some implant devices, the beads can have a variety of dehydrated diameters different from each other.

In some implant devices, the beads can have a variety of lengths different from each other. In some cases, the length of each bead is at least partially based on the biological material forming the bead (e.g., cortical bone or cancellous bone), the amount of demineralization, and/or on the moisture content of the bead.

The dehydrated and rehydrated beads 106 have a generally cylindrical shape and have a generally circular cross-sectional area taken parallel to the height axis 116. The dehydrated and rehydrated bead diameters db1, db2 define both the width and the height dimensions of the beads 106. In some strands, the beads are geometrically shaped so that the height and width are equal, but the cross section of the bead is not circular (e.g., a square, hexagon, octagon, etc.). In some strands, the beads are geometrically shaped so that the height and width are different (e.g., triangle, pentagon, heptagon, etc.). In some cases, the dehydrated bead is deformed or dehydrated so that the dehydrated bead is an irregular 3-D shape.

Regardless of the geometric shape or cross-sectional area of beads and joints, each joint has a smaller cross-sectional area (or average cross-sectional area) than the cross-sectional area (or average cross-sectional area) of the adjacent or flanking beads. An average cross-sectional area of a bead or joint may be taken along the length axis in a plane formed by or parallel to the plane formed by the intersection of the width axis and the height axis.

Each joint 108a-i of the at least one joint 108 has a dehydrated diameter dj1 and a dehydrated length lj1. In the implant device 100 the dehydrated joint diameter db1 is about equal for each joint 108a-i. The dehydrated joint diameter dj1 is about 0.5 mm to about 4 mm (e.g., about 1 mm or about 2.4mm), for example,. about 0.5 mm to about 8 mm, about 0.8 mm to about 4 mm. The dehydrated length dj1 of the joints 108 is about 0.5 mm to about 15 mm, for example, about 0.5 mm to about 5.0 mm, about 1.5 mm to 3.5 mm, about 6 mm and about 10 mm.

Figure 2B:
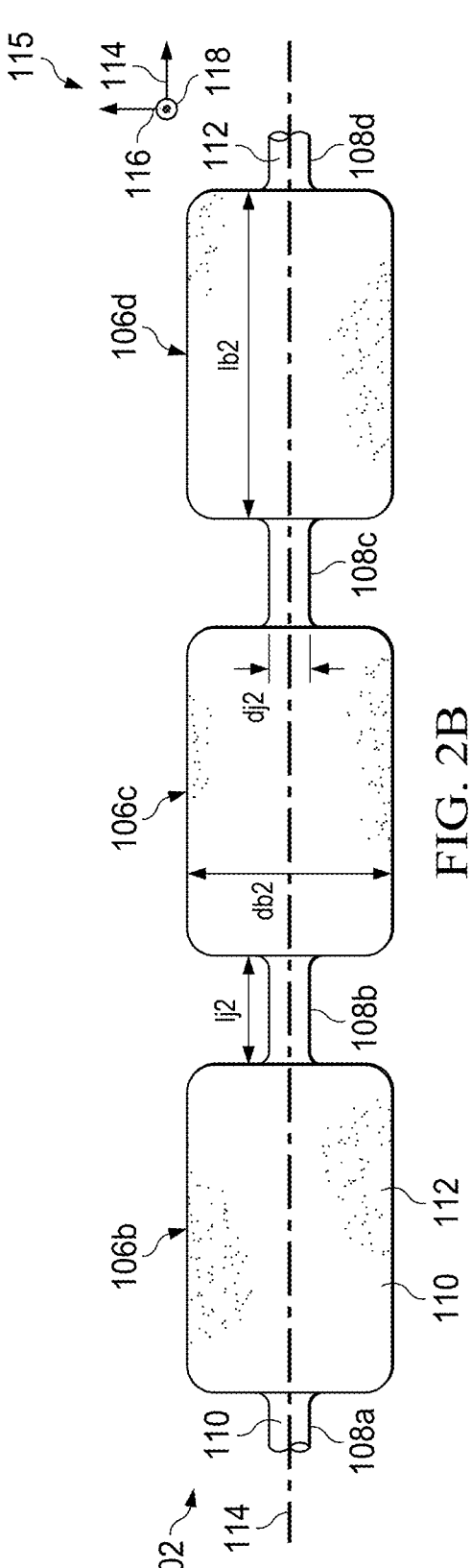
FIG. 2B is close-up front view of the second, third, and fourth beads of the spinal implant device in the rehydrated state.

In some cases, the dehydrated joint diameter is at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm. In some cases, the joints have a diameter proportional to the dehydrated bead diameter. For example, the joint diameter may be about 10% about 20% about 25% about 20 % about 22% about 40% about 50% about 60% about 66%, about 70% about 75% about 80% or about 90% of the dehydrated bead. In some cases, the dehydrated joint diameter is proportional to the rehydrated bead diameter (FIG. 2B).

In some implant devices, the joints can have a variety of dehydrated diameters different from each other. In some cases, the dehydrated diameter of each joint is at least partially based on the biological material forming the joint (e.g., cortical bone or cancellous bone) and/or on the moisture content if the joint. In the implant device 100 the dehydrated joint length lj1 is about equal for each joint 106a-j. The dehydrated dimensions (e.g., length, width, heights, and/or diameter) are influenced by the level of demineralization and/or a depth of the demineralized layer extending from the exterior surface. The more demineralized the strand (e.g., the greater the demineralized layer depth into the interior volume of the strand), the greater the reduction in size of the implant due. A more demineralized implant may have a larger change between the dehydrated diameter and the rehydrated diameter, as compared to a less demineralized implant.

In some strands, the dehydrated length is at least about 0.75 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm, greater than 0.5 mm, greater than about 5 mm. In some cases, the joints have a length proportional to the dehydrated bead length. For example, the joint length may be about 10% about 20% about 25% about 30 % about 33% about 40% about 50% about 60%, about 66%, about 70% about 75% about 80%, about 90%, about 110% about 120% about 125% about 130 % about 133% about 140% about 150% about 160%, about 166%, about 170% about 175% about 180%, about 190%, about 200% about 250%, about 300%, about 400%, about 500%, about 600%, about 700%, about 750%, about 800%, or about 900% of the dehydrated bead length. In some cases, the dehydrated joint diameter is proportional to the rehydrated bead diameter (FIG. 2B).

In some implant devices, the joints can have a variety of lengths different from each other. In some cases, the length of each joint is at least partially based on the biological material forming the joint (e.g., cortical bone or cancellous bone) and/or on the moisture content if the joint.

FIG. 2B is close-up front view of the second, third, and fourth beads 106b-d of the spinal implant device 100 in the rehydrated state. The strand 102 is oriented in a space defined by three intersecting axes as indicated in an orientation icon 115.

The strand 102 has a rehydrated linear length l2 measured from the first end 104 to the second end 105 may be made as long as practical for a particular application. The dehydrated length l1 of the strand 102 is less than the rehydrated length l2 of the strand 102. For implantation into a bone, the monolithic stand or implant may be about 100 mm in length. Other strands may have other lengths, for example less than about 1 mm, between about 1 mm and about 100 mm, at least 1 mm, at least 5 mm, at least 10 mm, at least 20 mm, at least 25 mm, at least 30 mm, at least 40 mm, at least 50 mm, at least 75 mm at least 100 mm, at least 150 mm, at least 200 mm, at least 250 mm, at least 300 mm, at least 350 mm, at least 400 mm, at least 450 mm, at least 5 cm, at least 5.5 cm, at least 6 cm, at least 6.5 cm, at least 7 cm, at least 7.5 cm, at least 8 cm, at least 8.5 cm, at least 9 cm, at least 9.5 cm, or at least 10 cm.

Each rehydrated bead 106a-j of the plurality of rehydrated beads 106 includes a rehydrated diameter db2 and a rehydrated length lb2. In the implant device 100, the rehydrated bead diameter db2 is about equal for each bead 106a-j. Additionally, rehydrated length lb2 is about equal for each of the beads 106a-j. The rehydrated bead diameter db2 is about 1 mm to about 15 mm, for example, about 2 mm to about 8 mm, or about 4 mm to about 6 mm. The rehydrated length lb2 of the beads 106 is about The rehydrated bead diameter db2 is about 0.5 mm to about 50 mm, for example, about 1 mm to about 25 mm, about 4 mm to about 10 mm, about 5 mm to about 40 mm, about 2 mm to about 15 mm, about 1 mm to about 8 mm, about 0.5 mm to about 5, bout 2 mm to about 6 mm, about 3 mm to about 5 mm, about 1 mm to about 4 mm, or about 2 mm to about 4 mm.

In some cases, the rehydrated diameter of each bead is at least partially based on the biological material forming the bead (e.g., cortical bone or cancellous bone) on the moisture content of the bead and/or the amount/degree of demineralization. In some implant devices, the beads can have a variety of rehydrated diameters different from each other. In some implant devices, the beads can have a variety of lengths different from each other. In some cases, the length of each bead is at least partially based on the biological material forming the bead (e.g., cortical bone or cancellous bone), the amount of demineralization, and/or on the moisture content if the bead.

The rehydrated beads 106 have a generally cylindrical shape and have a generally circular cross-sectional area taken parallel to the height axis 116. The rehydrated bead db2 defines both the width and the height dimensions of the rehydrated beads 106. In some strands, the beads are geometrically shaped so that the height and width are equal, but the cross section of the bead is not circular (e.g., a square, hexagon, octagon, etc.). In some strands, the beads are geometrically shaped so that the height and width are different (e.g., triangle, pentagon, heptagon, etc.). In some cases, the rehydrated bead is deformed, either during manufacturing or insertion so that the rehydrated bead is an irregular 3-D shape. Alternatively, compressive forces from cavity walls may also press the beads in the rehydrated position, into an irregular shape.

Each rehydrated joint 108a-i of the at least one joint 108 has a rehydrated diameter dj2 and a rehydrated length lj2. In the implant device 100 the rehydrated joint diameter db2 is about equal for each joint 108a-i. The rehydrated joint diameter dj2 is about 0.5 mm to about 8 mm, for example, about 0.8 mm to about 4 mm. The rehydrated length dj2 of the joints 108 is about 0.5 mm to about 15 mm, for example, about 0.5 mm to about 5.0 mm, about 1.5 mm to 3.5 mm, about 6 mm and about 10 mm.

In some cases, the rehydrated joint diameter is at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm. In some cases, the joints have a diameter proportional to the rehydrated bead diameter. For example, the joint diameter may be about 10% about 20% about 25% about 20 % about 22% about 40% about 50% about 60% about 66%, about 70% about 75% about 80% or about 90% of the rehydrated bead. In some cases, the rehydrated joint diameter dj2 is proportional to the dehydrated bead diameter db1.

In some implant devices, the joints can have a variety of rehydrated diameters different from each other. In some cases, the rehydrated diameter of each joint is at least partially based on the biological material forming the joint (e.g., cortical bone or cancellous bone) and/or on the moisture content if the joint. In the implant device 100 the rehydrated joint length lj2 is about equal for each joint 106a-j.

In some strands, the rehydrated lengths of the joints 108 are at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm, greater than 0.5 mm, greater than about 5 mm. In some cases, the joints have a length proportional to the rehydrated bead length. For example, the joint length may be about 10% about 20% about 25% about 30 % about 33% about 40% about 50% about 60%, about 66%, about 70% about 75% about 80%, about 90%, about 110% about 120% about 125% about 130 % about 133% about 140% about 150% about 160%, about 166%, about 170% about 175% about 180%, about 190%, about 200% about 250%, about 300%, about 400%, about 500%, about 600%, about 700%, about 750%, about 800%, or about 900% of the rehydrated bead length. In some cases, the rehydrated joint diameter is proportional to the rehydrated bead diameter (FIG. 2B).

In some implant devices, the joints can have a variety of lengths different from each other. In some cases, the length of each joint is at least partially based on the biological material forming the joint (e.g., cortical bone or cancellous bone) and/or on the moisture content if the joint.

The rehydrated and rehydrated joints 108 have a generally cylindrical and have a generally circular cross-sectional area. The rehydrated and rehydrated joint diameters dj2, dj2 define both the width and the height dimensions of the beads 106. In some strands, the joints are geometrically shaped so that the height and width are equal, but the cross section of the joint is not circular (e.g., square). In some strands, the joints are geometrically shaped so that the height and width are different. In some cases, the rehydrated joint is deformed so that the rehydrated joint is an irregular 3-D shape.

Regardless of the geometric shape or cross-sectional area of beads and joints, each joint has a smaller cross-sectional area (or average cross-sectional area) than the cross-sectional area (or average cross-sectional area) of the adjacent or flanking beads. An average cross-sectional area of a bead or joint may be taken along the length axis in a plane formed by or parallel to the plane formed by the intersection of the width axis and the height axis.

The dehydrated and rehydrated joints 108 have a generally cylindrical and have a generally circular cross-sectional area. The dehydrated and rehydrated joint diameters dj1, dj2 define both the width and the height dimensions of the beads 106. In some strands, the joints are geometrically shaped so that the height and width are equal, but the cross section of the joint is not circular. In some strands, the joints are geometrically shaped so that the height and width are different. In some cases, the dehydrated joint is deformed so that the dehydrated joint is an irregular 3-D shape.

Regardless of the geometric shape or cross-sectional area of beads and joints, each joint has a smaller cross-sectional area (or average cross-sectional area) than the cross-sectional area (or average cross-sectional area) of the adjacent or flanking beads. An average cross-sectional area of a bead or joint may be taken along the length axis in a plane formed by or parallel to the plane formed by the intersection of the width axis and the height axis.

Where the beads and joint are irregularly shaped in the dehydrated state or rehydrated state, the joint and beads can have a variety of dimensions. In such a configuration, a dehydrated first bead has a first face connected to a dehydrated joint and a second dehydrated bead has a second face connected to the joint. The joint and flanking beads are centered on an axis. Joint has a length lj along the axis, the first bead has a length lba along the axis and the second bead has a length lbb along the axis. The dimensions for any of the joint, first bead, or second bead, are measured in in a plane perpendicular to the axis (e.g., a cross section of the joint and flanking beads). The dimension is a distance from the axis to the exterior surface along a vector in the perpendicular plane. The dimension of the beads and joint are taken at vectors parallel to each other on corresponding planes perpendicular to the axis. In some strands, the joint has a variety of dimensions along the length of the joint, the first face of the first bead has a dimension, and the second face of the second bead has a dimension. The variety of dimensions of the joint are less than the corresponding dimension on the first bead face. In addition, the variety of dimensions of the joint are less than the corresponding dimension on the second bead face.

In some strands, the joint has a series of dimensions taken along the length lj1, the first bead has a series of dimensions taken along the length lba and the second bead has a series of dimension taken along the length lbb. The average of the series of joint dimensions is less than the average of the series of first bead dimensions. The average of the series of joint dimensions is less than the average of the series of second bead dimensions. The average of the average of the series of first bead dimensions is about equal to the average of the series of second bead dimensions.

Figure 3:
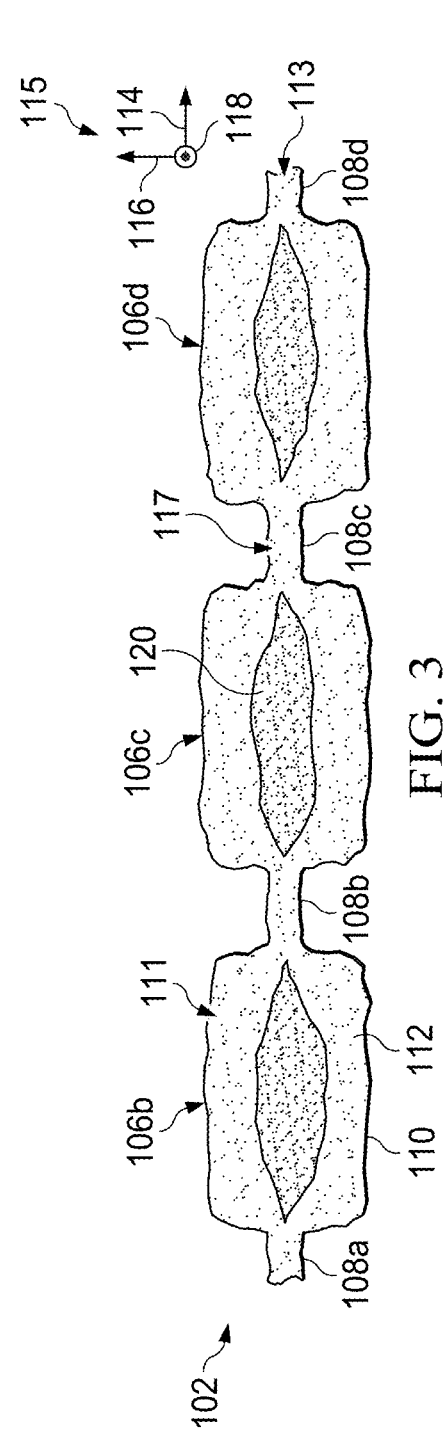
FIGS. 3 and 4 are cross-sectional side views of the spinal implant device in the dehydrated state and the rehydrated state.
Figure 4:
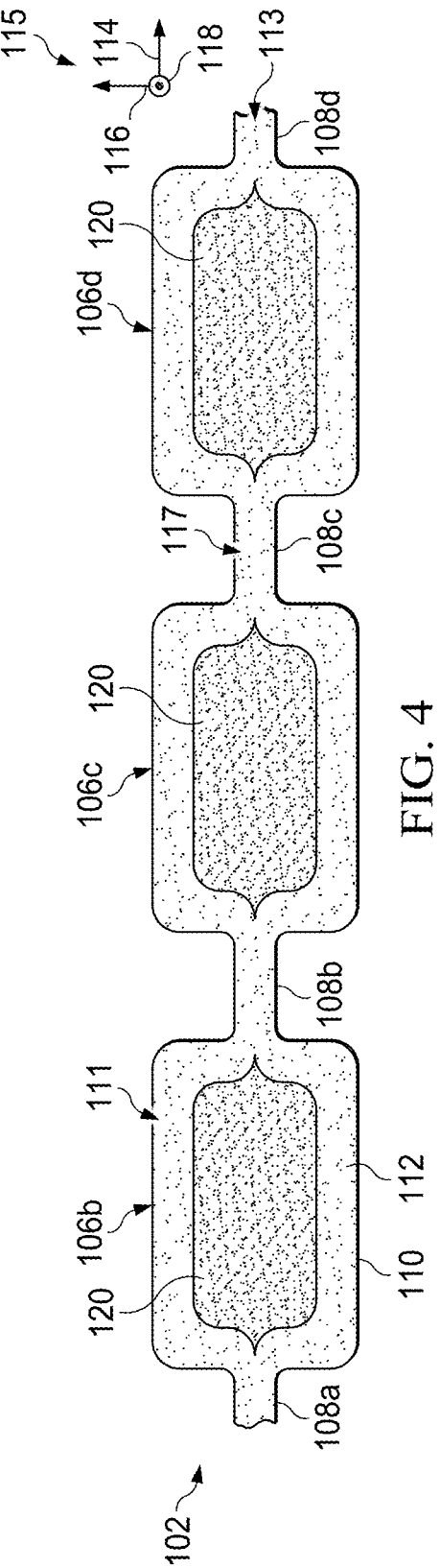

FIGS. 3 and 4 are cross-sectional side views of the spinal implant device in the demineralized, dehydrated state and the demineralized, rehydrated state. The interior volume 113 of the strand 102 is bound or defined by the exterior surface 110 of the strand 102. The demineralized layer 112 extends through the joints 108 so that the joints 108 are formed by demineralized bone.

The demineralized layer 112 extends uniformly into the interior volume 113 of the strand 102. The demineralized layer 112 is uniform due to the methods used in the demineralization stage of manufacture, described in further detail with reference to FIG. 13. As the strand 102 has portions of varying diameter, for example the beads 106 and joints 108, demineralized layer 112 permeates completely through the interior volume 113 at some locations on the strand 102 while other locations of the strand 102 are only partially permeated by the demineralization layer 112. For example, the interior volume 113 includes inner volumes 111 of the beads 106 and inner volumes 117 of the joints 108. As described previously, the cross-sectional area of the of the joints 108 is smaller than the cross-sectional area of the beads 106. In this configuration, the joints 108 have a surface area to volume ratio greater than a surface to area to volume ratio of the beads 106. In environments or treatments where diffusion occurs (e.g., heat transfer or fluid movement) a body greater surface area to volume ratio will experience diffusion more quickly than a body with a lesser surface area to volume ratio. The demineralization process occurs due to a fluid acid treatment diffusing into the strand 102 through the exterior surface 110. In the same amount of time, a fluid demineralization treatment thus demineralizes the entire inner volume 117 of the joint 108 while demineralizing only part of the inner volume of the bead 106.

The bead 106 retains a mineralized core 120 despite the entire strand 102 undergoing a demineralizing treatment. The core 120 thus retains the rigid properties of the natural bone material forming the strand 102. Demineralized bone is more flexible or pliable and osteoinductive. The demineralized layer 112 abuts the mineralized core 120. The mineralized core 120 increase the rigidity of the beads 106. Bother the demineralized layer and the mineralized core shrink or swell during dehydration and rehydration respectively. The demineralized layer may shirk or swell more than the mineralized core in during dehydration and/or rehydration.

The joints 108 have an increased flexibility as compared to the beads 106 due to a smaller joint diameter dj1 and due to the core 120 of mineralized bone. In this configuration, the joints 108 flex, condense, or compress when a force is exerted on the implant device 100. When acted upon by a force, the joints 108 flex and move the beads 106 closer together, forming a cluster or mass of beads 106. The mass of beads 106 is capable of supporting internal bodily structures, such as a collapsed vertebrae of a spine. In addition to forming a dense mass of beads 106, the strand 102 is also swellable in the presence of a fluid. The mass of beads 106 can continue to swell in vivo to further support collapsed structures, and even press the collapsed structure into a healing position.

Figure 5:
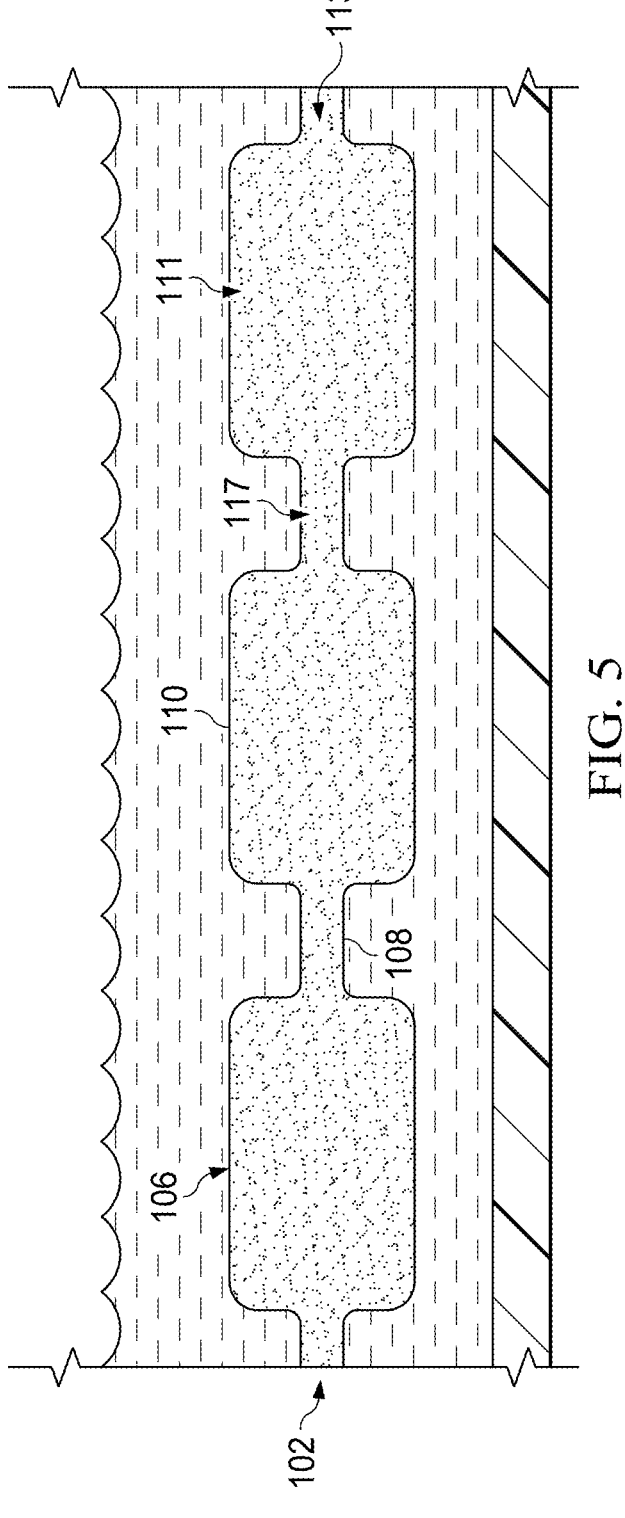
FIG. 5 is a cross-sectional side view of a pre-soaking stage performed immediately prior to insertion of the spinal implant device into a body.

FIG. 5 is a cross-sectional side view of a pre-soaking stage performed immediately prior to insertion of the spinal implant device 100 into a body. At the pre-soaking stage, the implant device 100 is exposed to saline (or a fluid containing a therapeutic agent) for a predetermined amount of time, for example about 2 to about 5 minutes (e.g., about 3 minutes) so that the strand 102 transitions from the dehydrated state a partially hydrated state. In the partially hydrated state, the device 100 swells to a volume greater than the dehydrated volume but less than the rehydrated volume. The rehydrated state is achieved in vivo, when the implant device 100 is placed in a cavity of a body. The fluids in the cavity further soak the device 100 to transition the device into a rehydrated state and/or fluids are conveyed into the cavity in order to contact the implant device and swell the strand 102 in the final, (fully) rehydrated state. Body fluid (e.g., blood) renders the implant osteogenic.

The pre-soaking stage partially rehydrates the dehydrated implant to a volume less than a rehydrated volume but greater than the dehydrated volume. Additionally, the pre-soaking stage increases the flexibility dehydrated material. forming the implant (e.g., the dehydrated cortical bone). The pre-soaking stage can increase the flexibility of the implant from the dehydrated state to a flexibility equal to or slightly less than the flexibility of the implant in the rehydrated state. Thus, in addition to increasing the volume of the monolithic strand, the pre-soaking stage increases the flexibility of the implant so that the implant flexes when inserted into a cavity in a body.

Figure 47:
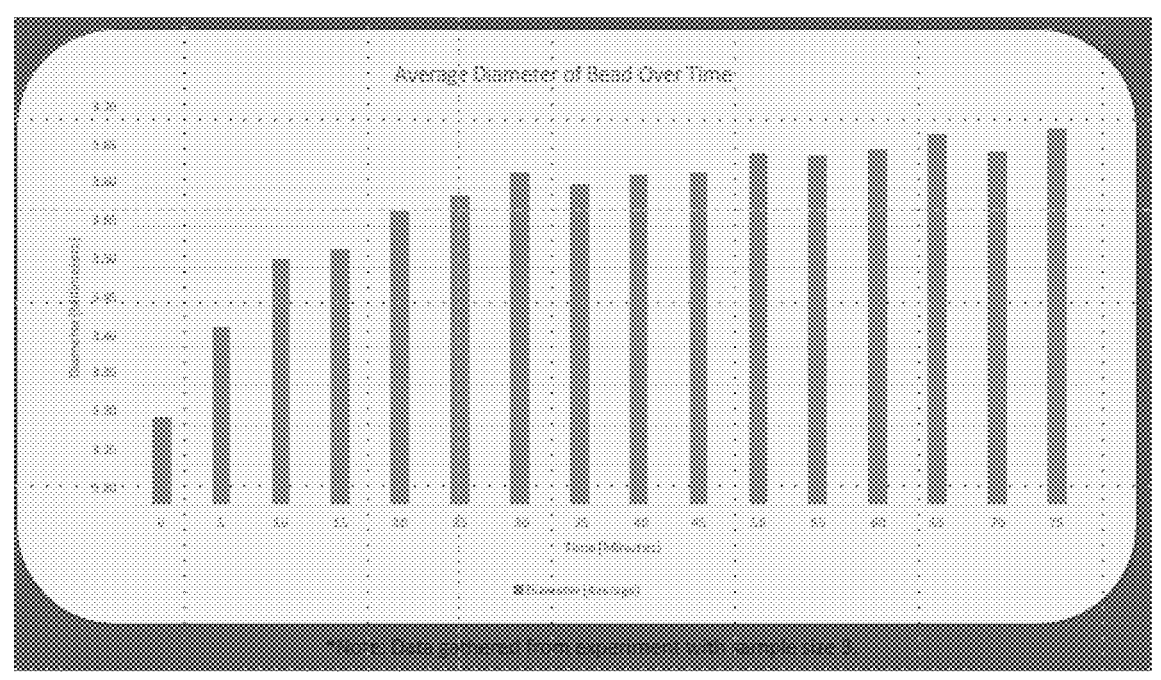
FIG. 47 shows a change in average bead diameter over time in minutes.
Figure 48:
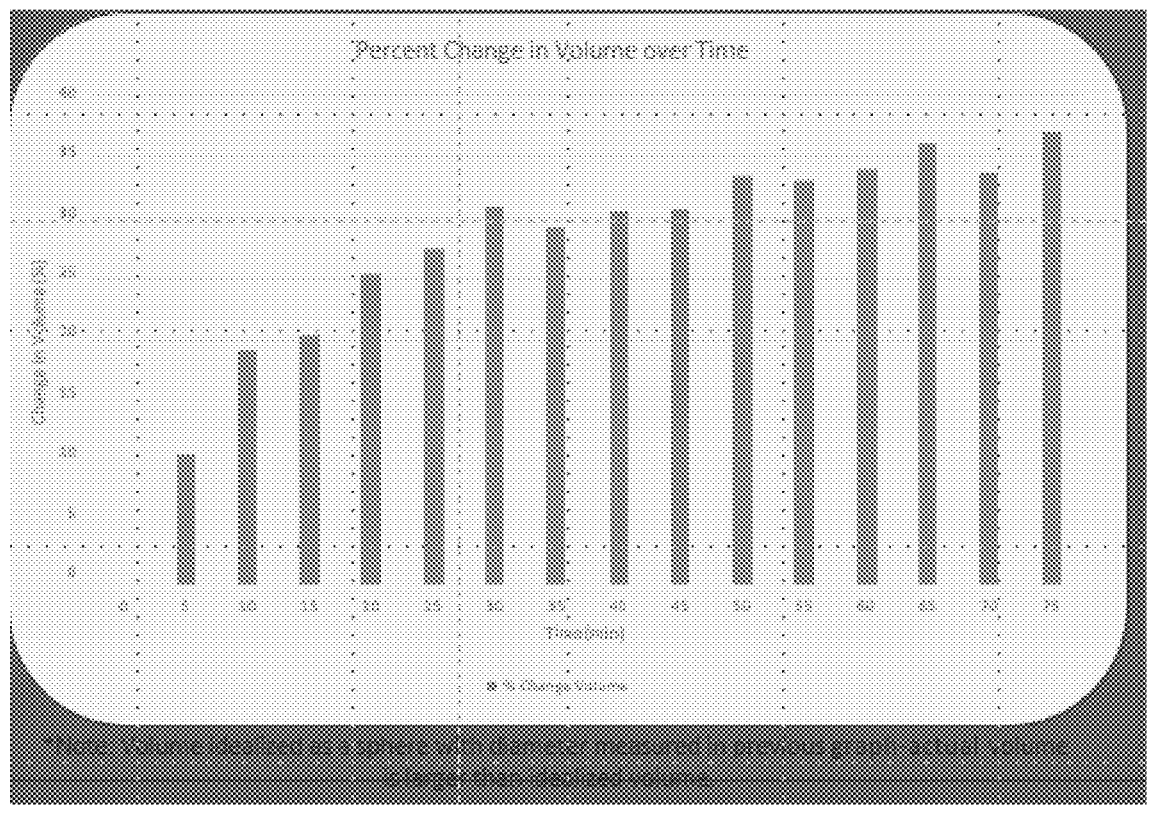
FIG. 48 shows a change in volume (by percent) over time of the implant device.

FIG. 47 shows a change in average bead diameter over time in minutes. FIG. 48 shows a change in volume (by percent) over time of the implant device.

Figure 6:
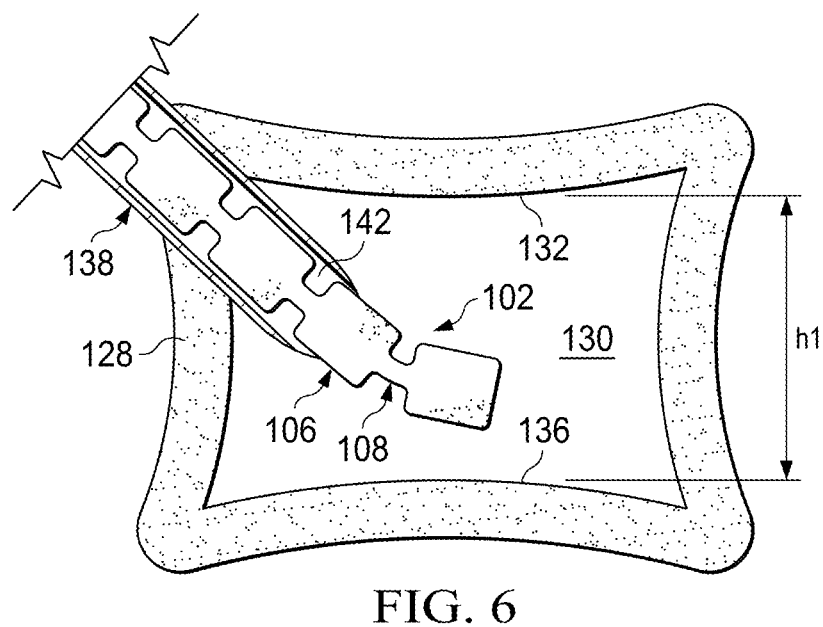
FIGS. 6 and 7 are cross sectional side views of the implant device of FIG. 1A inserted into a damaged vertebrae.
Figure 7:
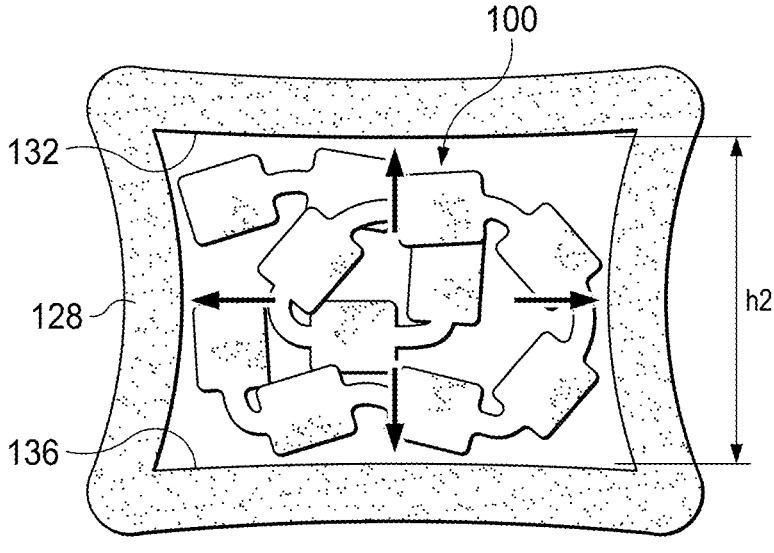

FIGS. 6 and 7 are cross sectional side views of the implant device of FIG. 1A inserted into a damaged vertebrae. The implant is inserted into a shaped cavity of a body so that linked beads of a strand 102 are inserted into a vertebral body 128 and may fill a substantial portion 130. In addition, the beads 106 may also provide structural support to stabilize a vertebral body. In a vertebra that has collapsed, as the strand 102 fills central portion 130 the implant, and particularly the linked beads 106, can push against the interior or inner sides of endplates 132 and 136, thereby tending to restore vertebral body 128 from a collapsed height h1 to its original or desired treated height h2 and provide structural support to stabilize vertebral body 128.

In some cases, an instrument can be inserted through the passageway to restore the height of the vertebra and plates, rather than the strand. For example, a balloon catheter can be inserted to restore vertebra end plates, or an elongated instrument that contacts the inside of the end plates and pushes on them may be utilized. Additionally, the flexibility of one or more joints 108 between beads 106 may allow bending of strand within space 130, e.g., in a uniform pattern or in a non-uniform or tortuous configuration, to aid in ensuring a thorough integration of the implant 100 within the bone 128. The configuration of beads 106 attached by flexible joints also may permit bending to substantially fill the cavity and/or vertebral bone so no large pockets or voids are created or remain which may result in weak spots or a weakened bone structure. The flexible links may also allow the strand to collapse and possibly become entangled so that it becomes larger than its insertion hole so that it cannot be easily ejected.

In other cases, strand 102 may be inserted into a bone such as a vertebral body 128 e.g., through the lumen 142 of a cannula 138 or other sheath, (e.g., a curved sheath to guide implants to lateral sides of the vertebrae when performing a unilateral approach). The sheath may be removed after implantation within the bone 128. In such cases, strand 102, or a portion thereof, may remain in the bone 128 (e.g., vertebral body), for example, to continue augmenting the vertebra and maintain proper lordosis. (i.e., the proper curving inward of the lower back). In other cases, PMMA or another bone cement or filler (for example bone chips) may be inserted sequentially or simultaneously into vertebral body 128 e.g., through shaft and/or a cannula 138, along with beads 106 to further enhance fixation or repair of the damaged region. Alternatively, only a plug of bone cement may be inserted into the hole that was initially formed to insert strands 102 (e.g., plug 812 of FIG. 8A). The plug may cover the insertion hole to prevent the implant (strands) from being removed or ejected. The second end of the implant (e.g., the last beads to be inserted) acts as a plug to plug and heal the insertion hole. May be inserted into vertebral body 128 and a plug of bone cement utilized to hold the linked beads and filler material in the vertebrae.

In some cases, flexible strand 102 may be coated with an adhesive (e.g., therapeutic agents), such that strand 102 may be inserted into vertebral body 128 in a flexible state and may become tangled and/or convoluted during or after insertion. After insertion, beads 106 may become attached together by the adhesive so that the flexible strand becomes a mass that may be locked into the vertebral body, or otherwise secured such that strand 102 may not be easily removed through the insertion opening. When inserted into the vertebrae via the pedicle, there is very minimal risk of expulsion through the insertion hole but there can be a risk of expulsion through fracture lines during insertion of the implant.

In other cases, linked beads 106 may be coated with an adhesive and strand may be inserted, with or without becoming tangled or convoluted, into a vertebral body. During or after insertion of some or all linking beads 106 of a strand 102, a portion of strand 102 may be exposed to an energy source (e.g., an ultraviolet light, ultrasonic radiation, radio waves, heat, electric filed, magnetic field), for example to activate the adhesive, such that the exposed portion of strand 102 becomes joined to form a mass, or becomes rigid, or both, thereby further augmenting the vertebral body 128 and/or preventing removal or ejection of strand 102 through the insertion opening. The beads are impacted into a confined space then swollen to a rehydrated volume. In the rehydrated volume, the swollen implants act as a dam, seal or plug.

Figure 8A:
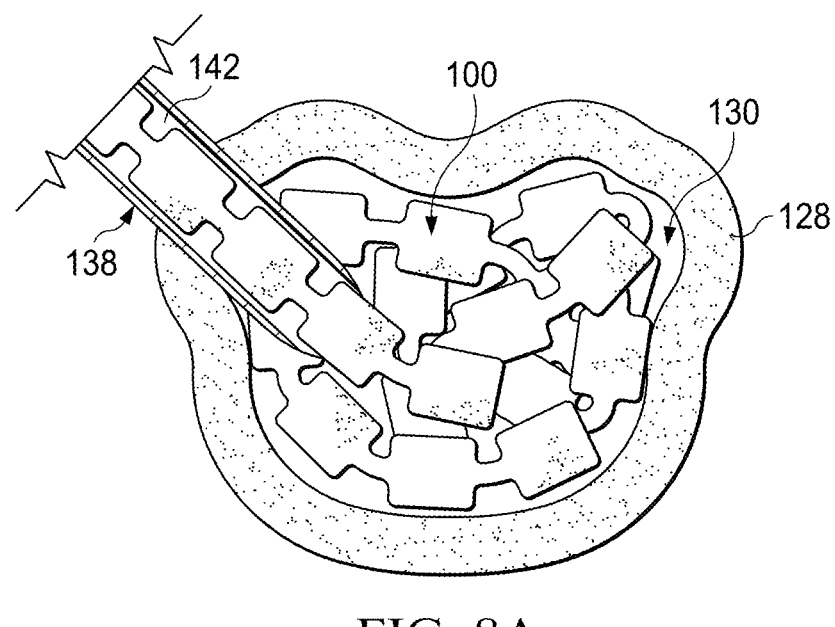
FIGS. 8A and 8B are cross-sectional top views of the implant device of FIG. 1A inserted into the damaged vertebrae.
Figure 8B:
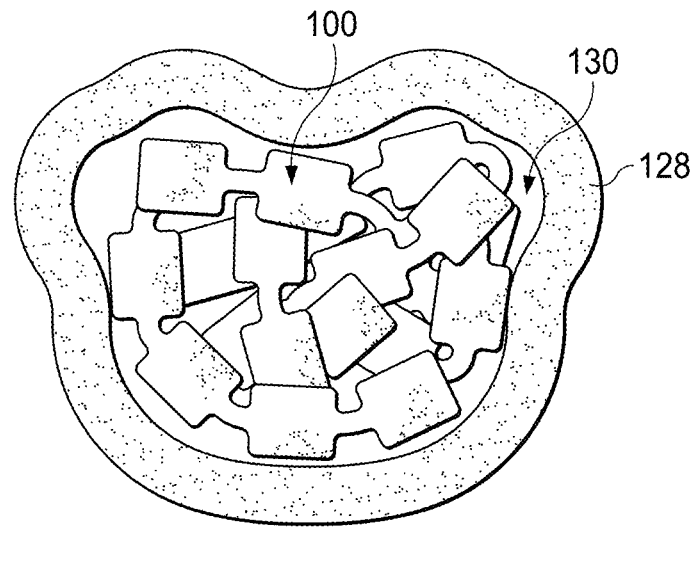

FIGS. 8A and 8B are cross-sectional top views of the implant device of FIG. 1A inserted into the damaged vertebrae of a vertebral body 128 having one or more strands 102 implanted within portion 130 of vertebral body 128. The one or more strands 102 may comprise a plurality of beads 106, which may be joined in series by one or more joints 108 portions as described above. One or more cannula 138, each having a lumen 142 of sufficient size for passing linked beads 106, can be used to implant strand 102 into vertebral body. The one or more cannula 138 may be inserted into vertebral body 128 preferably through pedicles. Cannula may be curved at the tip to direct the implant to certain locations in the body.

FIG. 9 is a flowchart of a method 200 for inserting an expandable implant into a body. The method 200 is described with reference to the spinal implant device 100 described with reference to FIGS. 1A-8, however, the method may be applicable to other devices. The method 200 includes unpackaging an assembly containing a spinal implant device 100 in the dehydrated state. In the dehydrated state, the implant device 100 is stiff. The spinal implant device 100 is then partially rehydrated by soaking the spinal implant device 100 in a saline solution (bath) for a limited period of time. In this pre-soaking stage, the implant 100 partially rehydrates and enters a partially rehydrated state. The implant 100 also swells and increases in volume while rehydrating. In the partially rehydrated state, the implant device 100 may increase in volume from the dehydrated state by at least 10%, e.g., about 5% to about 25%.

The limited period of time may be, for example, less than 10 minutes. In some methods, the limited period of time is at least 30 seconds, at least 1 minute, at least 90 seconds, at least 2 minutes, at least 2.5 minutes, at least 3 minutes, at least 3.5 minutes, at least 4 minutes, at least 4.5 minutes, or at least 5 minutes. In some methods, the limited time is about 5 seconds to about 5 minutes, about 10 seconds to about 5 minutes, about 20 seconds to about 4 minutes, about 30 seconds to about 5 minutes, about 45 seconds to about 4 minutes, about 1 minutes to about 8 minutes, about 1 minutes to about 10 minutes, about 1 minutes to about 15 minutes, about 2 minutes to about 4 minutes, about 1 minute to about 6 minutes, about 2 minutes to about 5 minutes, or about 15 seconds to about 15 minutes.

The device 100 is immediately removed from the saline bath at the expiration of the soaking time and is inserted into the body via a cannula. The device enters a cavity in the body. In the method 200, the cavity is formed in a collapsed vertebrae. In some cases, the cavity is shaped in the body prior to or during the pre-soaking stage. In some implants, the implant is impacted and interdigitated with the cancellous bone within the body without creating a cavity.

The partially hydrated device 100 enters the cavity and the joints 108 flex as the device 100 abuts walls of the cavity and/or as the user presses more of the device 100 into the cavity. The device 100 flexes via the joints to cluster the beads 106 and form an irregularly shaped mass that fills the space of the cavity. The device 100 continues to expand to the rehydrated state due to either, fluid in the cavity. At the rehydrated volume, the beads 106 provide support to the walls of the cavity and, in some cases, press on the walls (and the cancellous bone) of the cavity to expand the space of the cavity (creating a dense structural fill with macro spaces between the bodies for body fluid through flow and nutrient transfer to all beads). In the rehydrated state, the implant device 100 may increase in volume from the dehydrated state by at least 40%, (e.g., about 20% to about 70%), by at least 30%, or by at least 40%.

Figure 10:
FIGS. 10 and 11 are a view of a fabrication stage and a shaping stage of a system for manufacturing of the implant device.
Figure 11:

FIGS. 10 and 11 are a view of a fabrication stage and a shaping stage of a system 160 for manufacturing of the implant device 100. The system 160 includes a mill 162 for milling (or coring with a hole drill/hole saw type of drill) a rod 164 of a bone 166. During the fabrication stage, the system 160 mills at least one rod 164 from the bone 166 (e.g., a cortical bone or cancellous bone). The bone 166 may be a femur bone, or any other bone with a length equal to or greater than the intended rehydrated length. Some systems mill and shape multiple rods from the cortical bone into a set of monolithic strands. Each of the milled (or cored out) and shaped strands 102 have at least one bead 106. The mill 162 shapes each rod from the bone into a monolithic strand 102.

The monolithic strand 102 comprises plurality of beads 106. Each bead 106 in the plurality of beads 106 is connected by a flexible joint 108. In some systems, square blanks are machined or fabricated out of bone. The square blanks are further shaped to have rounded corners and the links are machined to have smaller cross sections than the beads. Square blanks can increase usage of the donated bone tissue.

Figure 12:
FIG. 12 is a view of the system in a demineralization stage during the manufacturing of the implant device.

FIG. 12 is a view of the system 160 in a demineralization stage during the manufacturing of the implant device 100. Demineralization is typically achieved with a variety of chemical processing techniques, including the use of an acid 168 such as hydrochloric acid, chelating agents, electrolysis, or other treatments. The demineralization treatment removes the minerals contained in the natural bone 166, leaving collagen fibers with bone growth factors including bone morphogenic protein (BMP). Both the moisture content and the mineral level of the material influence the flexibility (e.g., malleability, elasticity, pliability) of the material. In the dehydrated state, the implant 100 has a moisture content of about less than 10. In the hydrated state, the implant 100 has a moisture content of about more than 50%. In the dehydrated, (partially) demineralized state, the implant 100 in less flexible than the implant in the hydrated, demineralized state.

To demineralize the bone 166, the strand 102 is inserted into an acid bath 170 of, for example, a hydrochloric acid. In some systems, the strand is demineralized by a misting apparatus rather than an acid bath. The misting apparatus is configured to mist the strand with a demineralizing acid. In some systems, the strand is demineralized by a steamer rather than an acid bath. The steamer is configured to steam the strand with a demineralizing acid. In some strands, the demineralized layers are permeable to water.

Figure 13:
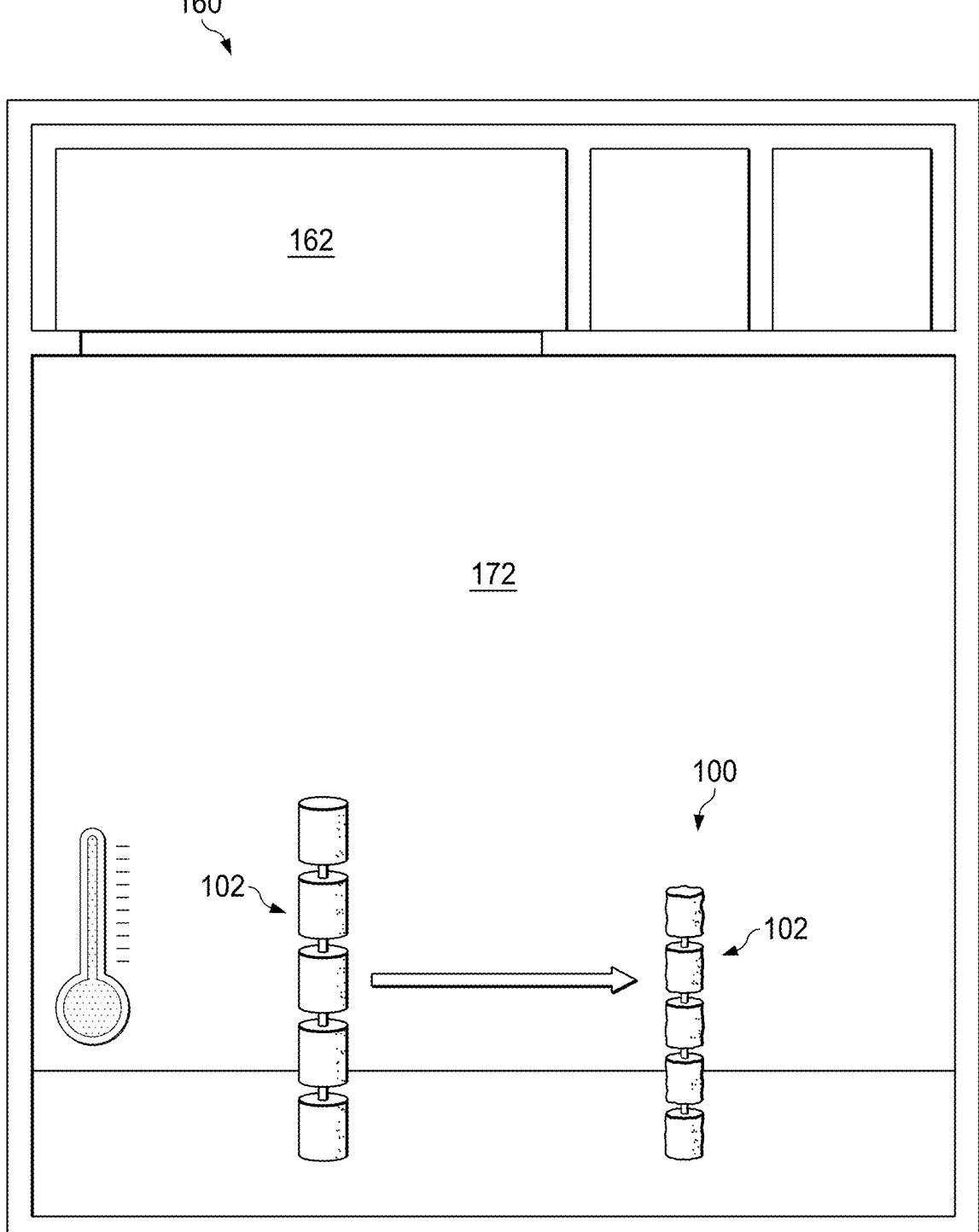
FIG. 13 is a view of the system in a dehydration stage during the manufacturing of the implant device.

FIG. 13 is a view of the system 160 in a dehydration stage during the manufacturing of the implant device 100. The system 160 includes a dehydrator 172, for example, a freeze-drying apparatus and/or an oven. The dehydrator 172 dehydrates the monolithic strand 102 by a predetermined amount. For example, the dehydrator may reduce the moisture content of the shaped strand 102 by about 5% to about 90%, for 100% example at least about 10%, at least about 20%, at least about 30%, at least about 40%, at least about 50%, at least about 50%, at least about 60%, at least about 70% at least about 80%, at least about 90%, or at least about 100%.

Additionally or alternatively, the dehydrator 172 dehydrates the monolithic strand 102 to have a predetermined volume less than the volume of the shaped monolithic strand 102 prior to demineralization and/or prior to the dehydration stage. The dehydrator 172 reduces the volume of the shaped strand 102 by about 5% to about 90%, for example, about 40%. In some systems, the dehydrator reduces the volume of the strand 102 by at least about 10%, at least about 20%, at least about 30%, at least about 40%, at least about 50%, at least about 50%, at least about 60%, at least about 70% at least about 80%, or at least about 90%.

Some systems include a packaging apparatus configured to clean, sterilize, and package the monolithic strand in a sterile packaging. In some systems, the packaging apparatus packages the strand in an assembly. The assembly can include, for example, multiple strands and/or beads, instructions for use, and accessories for use (e.g., a cannula or trocar). Some assemblies can include a double pack for delivery into the sterile field. A double pack contains an outer pack and a sterile inner pack. Inner pack to be sterile. Some assemblies and/or implants are aseptically processed, instead of or in addition to being sterilized.

Figure 14:
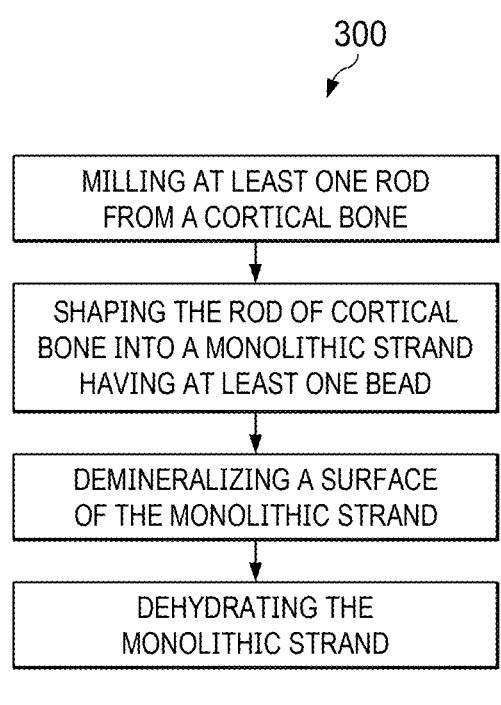
FIG. 14 is a flowchart of a method for manufacturing a spinal implant device.

FIG. 14 is a flowchart of a method 300 for manufacturing a spinal implant device. The method 300 is described with reference to the system 160 and implant 100, however, the method 300 may be performed using any applicable system or device. The method 300 includes cutting a rod from a cortical bone. The rod may be a cylindrical rod or a square blank rod. The rod is then shaped or milled to form the monolithic strand. The monolithic strand has a shaped volume that is equal to or greater than the rehydrated volume. The monolithic strand has at least one bead. The shaped strand is then demineralized for a predetermined about of time so that the inner volume of the joints is fully demineralized. The inner volume of the beads is partially demineralized, leaving a core of rigid mineralized material. After the predetermined amount of time, strand is removed from the demineralization stage and the strand is rinsed and dried. The strand is then placed in a dehydrator and dehydrated to have a volume 40% less than the volume of the shaped strand.

In some embodiments, two or more strands and/or other implants may be used in combination with each other. Multiple monolithic strands 102 may be connected end to end (in series) to form implant devices of longer length. Multiple monolithic strands 102 may also be connected at a common junction to form an implant device with a denser cluster of strands and/or to form a thick rope or tassel of expandable strands.

Further, configurations using multiple monolithic strands can use strands of different dimensions, materials, coatings, flexibilities, mineral levels, volumes, moisture contents, or other properties to customize the implant device according to the needs of the user.

While the spinal implant device 100 has been described as a monolithic strand formed by a shaped cortical bone, demineralized in a treatment, and dehydrated by a dehydrator (e.g., freeze dryer), other flexible, spinal implant devices are formed using a 3D printing systems to have precise configurations using osteoconductive materials. The implant devices formed by a 3D printer do not undergo a demineralization treatment or a dehydration treatment after shaping a strand. Rather, the 3D printed implant devices are completed and, if printed in a sterile environment, can be inserted into the body after the shaping stage. In some systems, sterilization and assembly may be performed prior to insertion of the spinal implant into the body. Implants formed using a 3D printer system can be substantially similar to the device 100, however, 3D printed implants do not require a pre-soaking step prior to insertion to increase flexibility and have an infill structure that promotes new bone growth. The 3D strand and/or chain can be made of a material in the PAEK family, for example PEEK or PEKEKK. Some strands and/or chains can be coated to enhance osteosynthesis characteristics.

Implants printed by a 3D printing system (e.g., unitary strands and/or chains) are formed using osteoconductive and/or osteoinductive materials. Osteoconductive materials or scaffolds mimic the extracellular matrix in a regenerating bone environment. Osteoconductive materials are informative to surrounding cells and provide mechanical support to the cells. Osteoconductive biomaterial can integrate with the adjacent bone and promote new tissue ingrowth (osteoconduction) and can allow colonization by the host blood vessels. Further, osteoconductive materials are biocompatible and resorbable. Various synthetic biomaterials like inorganic ceramics (e.g., hydroxyapatite, coralline-derived hydroxyapatite, tricalcium phosphate, calcium sulphates, glass ceramics, calcium phosphate-based cements, and bioglass), metals, and synthetic biodegradable polymer composites can be used as scaffolds of osteoconductive materials. The calcium-phosphate materials for the implant can include hydroxyapatite (HA), tricalcium phosphate (TCP), biphasic calcium phosphates (BCP), and bioglasses.

Additionally, osteoconductive material can include biocompatible polymers, for example polylactic acid (PLA), polyglycolic acid (PGA), poly(a-hydroxy esters), poly(ethylene glycol), polydioxanone, poly(orthoesters), polyanhydrides, polyurethanes, and poly(propylene fumarate, copolymer poly(lactic acid-co-glycolic acid) (PLGA), micro- or nanoscale HA particles, fibrin, collagen, glycosaminoglycan, fibrin, and silk. Additionally, the implant can be formed by or comprise osteoinductive synthetic biomaterials (e.g., bone morphogenetic protein (BMP) inorganic ceramics, PAEK family of materials, for example, PEEK or PEKEKK, BMP metals, and BMP synthetic biodegradable polymers). Osteoinductive materials include autografts, demineralized bone matrix (DBM) and specific bone morphogenetic proteins (BMPs). Osteoinductive materials can promote bone formation within the scaffold material (e.g., the implant) as well as outside the scaffold material (e.g., the implant).

Manufacturing flexible devices for insertion into a cavity of a body using 3D printer systems can create customized implant devices for a variety of uses and/or patient needs. For example, the flexible devices can have unique combinations of shell structures, infill structures, infill patterns, dimensions, biocompatible materials, and/or other implant device properties while maintaining a unitary strand configuration (e.g. a single piece of elongated body). In particular, the 3D printing system can produce a implant device with bone-like infill patterns and with shells that at least partially expose the bone-like infill pattern so that new bone growth can grow through the openings of the infill pattern or infill structure. In some flexible implant devices, the infill pattern may be a honey comb pattern, imitating cortical bone, or a webbed or gyroid pattern, mimicking cancellous bone.

Figure 15:
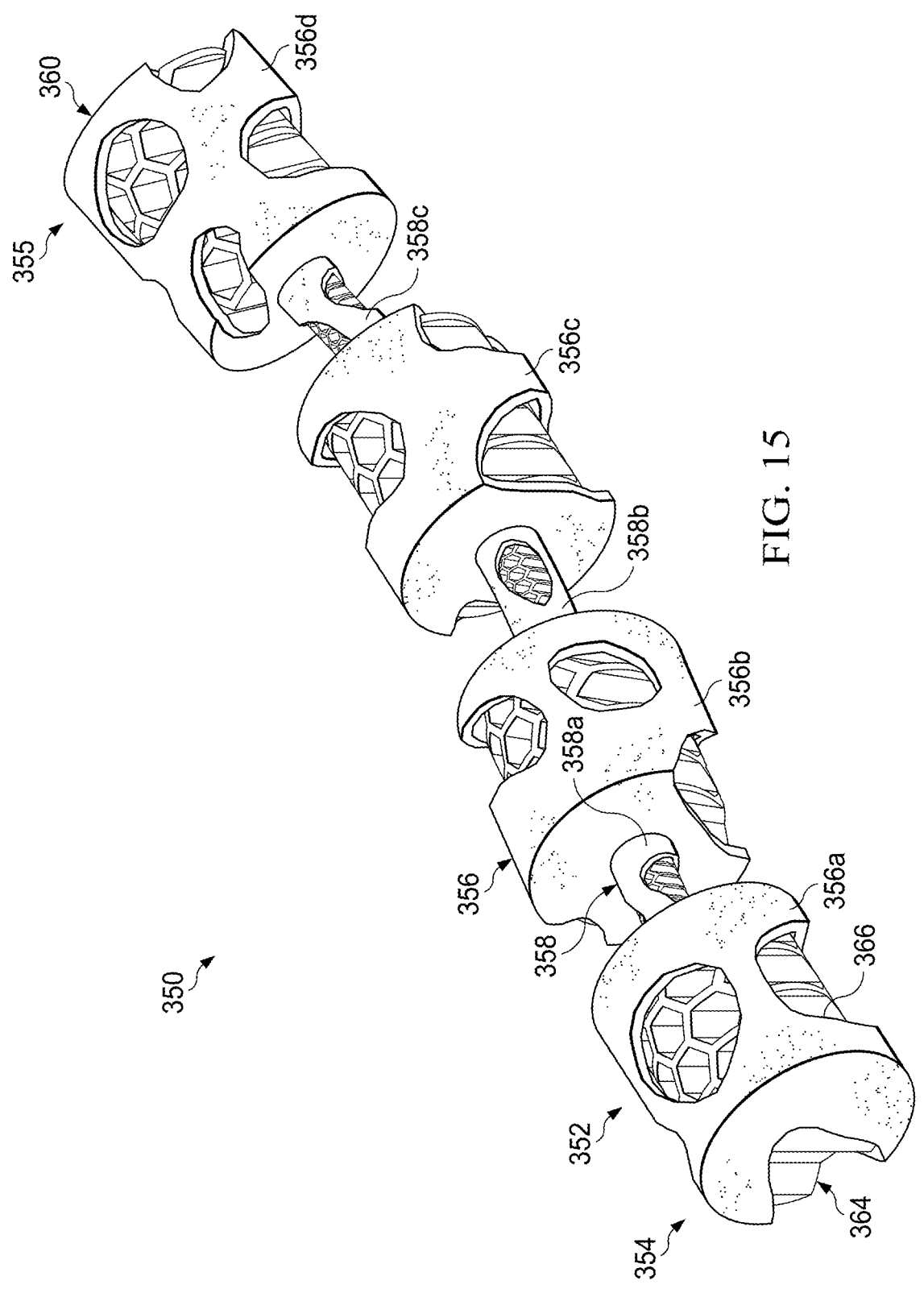
FIG. 15 is a perspective view of a spinal implant device with unitary strand formed by a 3D printing device in a single run.

FIG. 15 is a perspective view of a spinal implant device 350 with unitary strand 352 formed by a 3D printing device in a single run. The spinal implant device 350 includes the unitary strand 352 extending from a first end 354 to a second end 355. The spinal implant device 350 is formed by a single material and is extruded from a 3D printer in a single run, so as to form a unitary, elongated body. The spinal implant device 350 may have a similar shape as compared to the spinal implant device 100, however, the spinal implant device 350 may have a variety of shapes, dimensions, and connections.

The terms "height," "width," and "length" herein are distances or dimensions measured along the three perpendicular axes. For example, the first end 254 of the strand 352 and the second end 355 of the strand 352 define a length (first) axis 114, a height (second) axis 116 is perpendicular to the length axis 114, and the width (third) 118 axis is perpendicular to both the length axis 114 and the height axis 116.

The unitary strand 352 includes a series of large-diameter bodies spaced equally along the strand 352. In the device 350, the large-diameter bodies are barrels, masses, or beads of a biocompatible material. The strand 352 also includes a series of small-diameter sections arranged between adjacent barrels (beads) 356. In the device 350, the small diameter sections are flexible struts 258 (e.g., joints, beams, or connectors). The barrels 356 and struts 258 are integrally formed and are shaped from a single or continuous piece of material. In some spinal implant devices, the strand can include or be embedded (or coated) with additional biocompatible material, for example a biocompatible polymer, metal, ceramic, composite, or any combination thereof. Further, some implant devices have osteoinductive properties and/or are made at least partly from osteoinductive materials. The barrels 356 and struts 358 are uniform in shape, however, some strands many have non-uniformly shaped barrels and struts.

The barrels 356 include a first barrel 356a, a second barrel 356b, a third barrel 356c, and a fourth barrel 356d. The first and second barrels 356a, 356b are connected by a first strut 258a. The second and third barrels 356b, 356c are connected by a second strut 258b. The third and fourth barrels 356c, 356d are connected by a third strut 258c.

The strand 352 has an exterior shell 360 (exterior surface) which extends from the first end 354 to the second end 355. The exterior shell (surface) 360 defines an interior volume 362 of the strand 352. The interior volume 362 of the shell 360 has an infill structure 364 or infill pattern that mimics the structure of a bone.

Figure 16A:
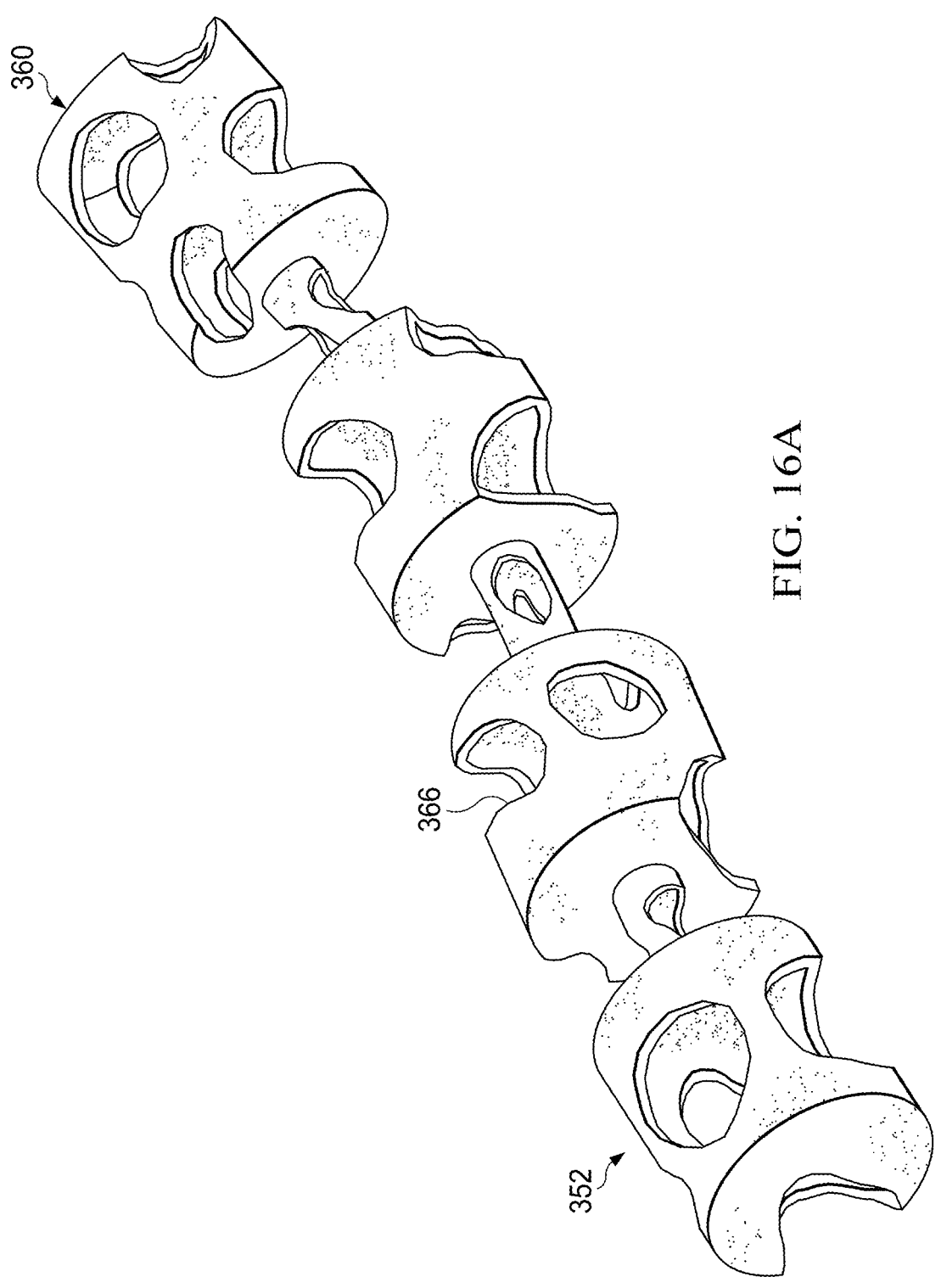
FIG. 16A is a perspective view of the exterior shell of the unitary strand without showing the infill structure.

FIG. 16A is a perspective view of the exterior shell 360 of the unitary strand 352 without showing the infill structure 364. While the infill structure 364 is not separable from the exterior shell 360, only the shell 306 is shown in FIG. 16a for simplicity of the description. The exterior shell 360 of the strand 352 also defines a plurality of openings (openings) 366 that expose a portion of the infill structure 364 arranged directly adjacent the opening 366 in the interior volume 362. In some cases, the shell is or comprises a mesh and the mesh includes the plurality of openings. The openings can provide an inlet to the infill structure for fluids, which can facilitate cell attachment to the infill structures when implanted into the body.

Figure 16B:
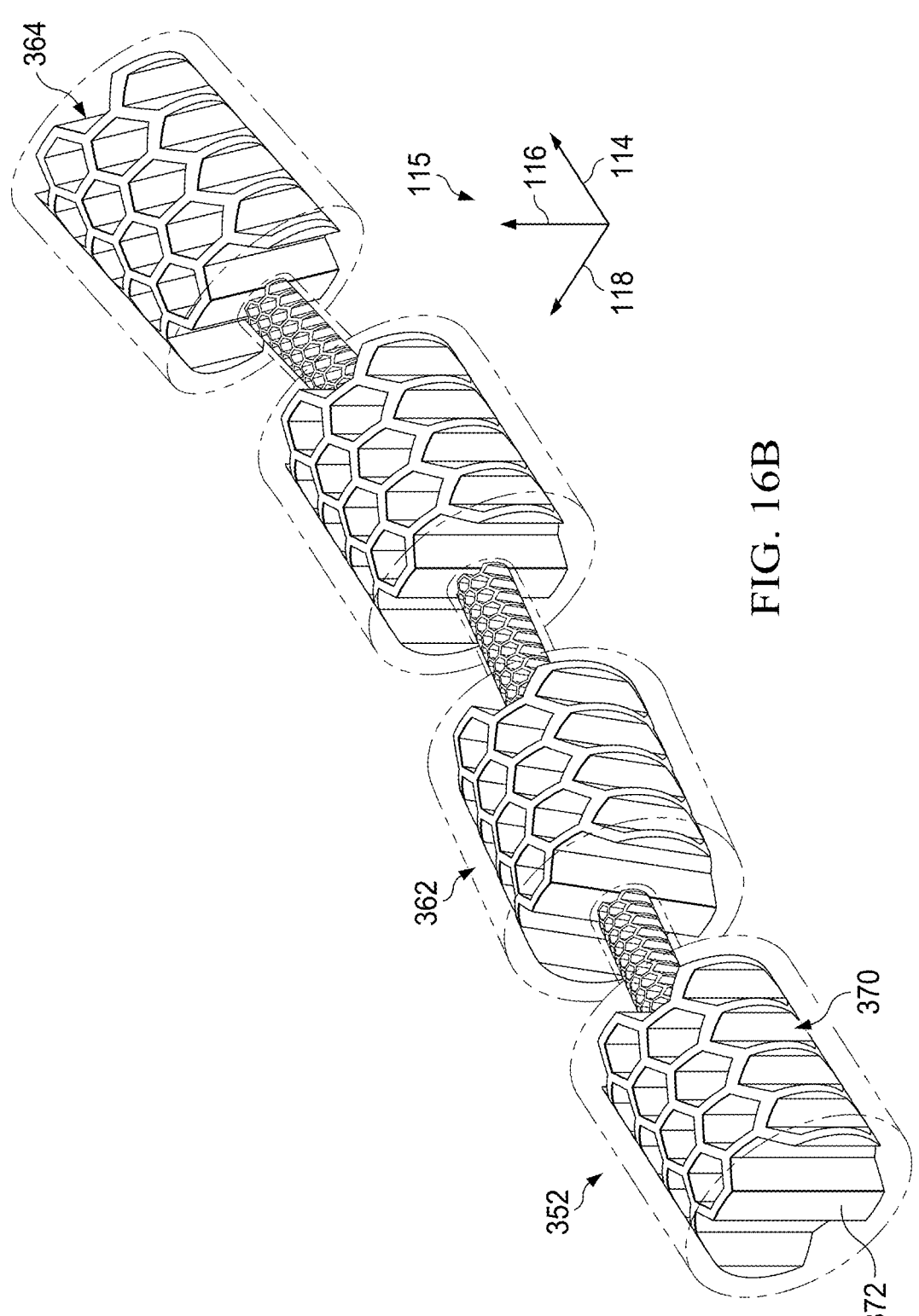
FIG. 16B is a perspective view of the interior volume defined by the shell with the infill structure.

FIG. 16B is a perspective view of the interior volume 362 defined by the shell 360 with the infill structure 364. While the infill structure 364 is not separable from the exterior shell 360, only the infill structure is shown in FIG. 16B for simplicity of the description. The boundary of the interior volume 362 is shown in dotted lines. The infill structure 364 is a honeycomb infill pattern for imitating the structure of a cortical bone. The honeycomb pattern of the infill structure 364 spans the entire interior volume in a first orientation. In this configuration, the infill structure 364 can be considered "mono-patterned" in that the structure type or pattern (honeycomb) of the infill structure 364 remains constant through the strand 352.

The honeycomb structure is a series of channels 370 defined by walls 372 and described with reference to the orientation icon 115. The channels 370 are generally aligned with the height axis 116. The strand 352 is centered on a length axis, defined by the first end 354 of the implant device 350 and the second end of the implant device 350. The height axis 114 and the length axis 114 are perpendicular relative to each other and relative to a width axis 118. In this configuration, the infill structure 364 can be considered "uniform" or "uniformly oriented" as the orientation of the channels in the infill structure are at a single, first orientation.

Some strands have interior volumes with at least two or a variety of infill structure types (e.g., honeycomb, webbed, gyroid, sinusoidal, hatched, weave, braided, linear, cortical bone, or cancellous bone). An interior volume with at least two infill structure types can be considered a "multi-patterned" infill structure. For example, the interior volume may have a multi-patterned structure in which the barrels have barrel infill pattern (e.g., honeycomb) and the struts have a strut infill pattern (e.g., gyroid), different from the barrel infill pattern.

In addition, infill structures may have patterns oriented differently. For example, the strand may have a mono-patterned infill with a honeycomb pattern. In the mono-patterned infill structure, the honeycomb openings align (i.e., are oriented) with a first axis on the and a second, non-parallel axis at the struts. Some strands may have a mono-patterned structure with an infill pattern oriented differently on one or every barrel. An interior volume with one or more patterns oriented along different, non-parallel axes can be considered a "variably oriented" infill structure. In some devices, the infill structure may be multi-patterned and uniformly oriented, multipatterned and variably oriented, mono-patterned, and uniformly oriented or mono-patterned and variably oriented. Additionally, some infill patterns, for example webs, do not have a clear orientation. In infill structures that have an infill pattern with little to no orientation or alignment with an axis, the infill structure may be a mono-patterned structure or a multi-patterned structure.

Figures 17A, 17B:
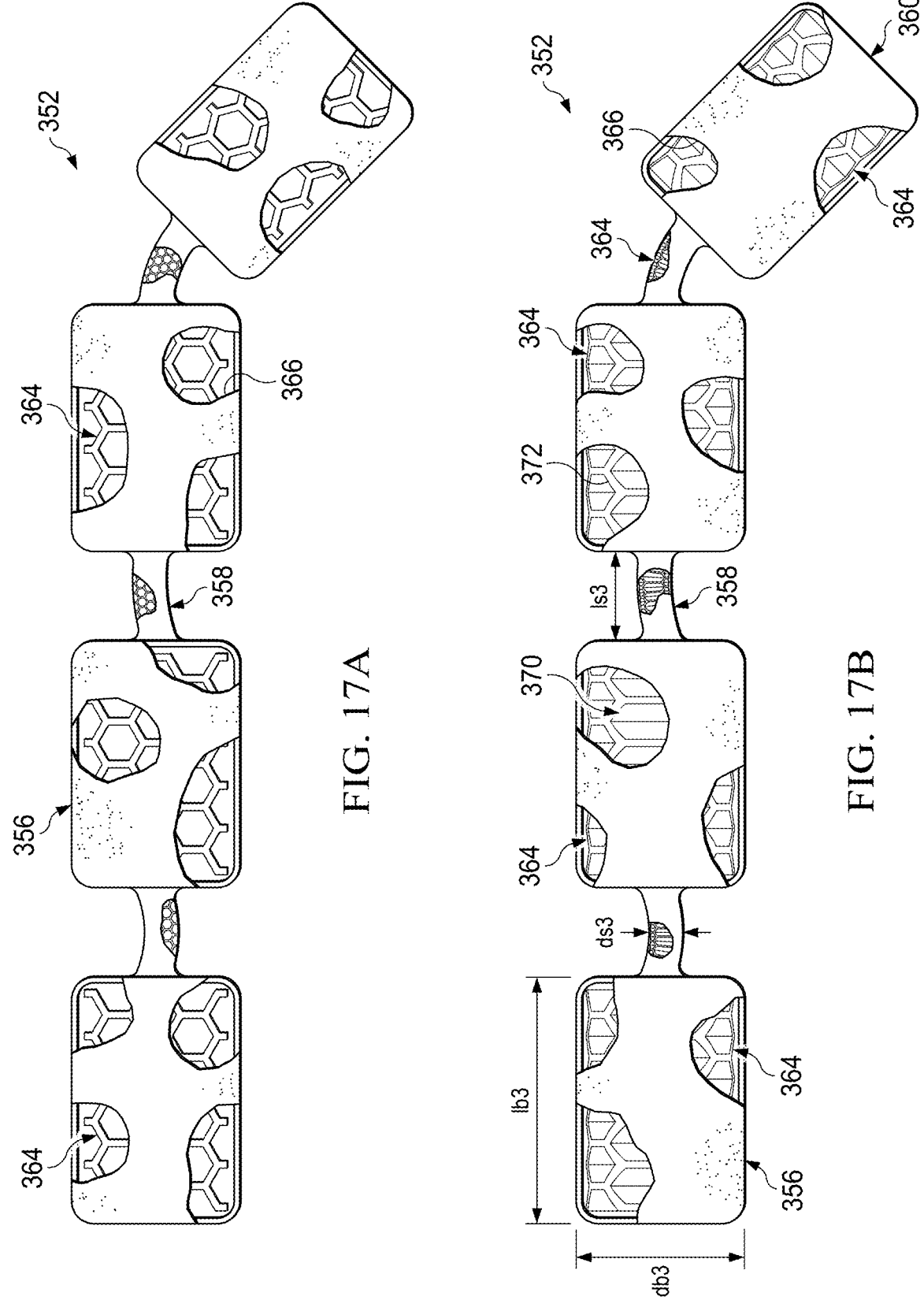
FIGS. 17A and 17B are a top view and a front view of the unitary strand of the implant device.

FIGS. 17A and 17B are a top view and a front view of the unitary strand 352 of the implant device 350. The barrels 356 and the struts 358 are formed by at least one biocompatible material. The barrels 356 have a barrel (first, second) modulus of elasticity based at least partially on, the shape, size (dimension), and/or the material(s) of the barrel 356. The struts 358 have a strut (third) modulus of elasticity, based at least partially on the shape, size (dimension), and/or the material(s) strut 358. In the device 350, the strut modulus of elasticity is less than the barrel modulus of elasticity. In some cases, each barrel has a modulus of elasticity, and each strut has a modulus of elasticity. Each of the barrel modulus of elasticities are greater than each of the strut modulus of elasticities.

The struts 358 have an increased flexibility as compared to the barrels 356. In this configuration, the struts 358 flex, condense, or compress when a force is exerted on the implant device 350. When acted upon by a force, the struts 358 flex and move the barrels 356 closer together, forming a cluster or mass of barrels 356. The mass of barrels 356 is capable of supporting internal bodily structures, such as a collapsed vertebrae of a spine. The dense mass of barrels 356, can support collapsed structures in a body, and, in some cases, press the collapsed structure into a healing position.

Each barrel 356a-d of the plurality of barrels 356 has a diameter db3 and a length lb3. In the implant device 350, length lb3 is about equal for each of the barrels 356a-d. Each strut 108a-c of the at least one strut 108 has a diameter ds3 and the length ls3. In the implant device 350 the strut length ls3 is about equal for each strut 108a-c. In some implant devices, the struts can have a variety of lengths different from each other.

In some strands, the barrel length is at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm, greater than 0.5 mm, greater than about 5 mm. In some cases, the barrels have a length proportional to the barrel length. For example, the barrel length may be about 10% about 20% about 25% about 30 % about 33% about 40% about 50% about 60%, about 66%, about 70% about 75% about 80%, about 90%, about 110% about 120% about 125% about 130 % about 133% about 140% about 150% about 160%, about 166%, about 170% about 175% about 180%, about 190%, about 200% about 250%, about 300%, about 400%, about 500%, about 600%, about 700%, about 750%, about 800%, or about 900% of the barrel length. In some cases, the barrel diameter is proportional to the strut diameter.

In some strands, the strut length is at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm, greater than 0.5 mm, greater than about 5 mm. In some cases, the struts have a length proportional to the barrel length. For example, the strut length may be about 10% about 20% about 25% about 30 % about 33% about 40% about 50% about 60%, about 66%, about 70% about 75% about 80%, about 90%, about 110% about 120% about 125% about 130 % about 133% about 140% about 150% about 160%, about 166%, about 170% about 175% about 180%, about 190%, about 200% about 250%, about 300%, about 400%, about 500%, about 600%, about 700%, about 750%, about 800%, or about 900% of the barrel length. In some cases, the strut diameter is proportional to the barrel diameter.

Figure 18A:
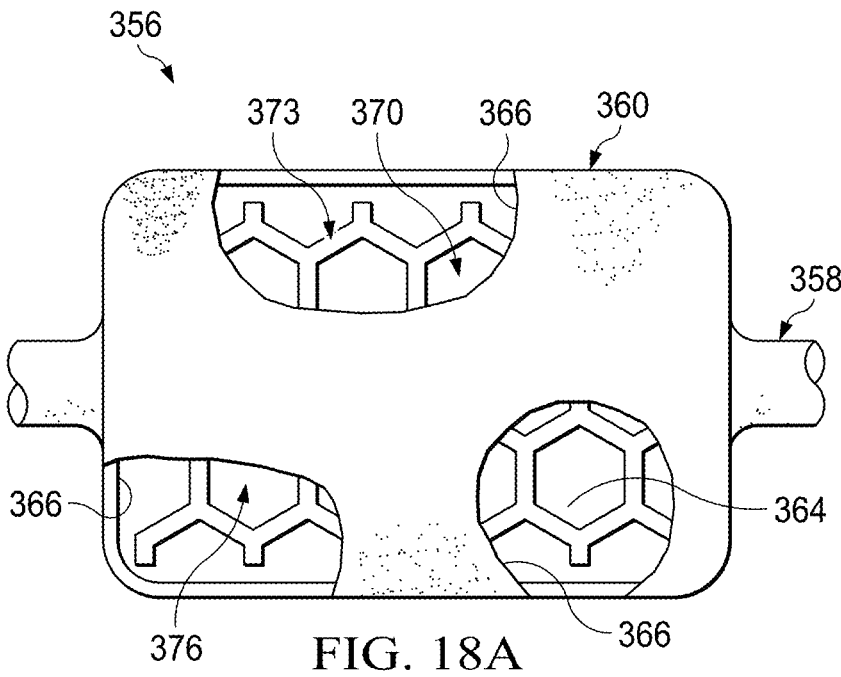
FIGS. 18A and 18B are close-up top and side views of a barrel of the strand.
Figure 18B:
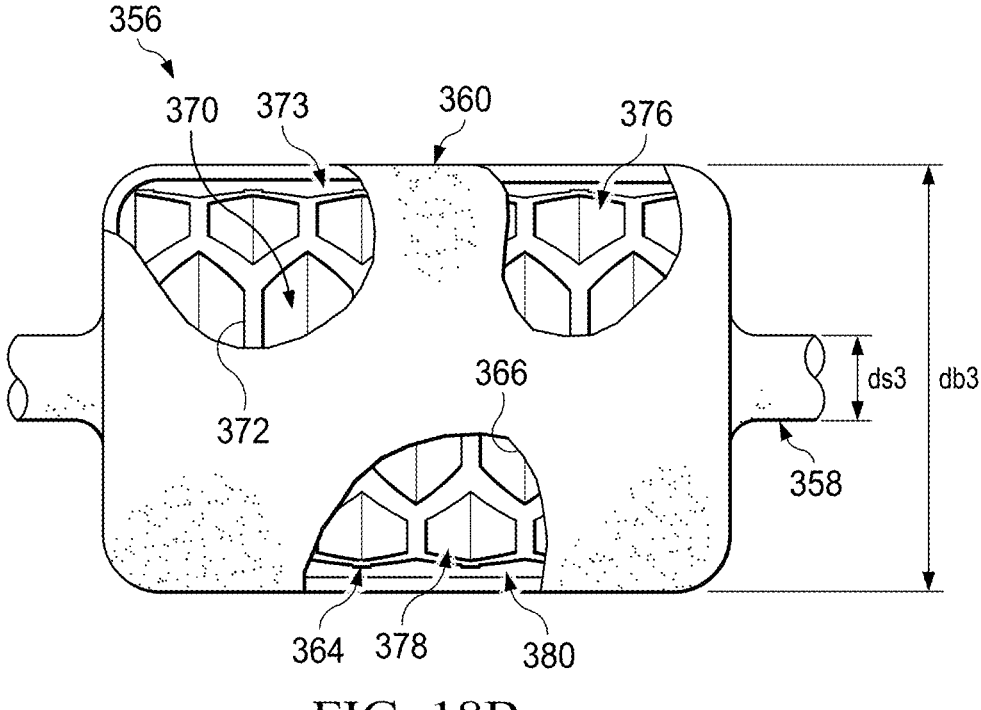

FIGS. 18A and 18B are close-up top and side views of the barrel 356 of the strand 352. The openings 366 of the plurality of openings expose a portion of the infill structure 364 arranged adjacent or beneath the exterior shell 360. Openings at a top (first end) 373 of the barrel 356 expose inlets (first openings, first apertures, first faces) 376 of the channel 370 defined by the walls 372. The channels 370 extend from the inlet at the top of the strand, to an outlet (second openings, second apertures, second faces) 378 at a bottom (second, opposite) end 380 of the strand. The walls 372 extend from the inlets 376 to the outlets 378. The openings 366 can form access points for osteointegration and/or postcondition. The channels 370 and/or the openings 366 are sized to receive new bone growths and can form a scaffold for the new bone growth. In the folded position, the spaces between beads define channels for fluid transporting bone growth cells of the patent for improved osteogenesis.

Figures 19A, 19B:
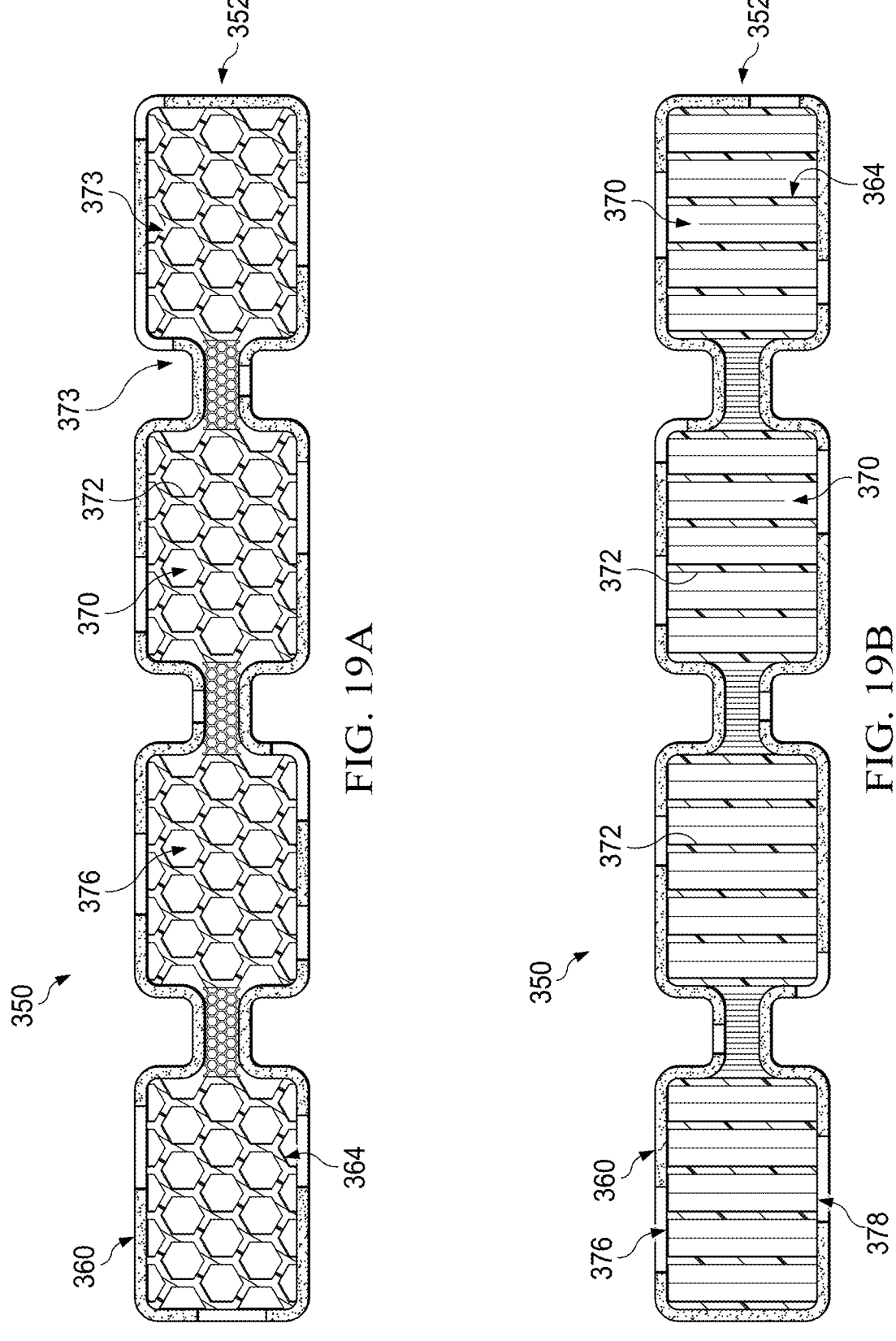
FIGS. 19A and 19B are cross-sectional top and side views of the strand.

FIGS. 19A and 19B are cross-sectional top and side views of the strand 352. The strand 352 has a linear length l3 measured from the first end 354 to the second end 355 may be made as long as practical for a particular application. For implantation into a bone may be about 30 mm to about 60 mm in length (e.g., about 10 mm to about 150 mm).

Some strands may have a linear length of less than about 1 mm, between about 1 mm and about 350 mm, at least 1 mm, at least 5 mm, at least 10 mm, at least 20 mm, at least 25 mm, at least 30 mm, at least 40 mm, at least 50 mm, at least 75 mm at least 350 mm, at least 150 mm, at least 200 mm, at least 250 mm, at least 300 mm, at least 3150 mm, at least 400 mm, at least 450 mm, at least 5 cm, at least 5.5 cm, at least 6 cm, at least 6.5 cm, at least 7 cm, at least 7.5 cm, at least 8 cm, at least 8.5 cm, at least 9 cm, at least 9.5 cm, or at least 10 cm.

Figure 20:
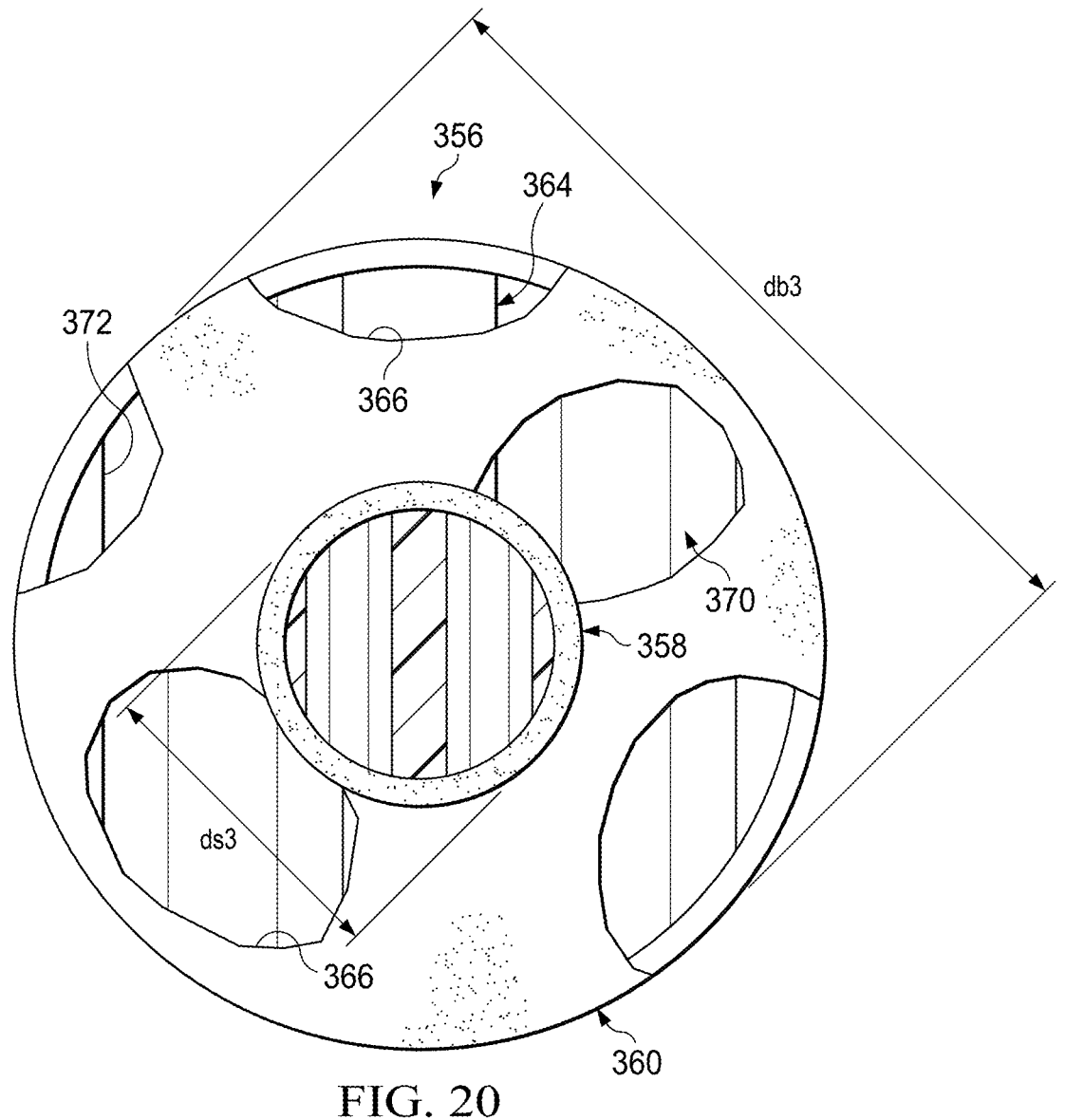
FIG. 20 is a cross sectional view of the strand taken along the length ls3 of a strut on the length axis.

FIG. 20 is a cross sectional view of the strand 253 taken along the length ls3 of a strut 358 on the length axis 114. The infill structure 264 extends through the length ls3. The openings 366 also can extend to any part of the exterior surface. In the strand 253, some openings are arranged both on the struts 258 and all faces of the barrel 356. The strut 358 and barrel 356 are centered on the axis. In some cases, at least one strut is arranged on an axis parallel to but distanced from the length axis 114 on which the barrel 356 is centered. In this configuration, the strut is arranged off center relative to the barrel. In some cases, an edge of the strut connects to an edge of the barrel so that the connection between the strut and the barrel forms a hinge. In some cases, the struts include a living hinge or weakened portion to increase the flexibility of the strut.

Each barrel 356*a-d* of the plurality of barrels 356 has a diameter db3 and the length lb3. In the implant device 350, the barrel diameter db3 is about equal for each barrel 356*a-d*. The barrel diameter db3 is about 1 mm to about 15 mm, for example, about 2 mm to about 8 mm, or about 4 mm to about 6 mm. The barrels 356 have a generally cylindrical shape and have a generally circular cross-sectional area taken parallel to the height axis 116. The barrel diameter db3 defines both the width and the height dimensions of the barrels 356. In some implant devices, the barrels can have a variety of diameters different from each other. In some implant devices, the barrels can have a variety of lengths different from each other.

Each strut 108*a-c* of the at least one strut 108 has a diameter ds3 and the length ls3. In the implant device 350 the strut diameter db3 and strut length ls3 are about equal for each strut 108*a-c*. In some implant devices, the struts can have a variety of diameters different from each other and/or a variety of lengths different from each other.

In some strands, the barrel diameter db3 is about 0.5 mm to about 50 mm, for example, about 1 mm to about 25 mm, about 4 mm to about 10 mm, about 5 mm to about 40 mm, about 2 mm to about 15 mm, about 1 mm to about 8 mm, about 0.5 mm to about 5, bout 2 mm to about 6 mm, about 3 mm to about 5 mm, about 1 mm to about 4 mm, or about 2 mm to about 4 mm.

In some strands, the barrels are geometrically shaped so that the height and width are equal, but the cross section of the barrel is not circular (e.g., a square, hexagon, octagon, etc.). In some strands, the barrels are geometrically shaped so that the height and width are different (e.g., triangle, pentagon, heptagon, etc.). In some cases, the barrel is an irregular 3-D shape.

Regardless of the geometric shape or cross-sectional area of barrels and struts, each strut has a smaller cross-sectional area (or average cross-sectional area) than the cross-sectional area (or average cross-sectional area) of the adjacent or flanking barrels. An average cross-sectional area of a barrel or strut may be taken along the length axis in a plane formed by or parallel to the plane formed by the intersection of the width axis and the height axis.

Some strands have a strut diameter ds3 of about 0.5 mm to about 8 mm, for example, about 0.8 mm to about 4 mm. The length ds3 of the struts 108 is about 0.5 mm to about 15 mm, for example, about 0.5 mm to about 5.0 mm, about 1.5 mm to 3.5 mm, about 6 mm and about 10 mm. In some cases, the strut diameter is at least about 5 mm, at least about 0.5 mm, at least about 1 mm, at least about 1.5 mm, at least about 2 mm, at least about 3 mm, at least about 3.5 mm, at least about 4 mm, at least about 4.5 mm, and/or at least about 5 mm. In some cases, the struts have a diameter proportional to the barrel diameter. For example, the strut diameter may be about 10% about 20% about 25% about 20 % about 22% about 40% about 50% about 60% about 66%, about 70% about 75% about 80% or about 90% of the barrel. In some cases, the strut diameter is proportional to the barrel diameter.

Figure 21A:
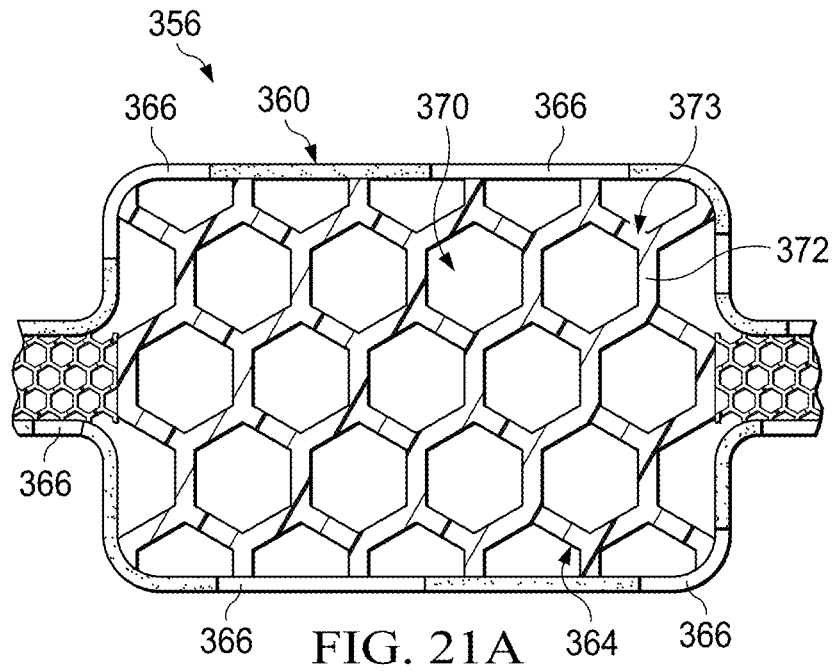
FIGS. 21A and 21B are cross sectional top and side views of the barrel.
Figure 21B:
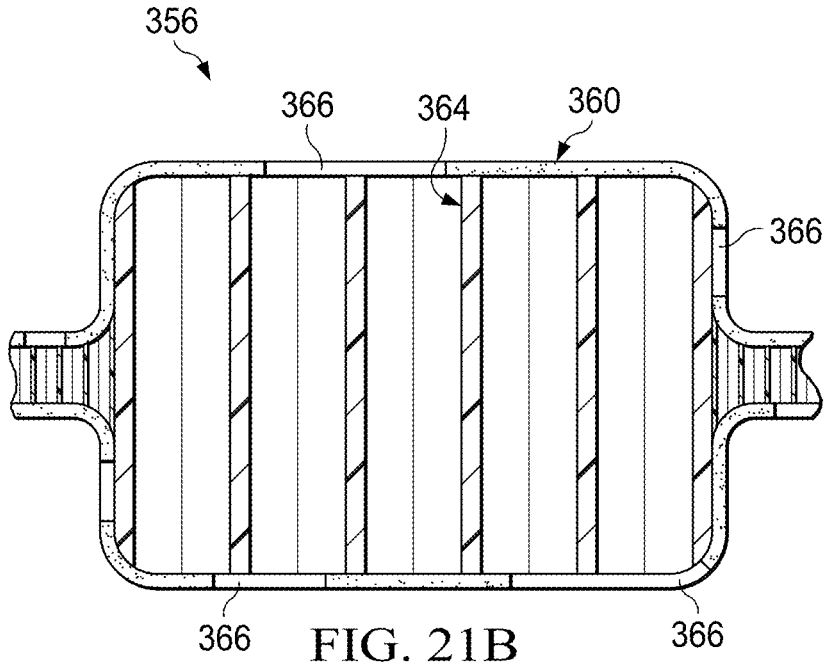

FIGS. 21A and 21B are cross sectional top and side views of the barrel 256. The barrel 256 honeycomb pattern is consistent from the first end 354 to the second end 355 of the device. In some interior volumes, the infill structure or pattern may be oriented differently between the barrels. With reference to the orientation icon 115, the honeycomb pattern forms channels that aligns with the height axis 116. In some strands, the channels of the honey comb infill pattern of the infill structure are oriented along the length axis 114 and/or the width axis in a uniformly oriented or a variably oriented infill structure. While the infill structure 366 is a uniformly oriented infill structure, some infill structures with honeycomb infill pattens may be variably oriented infill structures.

The infill structure 364 is, includes, and/or defines a honeycomb (pattern) structure, however, other, or adjacent infill structures may be, include, and/or define a webbed (pattern) structure or a gyroid (pattern) structure. Some infill structures have multiple infill patterns arranged at different areas of the internal volume. For example, the infill structure can form a patchwork of multiple infill patterns or can simulate the pattern of a natural bone.

Figure 22:
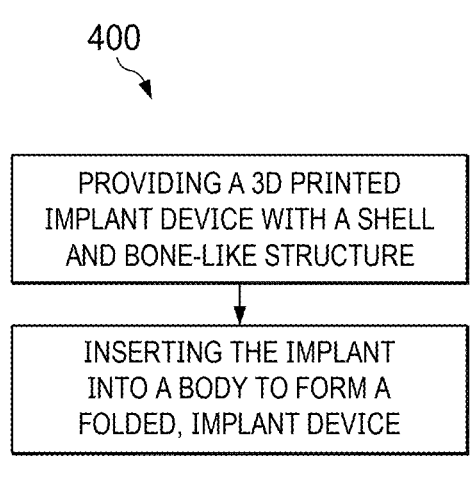
FIG. 22 is a flowchart of a method of use for inserting a flexible or foldable spinal implant into a cavity of a body.

FIG. 22 is a flowchart of a method 400 of use for inserting a flexible or foldable spinal implant into a cavity of a body. The method 400 is described with reference to the spinal implant device 350, however, the method can be used with any applicable device or system. The method 400 is substantially similar to the method 200, however, the method 400 does not include a presoaking step and the implant device inserted is an 3D printed implant device with a bone-like infill structure.

The method 400 includes unpackaging an assembly containing a spinal implant device 100 in the printed state. In the printed state, the implant device 350 is flexible and includes a unitary strand formed by a single body of material or materials. The unitary strand includes barrels and struts integrally formed or joined with the barrels. The unitary strand also includes a bone-like infill structure with a bone-like infill pattern (e.g., a honeycomb pattern or gyroid pattern). The infill structure is encompassed by an exterior mesh, or exterior shell. The exterior shell or mesh includes a plurality of openings which expose the infill structure where the openings align with the infill structure. The openings and the infill structures are shaped to receive and promote bone growth when inserted into a body. In some strands, the infill structure and the exterior shell are integrally formed.

The struts and the barrels are centered along a first axis. The implant is removed from the package and can be inserted into the body without a pre-soaking stage. The first end of the spinal implant device is then inserted and fed through a cannula. The cannula discharges the first end of the spinal implant device into a prepared or unprepared cavity of the body. The cavity is defined in or adjacent to a collapsed bodily structure (e.g., a vertebrae). The first end of the implant device extends into the cavity until the first end abuts a wall of the cavity. The wall of the cavity provides a force against the first end of the implant device and a conveying force on the second end of the implant device applies a pressing force to the implant device. Under one or both forces, the struts of the implant device flex, compress, or condense so that the entire strand enters the cavity. The strand continues to compress and form a dense mass or cluster until the entire, or apart of, the strand is inserted into the cavity. The barrels are arranged close together in the clustered formation and support the collapsed structure of the body by pressing outwardly on the walls of the cavity.

Figure 23:
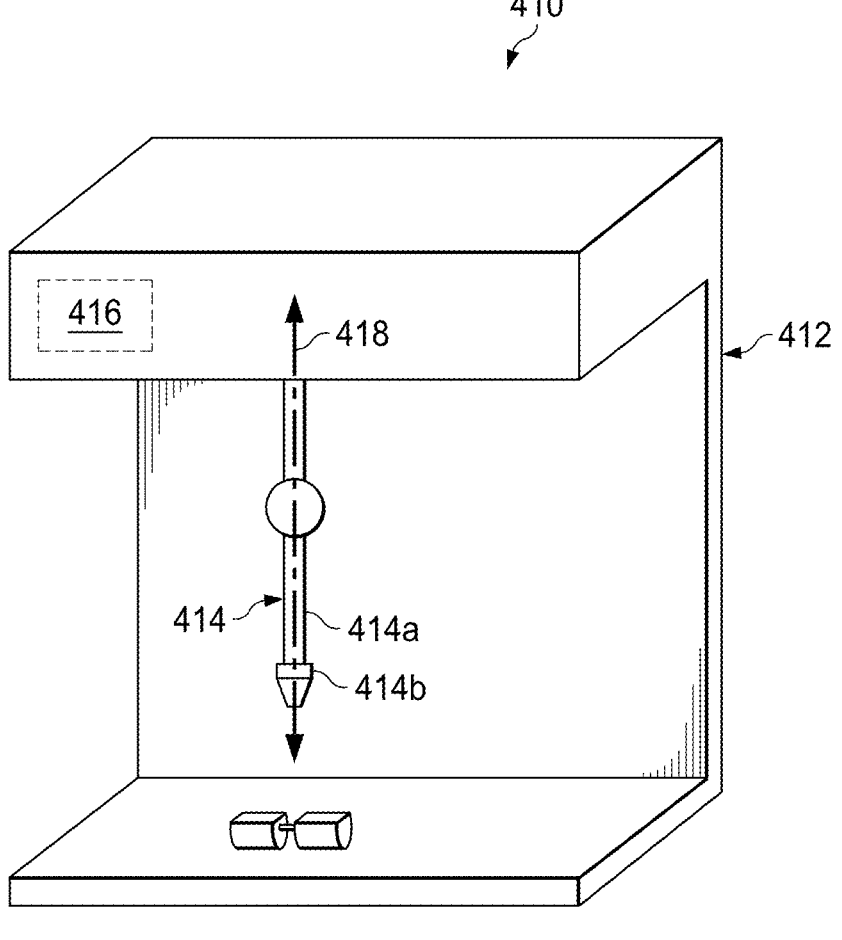
FIG. 23 is a view of a 3D printing system for forming a unitary implant device with a bone-like infill structure.

FIG. 23 is a view of a 3D printing system 410 for forming a unitary implant device with a bone-like infill structure. The system 410 include a 3D printer 412 with an extrusion arm 414 and a computer subsystem 416. The extrusion arm 414 includes an elongated arm 414*a* and extrusion nib 414*b*. The extrusion arm 414*a* and extrusion nib 414*b* form an extrusion axis 418. The extrusion nib 414*b* is configured or operable to extrude at least one biocompatible material to form the exterior shell and infill of the unitary strand. In use, the system 410 extrudes the device 250 from the bottom end to the top end of the implant device 350. In some cases, the system extrudes the implant device 250 from the first end of the second end. The system can extrude or print the unitary strand so that the length axis 114 is angled or perpendicular to the extrusion axis 418. Additionally, or alternative, the system can extrude ort print the unitary strand so that the length axis is aligned with or parallel to the extrusion axis.

The system forms a first portion of the unitary strand such that the first portion of the unitary strand includes a shell extending from a closed bottom end to an open top end. The open top end may be oriented towards the nib so that the extrusion nip can extrude material into or on the open end of the strand. The system may also form a second portion of the unitary strand on the first portion of the unitary strand. The second portion of the unitary strand extends from an open end to a close top end, thereby forming the unitary strand with the shell and infill structure. The infill structure may be a bone-like infill structure with a bone-like pattern, such as a honeycomb pattern and/or a gyroid pattern. The first portion can be a half of the total unitary strand and the second portion is the remaining half of the total unitary strand. The first portion can include at least one printed barrel (e.g., one, two, three, four, five, six, seven, eight, nine, ten, twenty, fifty, one hundred printed barrels barrels). The second portion can include at least one printed barrel (e.g., one, two, three, four, five, six, seven, eight, nine, ten, twenty, fifty, one hundred printed barrels barrels). In some cases, the first portion includes a first partially formed barrel having a partially formed shell and/or a partially formed infill structure, a second partially formed barrel having a partially formed shell and/or a partially formed infill structure, and a partially formed strut having a partially formed shell and/or a partially formed infill structure.

Figure 24:
FIG. 24 is a flowchart of a method of manufacturing a unitary, spinal implant device using a 3-D printer system.

FIG. 24 is a flowchart of a method 450 of manufacturing a unitary, spinal implant device using a 3-D printer system. The method is described with reference to the 3D printing system 410 and the implant device 350, however, the method 450 may be used with an applicable system or device. The method includes determining a shell structure, dimensions, an infill structure, and an infill pattern of an implant device. The 3D printer of the 3D printer system extrudes the shell of a unitary strand of an implant device to form of a first portion of the implant. The printer may extrude PEEK or PEKK to form the first portion of the implant device.

The shell of the first (half) portion forms an exterior surface of the implant. The shell defines a first interior volume of the first (half) portion of the implant. An infill structure with a bone-like pattern may be extruded in conjunction with the extrusion of the shell, each extrusion layer including a layer of shell and layer of infill structure. In some implants, the chain is extruded by forming a first (half) potion of the shell, then infilling the shell with the infill structure. The bone-like infill pattern may be a honeycomb pattern and/or a gyroid pattern. The first portion of the shell is extruded along a length axis of the shell. The length axis of the implant is perpendicular to the extrusion axis of the extrusion system. In some methods, the length axis is parallel to the extrusion axis. The first portion may be a first half of the implant device. The method can include implanting, embedding, or placing a marker or other biocompatible material in the open end of the first portion of the implant device.

The method also includes forming, extruding, or printing the second portion of the implant device on the first portion so that the first portion and second portion seal together to form a unitary strand (e.g., a unitary elongated body). Extruding the second portion includes printing an interior volume and/or an infill structure on the open end of the first portion. The infill structure of the second portion is aligned with the infill portion of the first portion so that any channels in the first portion seamless connect to channels in the second portion. The shell of the second portion is extruded onto the infill portion of the second portion and/or is extruded with the infill portion of the second portion, thereby forming a closed end of the second portion. In some systems, the entire interior volume of the implant device is portioned in the first portion and the second portion is a shell of the second portion printed onto the interior volume and the shell of the first portion.

In some systems, the unitary strand is printed in a series of layers of the shell and the infill portion. In such a system, the method includes layering material to form set of cross-sectional layers of an implant device. The cross-sectional layers include a shell layer and an infill structure layer encompassed or surrounded by the shell layer. The cross-sectional layers combine to form a set of layers. The set of layers can form a barrel, a strut, and/or a unitary strand. The set of layers may form a first portion. Another set of layers may form a second portion. The first and second portion can be connected to form at least part of the unitary strand of the device.

Figure 25:
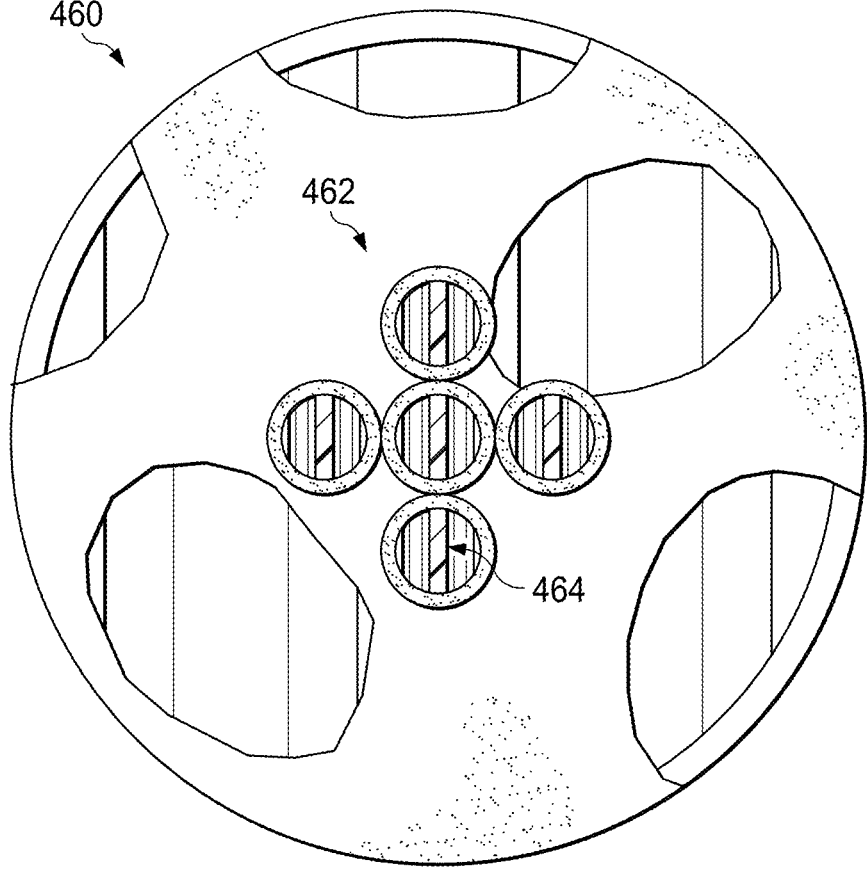
FIG. 25 is front view of a unitary strand of the spinal implant device formed by a 3-D printer system with a multi-filament joint.

FIG. 25 is front view of a unitary strand 460 of the spinal implant device 350 formed by a 3-D printer system with a multi-filament joint 462. The unitary strand 460 is substantially similar to the unitary strand 352, however, the unitary strand 460 includes the multifilament joint 461 rather than the strut 358. The multi-filament joint 462 includes a set of filaments 464 (e.g., at least two filaments) arranged pattern. The multi-filament joint 462 includes five filaments arranged in a cross pattern. Some multifilament joints have more or less than five filaments and/or form different patterns. The multi-filament configuration can have dimensions that correspond to material stiffness. The at least two filaments can have a diameter of about 1 mm to about 60 mm.

Figure 26A:
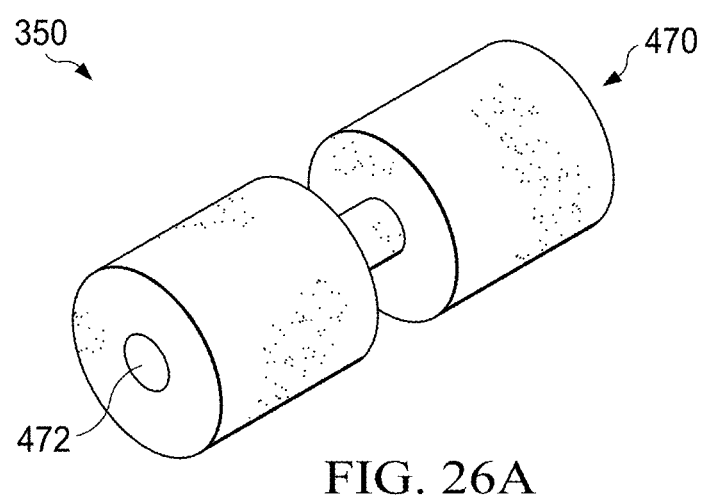
FIGS. 26A-C are views of a unitary strand of an implant device with radio-opaque markers.
Figure 26B:
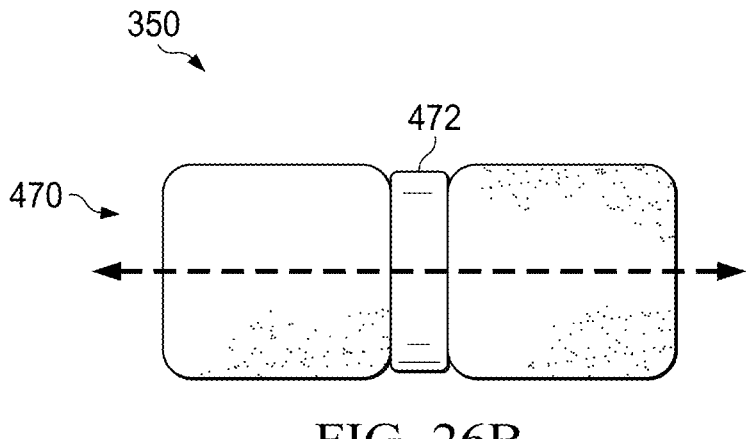
Figure 26C:
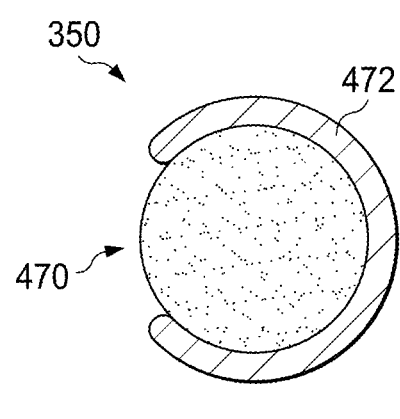

FIGS. 26A-C are views of a unitary strand 470 of an implant device 350 with radio-opaque markers 472. The unitary strand 470 is substantially similar to the unitary strand 352, however the unitary strand 470 includes markers 472 arranged in the interior volume 362 of the unitary strand 470. The radio-opaque markers 472 embedded in the interior body of the strand 470 are impermeable to x-ray waves and are visible in x-ray images.

The embedded markers 472 can include a barrel marker embedded in the barrel 356 (e.g., first marker, second marker) and a strut marker embedded in the strut 358. The markers may be a tantalum sphere, a tantalum pin, a ligating clip, and/or omnipek. In some cases, the marker is a material distributed in the biocompatible material that forms the unitary strand.

Figure 27:
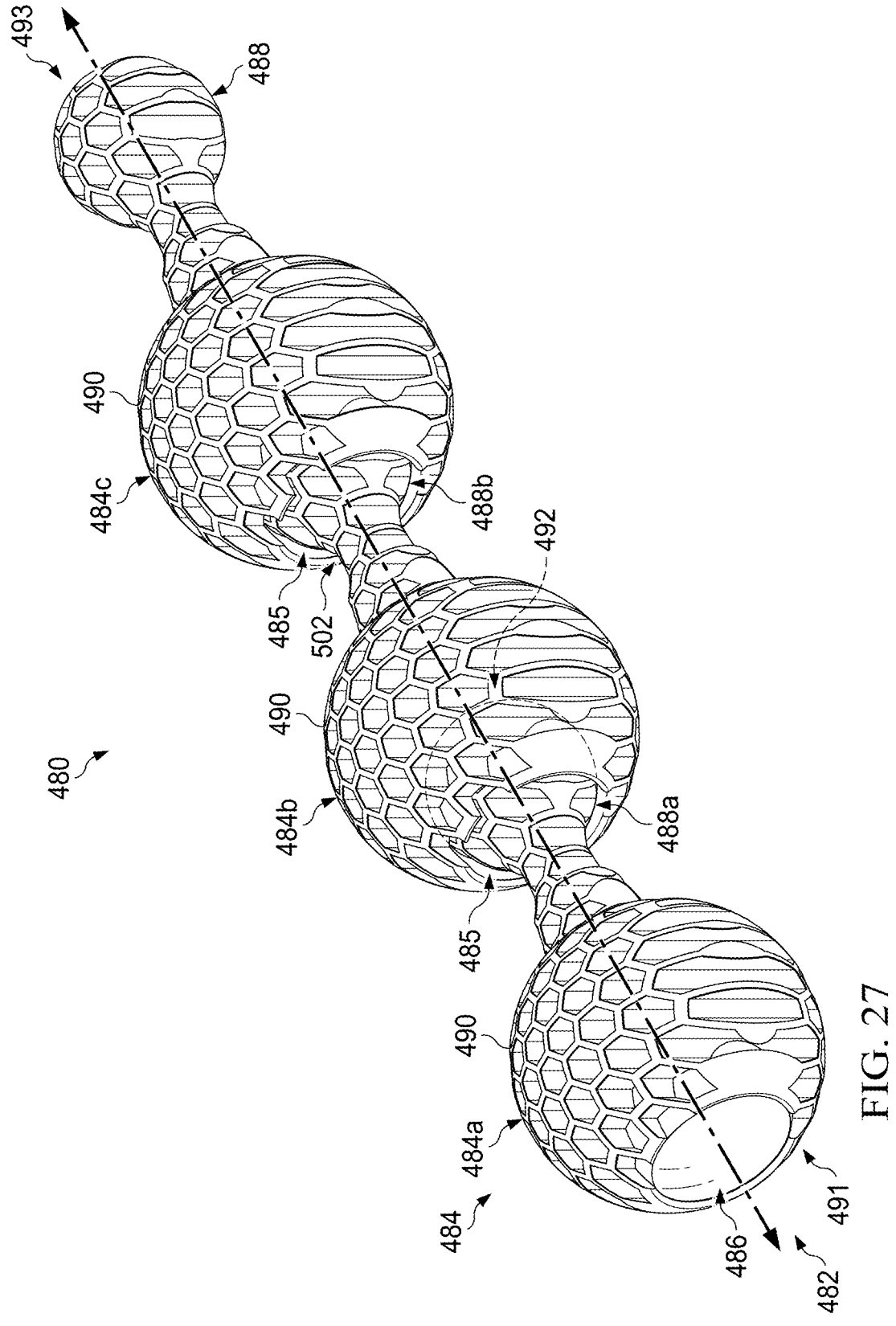
FIGS. 27 and 28 are perspective views of a 3-D printed spinal implant device with a chain formed by connected links in the straightened position and folded position, respectively.
Figure 28:
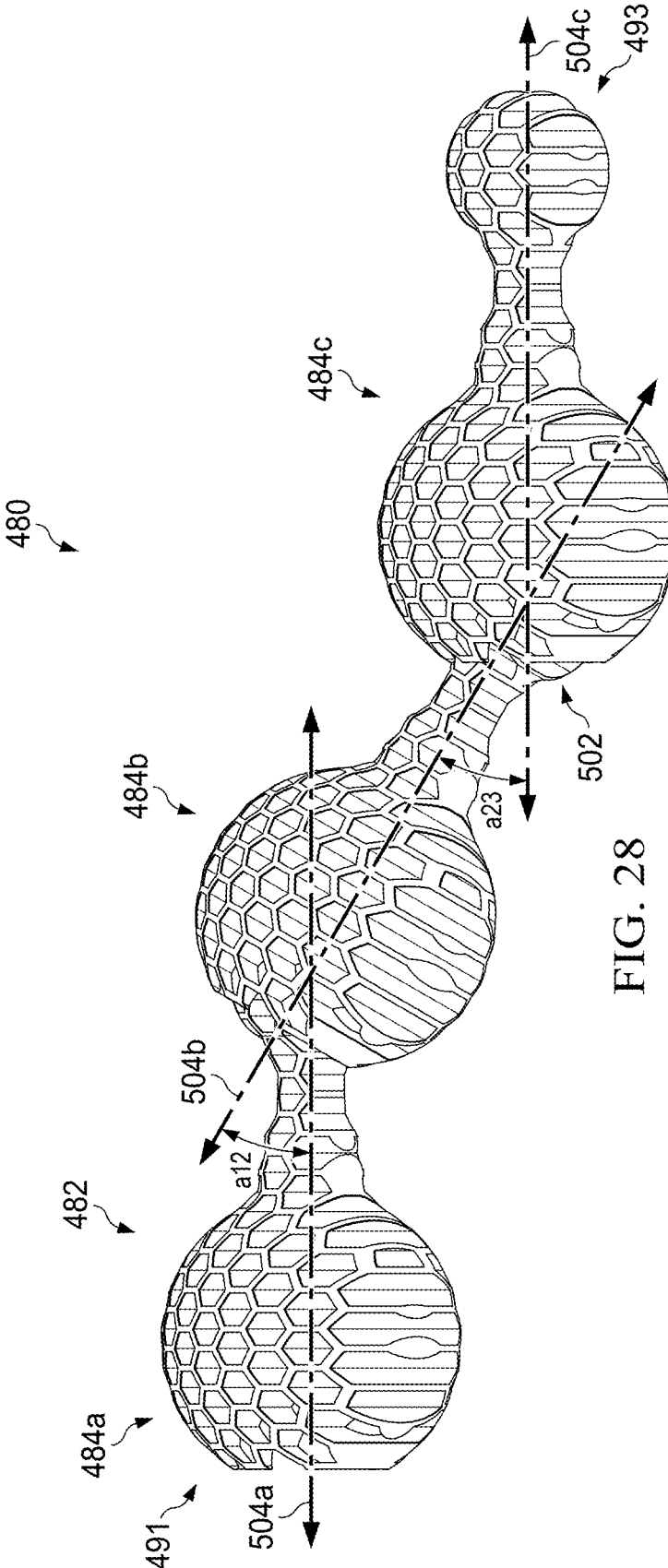

FIGS. 27 and 28 are perspective views of a 3-D printed spinal implant device 480 of a chain 482 formed by connected links 484 in the straightened position and folded position, respectively. The spinal implant device 480 is substantially similar to the spinal implant device 350, however, the spinal implant device 480 is a series of engaged links 484 rather than an elongated body. Additionally, each link 484 forming the chain 492 has an (link) external surface and a (link) interior volume whereas the implant device 350 has a unitary external shell and a unitary interior volume. Further, the spinal implant device 480 folds by rotating the links 484 relative to each other at a connection 485 between the links 484, whereas the spinal implant device 250 folds due to the flexibility or elasticity of the struts 358.

At the connection 485, attachment structures of each link 482 form a rotatable connection 485. For example, the chain 482 uses a ball-and-socket attachment structure. Some chains use other attachments structures, for example, disc-and-sockets, other insert-and-sockets, magnetic connections, sliders-slots, toothed ratchets, clutches, and/or hinges. Some chains use a plurality of links with different attachment structures.

The chain 482 extends from a first end 491 to a second end 492. The spinal implant device 480 is formed by a plurality of connected links 484. Each link 484 is extruded from a 3D printer in at least one run, so as to form a connected chain 482 or to form individual links 484 that can be connected after printing. The links 484 are made of rigid material, for example, titanium, however, other links may be made of another rigid biocompatible material or flexible biocompatible material, for example PEEK or PEKK.

The foldable, flexible chain 482 includes a series of large-diameter bodies spaced equally along the chain 482. The large-diameter bodies are first connectors configured to connect the link to another. In the device 480, the first connector or large-diameter body is a socket 486 formed by of a biocompatible material using a 3D printer. The chain 482 also includes a series of small-diameter sections arranged between adjacent or flanking large diameter bodies. The small-diameter sections can be, for example, second connectors for connecting or engaging the first connector on a nearby link. In the device 480, the small diameter sections are joints 488 (e.g., connectors, couplings, attachment bodies, clamping bodies, clamps).

In the links 484 of the chain 482 of the implant device 480, the sockets 486 and the joints 488 are integrally formed and are shaped from a single or continuous piece of material. In some spinal implant devices, the links can include or be embedded with additional biocompatible material, for example a biocompatible polymer, metal, ceramic, composite, or any combination thereof. Further, some implant devices have osteoinductive properties and/or are made at least partly from osteoinductive materials. The sockets 486 and joints 488 connected in the chain 482 are uniform in shape, however, some chains many have non-uniformly shaped sockets and joints.

In some chains, the links releasably engage each other and are configured to release engagement at a predetermined disconnection force, pressure, or orientation. The attachment structures on each link which form a connection between the links may form a releasable connection or may releasably connect one link to another. The releasable connections of the attachment structures can be configured to release or disconnect links in a chain at a predetermined parameter. For example, the predetermined parameter may be a predetermined force (e.g., compressive force or expansive force), pressure, or orientation. The predetermined parameter can be adjusted based on the intended use and/or intended body part receiving the chain.

The predetermined parameter can be an "emergency" or "safety" parameter to prevent the chain from tearing, over-extending, or applying a destructive force on walls of a cavity receiving the chain. For example, a chain for insertion into a cavity in a body part with a soft, or pliable membrane wall may be configured to disconnect at a predetermined pressure to prevent that chain from puncturing the membrane during insertion. The predetermined pressure of attachment structures in a chain for insertion into a soft walled cavity may be less than a predetermined pressure of attachment structures in a chain for insertion into the cavity with a hard, rigid wall.

Some attachment structures may be "designed to fail", in that the attachment structures disconnect the connection between the links in a certain environment (e.g., when inserted into the cavity of the body, in the presence of a fluid, or under a temperature). Where the attachment structures form a "designed to fail" connection, attachment structures of a first link and second may release the connection due to the force of first link contacting a wall of the cavity. Alternatively, the attachment structures may be fixed together, in part, by a dissolvable, breakable, rupturable, or meltable material configured to release the connection between the links in certain environments. For example, the material may dissolve in the presence of an activation fluid, may melt under a melting temperature, may shear upon receiving a force, or may rupture under a predetermined pressure differential. The material may be shaped to fix the first and second link together, for example a pin or clutch. Other materials may form a coating, adhesive, or perforated connector (e.g., a beam with a weakened section) that temporarily binds or holds the links together. The coatings can carry osteoinductive or osteoconductive materials that may stimulate or promote growth. In some cases, the coatings carry medicament for assisting in new bone grown (e.g., anti-inflammatories, antibacterials, antifungals, antivirals, bone growth stimulators or hormones, etc.).

The links 484 of the chain 482 include a first link 484*a*, a second link 484*b*, and a third link 484*c*. The first and second links 484*a*, 484*b* are connected by a first joint 488*a* for the first link 484*a*. The second and third links 484*b*, 484*c* are connected by a second joint 488*b* of the second link 484*b*.

Each link 484 has an exterior surface 490 which extends from the first end 492 to the second end 491. The exterior surface 490 defines an interior volume 492 of the link. The internal volume 492 and the exterior surface 490 form an infill structure 494 and/or infill pattern 496 that mimics the structure of a bone. The sockets 494 and joints 498 of the links 484 are substantially similar to the struts 358 and barrels 356 of the implant device 350, however, the exterior surface 490 of the link 484 forms part of the infill structure 494 rather than a shell around the infill structure 494. In some links, the exterior surface is substantially similar the shell 360 in that the exterior surface encompasses the infill structure.

The infill structure 494 includes a bone-like infill pattern 496. The bone-like pattern may be a honeycomb pattern to imitate cortical bone or a gyroid pattern to imitate cancellous bone. Each link of the chain can include the same infill pattern and/or infill structure or may have a different infill pattern or infill structure. The links 484 in the chain 482 form a mono-patterned chain 482 with a honeycomb infill pattern 496.

In some cases, a link can include a first external surface defining a first interior volume and a second external surface defining a second interior volume. First internal volume has first infill structure with a first infill pattern. The second internal volume has a second infill structure with a second infill pattern. In some cases, at least one of the first and second infill patterns is a bone-like infill pattern. In some chains, the first pattern is a honeycomb infill pattern, and the second infill pattern is a gyroid infill pattern.

Infill structures and patterns can have a wide variety of dimensions, orientations, and combinations that impart characteristics to the links and/or chains formed by the infill structures and patterns. Chains and/or individual links can contain a single infill pattern or multiple infill patterns. Where each link in the chain has the same infill pattern, the chain, link, and infill structure can be considered "mono-patterned." Mono-patterned chains can include only mono-patterned links.

Other chains can have a variety of different infill patterns within the individual links or between the multiple connected links. Where a chain contains at least two infill patterns the chain can be described as a "multi-patterned." A multi-patterned chain can be, for example, a first link with a first infill structure having a first infill pattern (e.g., a honeycomb pattern) connected to a second link with a second infill structure having a second infill pattern (e.g., a gyroid pattern). In some chains, the first infill pattern may be a first honey comb pattern with channels of a size and the second infill pattern may be a second honeycomb pattern with channels of a different size.

In addition, a multi-patterned chain can include at least one individual (unitary) links with at least two or a variety of infill patterns (e.g., honeycomb, webbed, gyroid, sinusoidal, hatched, weave, braided, and/or linear). A link and/or infill structure containing at least two infill patterns can be described "multi-patterned." For example, a multipatterned chain can include a multi-patterned link with an infill structure having a first infill pattern (e.g., a honeycomb pattern) and a second infill pattern (e.g., a gyroid pattern). In some chains, the first infill pattern may be a first honeycomb pattern with channels of a size and the second infill pattern may be a second honeycomb pattern with channels of a different size.

The infill structure 494 is rotationally symmetric around the length axis 114 and/or around the link axis. As such, the mono-patterned link 484 can have only two potential orientations while maintaining the rotational symmetry, an orientation perpendicular to the link axis (FIGS. 29-33) and an orientation parallel to the link axis. Rotational symmetry of the infill structure can simplify the printing process and/or can simplify the steps of connecting the links. Additionally, rotational symmetry can also increase the likelihood that a given opening 366 of the infill structure 494 will line up with and provide a scaffold to new bone growth. Where the infill pattern of the link is orientable but not rotationally symmetric, the infill pattern may have a wide set of orientations (at least two orientation) each having a unique orientation axis relative to the length axis, the height axis, the width axis, and/or the link axis.

In addition, while infill structures with the same or different infill structures has been described, the chain of multiple connected links can have a variety of infill patterns oriented at different angles or orientations. A chain with multiple pattern orientations can be considered a "variably oriented." Such a chain can consist of a multi-patterned link and/or mono-patterned links. Thus, both a mono-patterned chains and multipatterned chains can be variably oriented chains. For example, a foldable chain with at least one orientable pattern (e.g., infill patterns with channels) can have a first infill orientation and a second infill orientation. The first infill orientation is defined by a first infill pattern of a first link and the second infill orientation is defined by a second infill pattern of a second link; however, some second infill orientations are defined by a second infill pattern in the first (multi-patterned) link.

Figure 29:
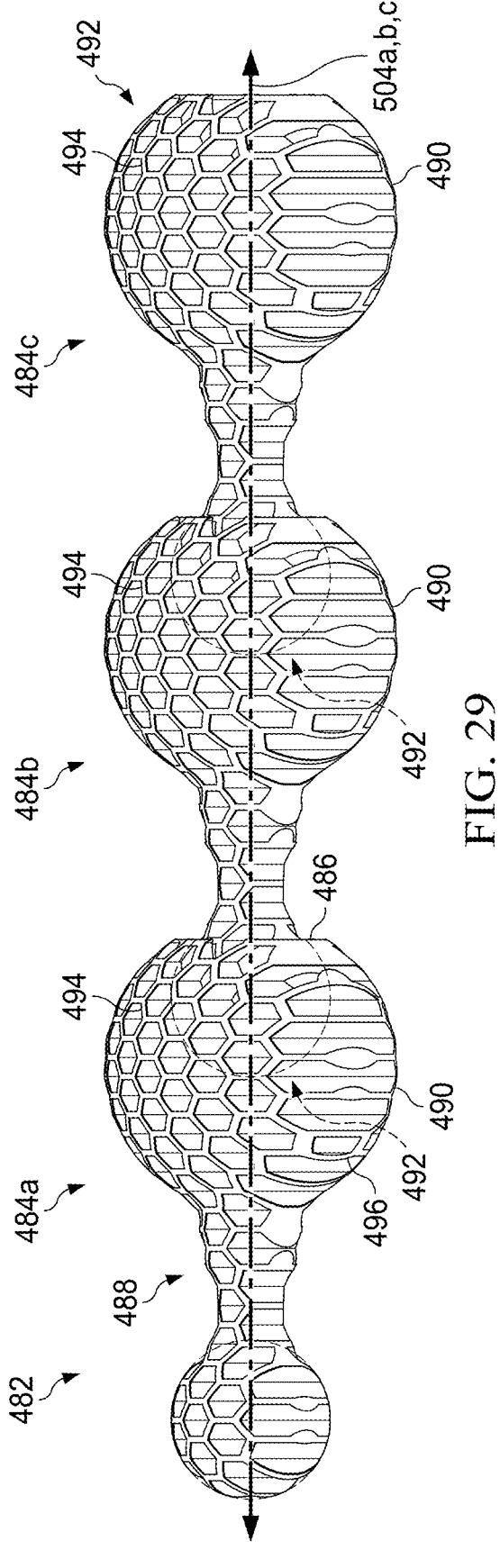
FIG. 29 is a top view of the chain in the straightened position. The infill structure is a honeycomb infill pattern for imitating the structure of a cortical bone.

FIG. 29 is a top view of the chain 482 in the straightened position. The infill structure 494 is a honeycomb infill pattern 496 for imitating the structure of a cortical bone. The honeycomb pattern 496 of the infill structure 494 spans the entire interior volume 492 in a first orientation. The infill structure 494 of the device 480 is substantially similar to the infill structure 364 of the device 350, however, the infill structure 494 is dimensioned or sized to span individual link 484 rather than span the unitary strand 352. The channels 370 and walls 372 of the infill structure 496 are exposed to the surrounding environment whereas only portions of the infill structure 364 adjacent openings 366 are exposed in the implant device 350.

The infill structure 494 of each link 484a-c has the same infill pattern 496 (e.g., a honeycomb pattern for imitating the structure of a cortical bone). As such, the links 484 are "mono-patterned links" which connect to form the "mono-patterned chain" 482. In addition, each link 484a-c has an infill pattern 496 with channels 370 that align with the height axis 116. As the links 484 are rotatable relative to each other, the channels 370 can also be aligned with the width axis 118. As such, channels 370 may be considered to have the same orientation where the orientation axis is perpendicular to the length axis. In this configuration, the chain 492 includes only links of a honeycomb pattern and each honey comb pattern has the same orientation. As such, the chain 492 is a uniformly oriented, mono-patterned chain 492 formed by mono-patterned links 484 with infill patterns 496 at a first orientation.

The honey comb pattern 496 is rotationally symmetric when aligned on the length axis, the width axis, or the height axis. As such, the honeycomb pattern can have at least three orientations defined by the channels 370. A first orientation of the honeycomb pattern aligns the channels 370 with the height axis 116 (FIGS. 29-33). A second orientation of the honeycomb pattern aligns the channels 370 with the length axis 114. A third orientation of the honeycomb pattern aligns the channels 370 with the width axis 118. Some chains may have a mono-patterned structure with an infill pattern oriented differently on each link. A chain having one or more patterns oriented along different, non-parallel axes can be considered a "variably oriented" infill structure. The one or more patterns of the variably of a variably oriented chain, at least one link has a multi-patterned structure or a mono-patterned structure and uniformly oriented, multipatterned and variably oriented, mono-patterned, and uniformly oriented, or mono-patterned and variably oriented. Additionally, some infill patterns, for example webs, do not have a clear orientation. In infill structures that have an infill pattern with little to no orientation or alignment with an axis, the infill structure may be a mono-patterned structure or a multi-patterned structure.

Figure 30:
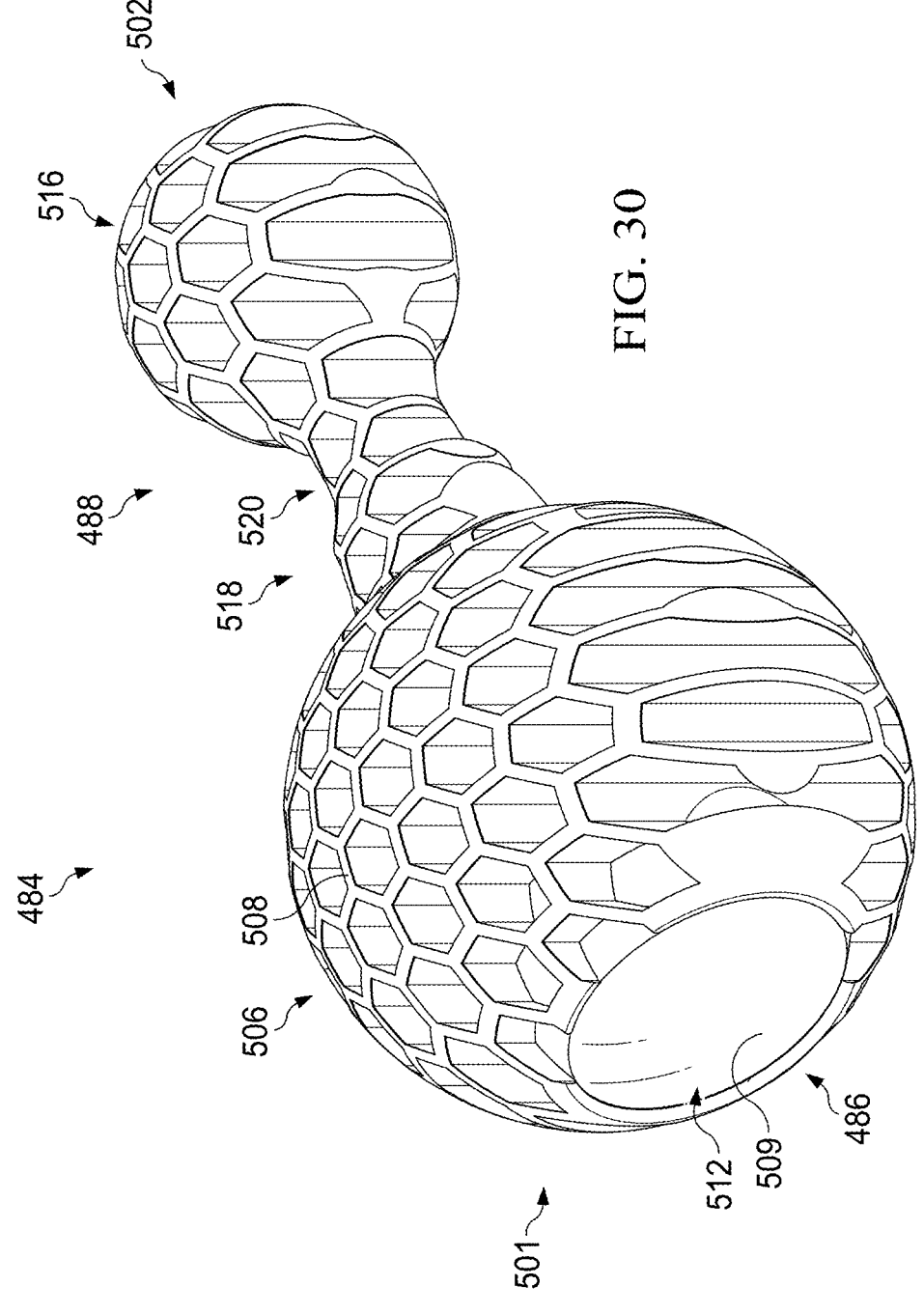
FIG. 30 is a perspective view of an individual link of the links of the device.

FIG. 30 is a perspective view of an individual link 484a-c of the links 484 of the device 480. The link 484 has a socket 486 and a joint 488. The socket 486 is arranged at a proximal end 501 of the link 484. The socket 486 includes a socket body 506 having a with radius Rs. The socket body 506 has an outer face 508 and a smooth inner face 509. The smooth inner face 509 prevents friction between the socket 486 and the joint 488 when the socket 486 receives a joint 488 from another link 484 to form a ball-and-socket connection. The socket body 506 defines an opening 510 at the proximal end 501. The opening 510 extends from the outer face 508 to the inner face 509 so that the opening 510 connects to a socket recess 512. The opening 510 has an opening radius Ro. The inner face 509 of the socket body 506 is defined by the socket recess 512. The recess 512 has a recess radius Rr which is greater than the opening radius Ro.

The joint 488 extends from the socket body 506 to a second end 502 of the link 482. The joint 488 includes an insert, for example a ball 516, and a shaped body 518. The ball 516 is disposed at the distal (second) end 502 and has a ball radius Rb. The ball radius Rb less than the socket radius Rs and greater than the opening radius Ro. The configuration allows rotation between the links 484 while preventing the joint 488 from disengaging the socket 486. The socket recess 512 is sized to receive a ball 516 from another link 482 to fix the link 482 in an at least partially flexible rotatable connection.

The shaped body 518 is arranged between the ball 516 and socket body 506 to connect the ball 516 of the link 482 and socket body 506 of the link 482. The shaped body 518 has a divot 520 defined disposed adjacent to the ball 516. The divot 520 is sized to receive a portion of the outer face 508 adjacent the opening 510 so that the ball-and-socket connection has a wider angular range as compared to divot-less shaped bodies.

The link 484 is a mono-patterned link, however, some links may be multi-patterned links. For example, a multi-patterned link may have a multi-patterned infill structure in which the sockets have socket infill pattern (e.g., honeycomb, small honeycomb) and the joints have a joint infill pattern (e.g., gyroid, large honeycomb), different from the socket infill pattern. In some multipatterned links, the socket infill pattern and joint infill pattern are uniformly oriented or are variably oriented.

Figure 31A:
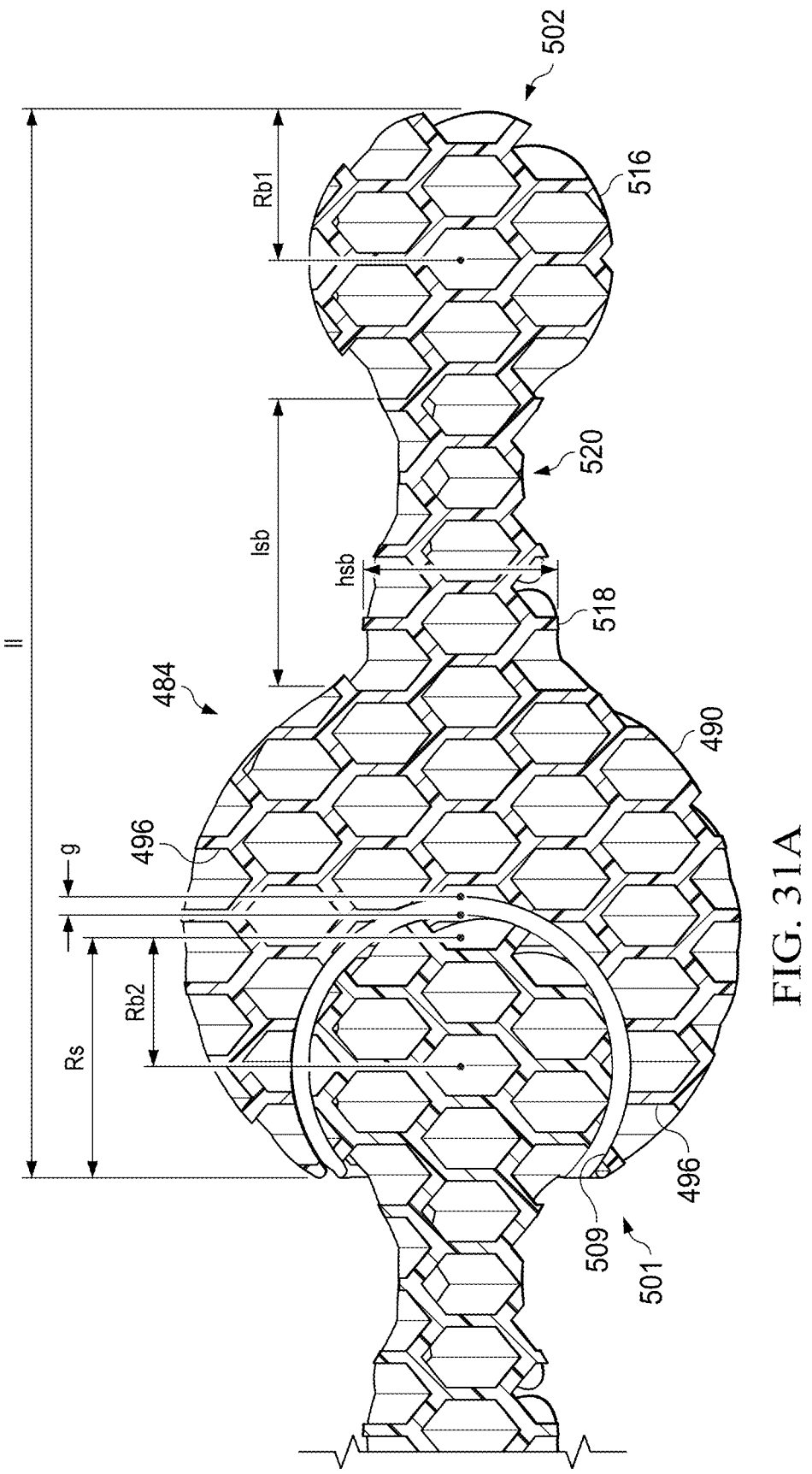
FIGS. 31A and 31B are cross sectional top views of the link alone, or in connection with a second link.
Figure 31B:
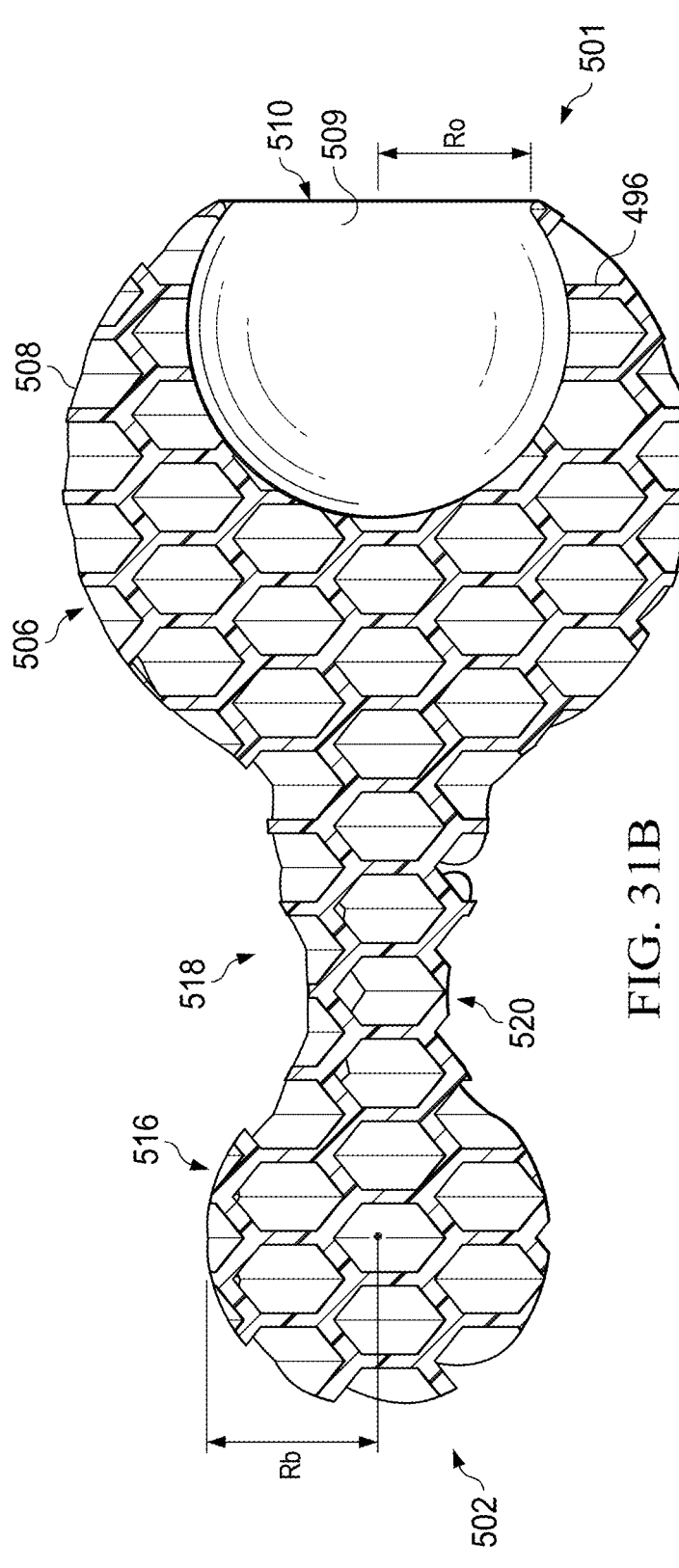

FIGS. 31A and 31B are cross sectional top views of the link 484a alone, or in connection with a second link 484b. The shaped body has a height hsb measured along the height axis 116 and a length lsb measured along the length axis (link axis). In the implant device 480, the length lsb of the shaped body 518 is about equal for each of the shaped bodies 518 in the chain 492. Additionally, height hsb of the shaped body 518 is about equal for each of the links 484. The length of the shaped body lsb is proportional to the socket radius Rs, for example the length of the body lsb is about two thirds of the socket radius Rs. The socket radius Rs can about 1/6 cm to about 1 2/3 cm, for example 5/6 cm. The socket radius Rs is at least double the ball radius. The inner face 509 of the socket body 506 is distanced from the connecting ball 516 by a gap g. The gap is about 5% to about 15% of the socket radius Rs, for example about 8% to about 10%.

In some devices, the height lsb about 1 mm to about 15 mm, for example, about 2 mm to about 8 mm, or about 4 mm to about 6 mm. The length lsb of the joint 488 is about The length lsb is about 0.5 mm to about 50 mm, for example, about 1 mm to about 25 mm, about 4 mm to about 10 mm, about 5 mm to about 40 mm, about 2 mm to about 15 mm, about 1 mm to about 8 mm, about 0.5 mm to about 5, bout 2 mm to about 6 mm, about 3 mm to about 5 mm, about 1 mm to about 4 mm, or about 2 mm to about 4 mm.

Figure 32:
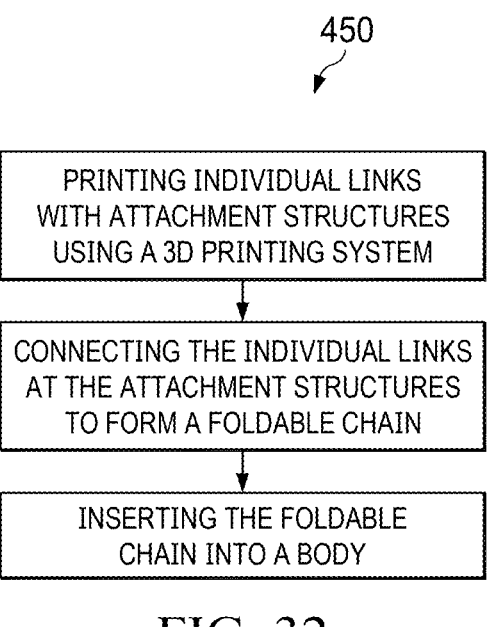
FIG. 32 is a flowchart of a method of use for inserting a flexible or foldable spinal implant into a cavity of a body.

FIG. 32 is a flowchart of a method 500 of use for inserting a flexible or foldable spinal implant into a cavity of a body. The method 500 is described with reference to the spinal implant device 480, however, the method can be used with any applicable device or system. The method 500 is substantially similar to the method 400, however, the method 500 includes printing at least one link of a chain rather than printing a unitary strand of barrels connected by integral struts. Additionally, the method 500 can include a pre-insertion step of connecting the links into a chain if the links are printed individually.

The method 500 includes unpackaging an assembly containing a spinal implant device 480 in the printed state. In the printed state, the implant device 480 is flexible and includes at least one link formed by a single body of material or materials. The link includes sockets and joints integrally formed or joined with the socket. The chain also includes a bone-like infill structure with a bone-like infill pattern (e.g., a honeycomb pattern or gyroid pattern). The exterior shell and interior volume seamlessly connect to form the infill structure. The infill structures are shaped to receive and promote bone growth when inserted into a body.

The joints and the sockets of a chain are centered along an axis in the straightened position of the chain. The first end of the spinal implant device is then inserted and fed through a cannula. The cannula discharges the first end of the spinal implant device into a prepared or unprepared cavity of the body. The cavity is defined in or adjacent to a collapsed bodily structure (e.g., a vertebrae). The first end of the implant device extends into the cavity until the first end abuts a wall of the cavity. The wall of the cavity provides a force against the first end of the implant device and a conveying force on the second end of the implant device applies a pressing force to the implant device. Under one or both forces, the joints of the implant device flex, fold, or rotate so that the entire chain enters the cavity. The chain continues to fold and form a dense mass or cluster until the entire the chain is inserted into the cavity. The sockets are arranged close together in the clustered formation and support the collapsed structure of the body by pressing outwardly on the walls of the cavity.

The 3D printing system 410 can also be used to form a chain of links and/or to form individual links with a bone-like infill structure. In use, the system prints a link 482 from a bottom end to the top end of the link. In some cases, the system extrudes the link from the proximal end of the distal end, rather than from a bottom end to a top end. The system can extrude or print the chain so that the link axis is angled or perpendicular to the extrusion axis. Additionally, or alternative, the system can extrude ort print the chain so that the length axis is aligned with or parallel to the extrusion axis.

The system forms a first portion of the link such that the first portion of the link includes an exterior surface extending from a closed bottom end to an open end. The open end may be oriented towards the nib so that the extrusion nip can extrude material into or on the open end of the link. The system may also form a second portion of the link on the first portion of the link. The second portion of the link extends from an open end to a close top end, thereby forming the individual link with the exterior surface and infill structure. The infill structure may be a bone-like infill structure with a bone-like pattern, such as a honeycomb pattern and/or a gyroid pattern.

In some system, the first potion extruded by the system is a partial chain formed of partial links. The first portion can be a half of the total chain and the second portion is the remaining half of the total chain. The first portion can include at least one printed partial link (e.g., one, two, three, four, five, six, seven, eight, nine, ten, twenty, fifty, one hundred partially printed links). The second portion can include the remaining part of the chain (e.g., one, two, three, four, five, six, seven, eight, nine, ten, twenty, fifty, one hundred link parts). In some cases, the first portion includes a first partially formed socket having a partially formed shell and/or a partially formed infill structure, a second partially formed socket having a partially formed shell and/or a partially formed infill structure, and a partially formed joint having a partially formed shell and/or a partially formed infill structure. The printer may extrude PEEK or PEKK to form the chain and/or link.

FIGS. 33-37 are cross sectional side views of various connections formed by various attachment structures in a foldable chain 480 formed by the 3D printing system 410.

The attachment structures include first link 521 a socket 522 and a second link 524 with a joint 526 an insert 528 (e.g., ball or disc). While insert-and-socket attachment structures have been described, other chains can include one or more types of attachment structures.

Figure 33:
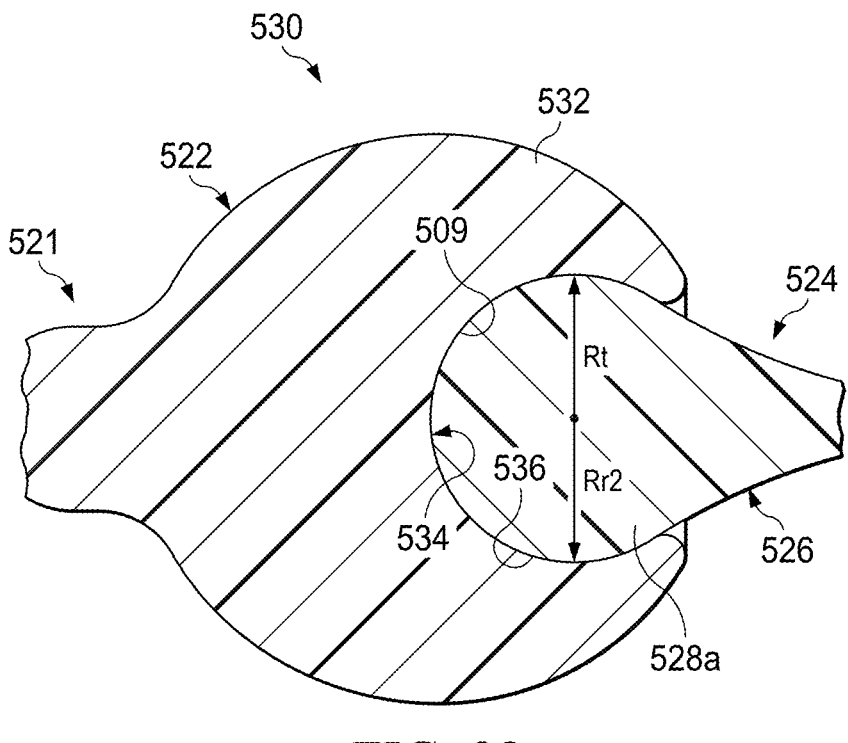
FIG. 33 is a cross sectional side view of an attachment structure for forming a flexible, non-collapsible chain between a first link and a second link.

FIG. 33 is a cross sectional side view of an attachment structure 530 for forming a flexible, non-collapsible chain 492 between a first link 521 with a socket 522 and a second link 524. The socket 522 is substantially similar to the socket 486, however, the socket 522 has a socket body 532 with tight-fit recess 534 whereas the socket 486 has a socket body 506 with a recess 512 sized to have a gap g between the ball 516 and the inner face 509 of the body 506. In addition, the joint 526 is substantially similar to the joint 488, however, the joint 488 has a teardrop shaped insert 528a with a groove whereas the joint 488 includes a ball shaped insert with a shallower divot. The teardrop insert 528a has a radius Rt. The socket has a recess radius Rr2 that is equal to the insert radius Rt of the joint 526. The recess radius proportionally less than the socket radius Rs, for example, the recess radius is about 10%, 20%, 15%, 20%, 25%, 33%, 50%, 66% or 75% of the socket radius. The groove receives the edge of the opening of the socket body when the chain folds. The angle between the first link axis and the second link axis is greater than 20° (e.g., greater than 23°, 40°, or °60).

In a chain formed by the first and second links 521, 524 the insert 528 is arranged in a socket recess 534 of the socket body 532 so that an exterior surface 536 of the ball 516 abuts the smooth inner face 509 of the socket body 506. The exterior surface of the ball may be part of an exterior surface of the second link.

Figure 34:
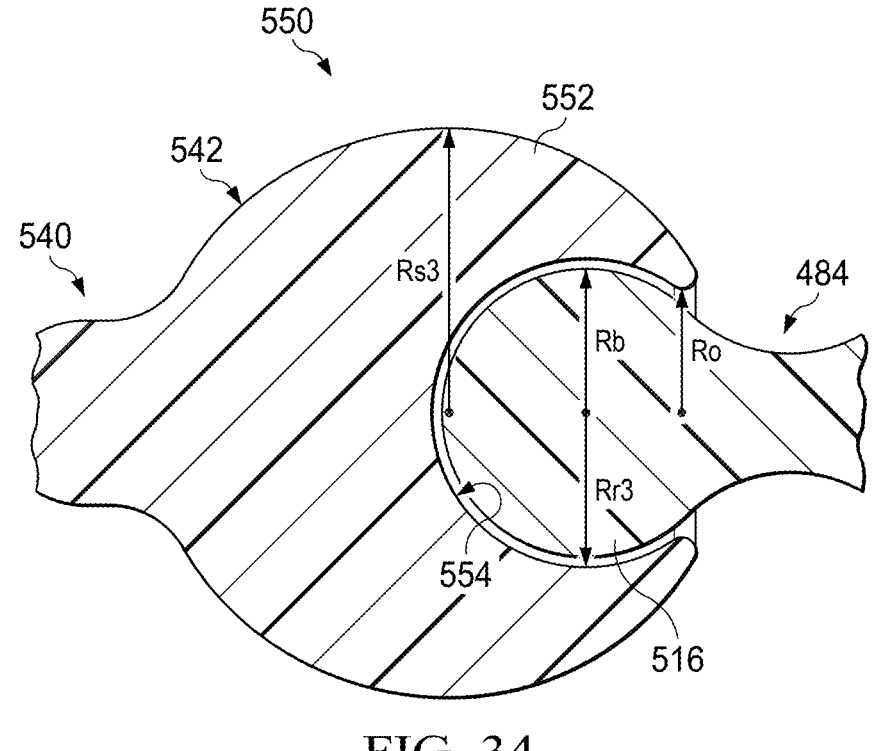
FIG. 34 is a cross sectional side view of an attachment structure for forming a flexible, non-collapsible chain between a first link and the second link.

FIG. 34 is a cross sectional side view of an attachment structure 550 for forming a flexible, collapsible chain 492 between a first link 540 and the second link 484. The socket 542 is substantially similar to the socket 486, however, the socket 542 has a socket body 552 with loose-fit recess 554 whereas the socket 486 has a socket body 506 with a recess 512 sized to have a small gap g between the ball 516 and the inner face 509 of the body 506. The socket 542 receives the ball 516 of the second link 484, described with reference to FIGS. 29-32. The ball insert has a radius Rb. The socket has a socket radius Rs3 is greater than the recess radius Rr3. The recess radius Rr3 is greater than an opening radius Ro and the ball radius. The recess that is greater than the ball insert radius Rb greater than the opening radius Ro.

The ball radius Rb may be proportionally less than the socket recess radius Rr3 so that the ball 516 can translate axially and/or radially within the recess 554 of the socket 542 and can rotate within the recess 554 to fold the chain 492 and/or collapse the chain 554. In some cases, the ball radius Rb is about 90%, 80%, 75%, 66%, 50%, 45%, 40%, 33% or 25% of the socket recess radius. The groove receives the edge of the opening of the socket body when the chain folds. The angle between the first link axis and the second link axis is greater than 20° (e.g., greater than 23°, 40°, or °60).

Figure 35:
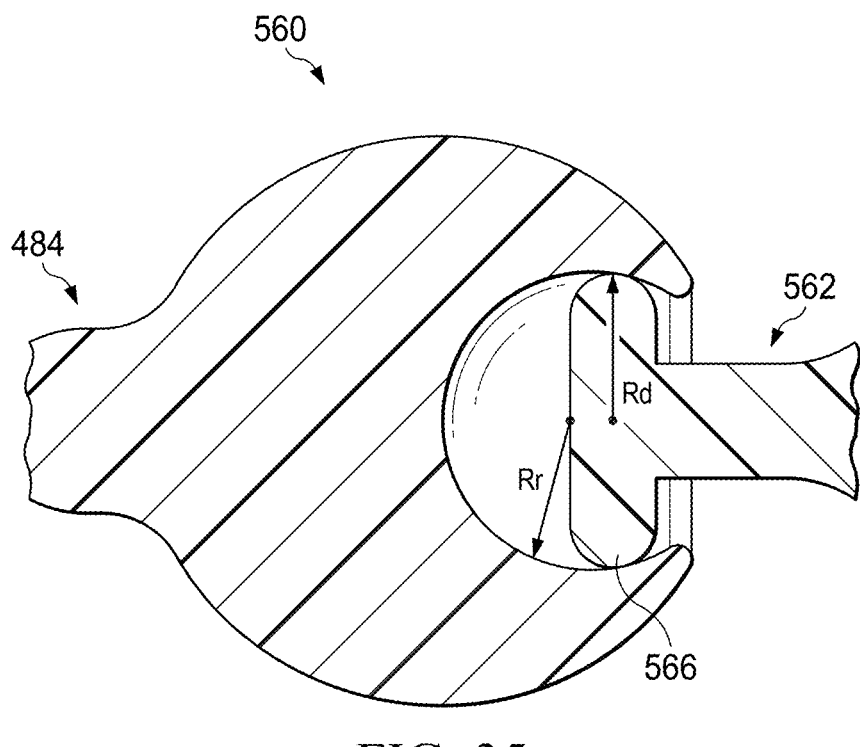
FIG. 35 is a cross sectional side view of an attachment structure for forming a flexible, collapsible chain between a first link and a second link.

FIG. 35 is a cross sectional side view of an attachment structure 560 for forming a flexible, non-collapsible chain 492 between a first link 484 and a second link 562. The first link in the attachment structure 560 is substantially similar to the links 484 described with reference to FIGS. 21-32. The second link 562 is substantially similar to the links 484, however the second link 562 has a disc insert 566 rather than a ball insert 516. The disc 566 has a radius Rd that is about equal to or less than the radius of the recess Rr. In this configuration, the links 484, 562 may rotate relative to another but are prevented from moving axially within each other.

Figure 36:
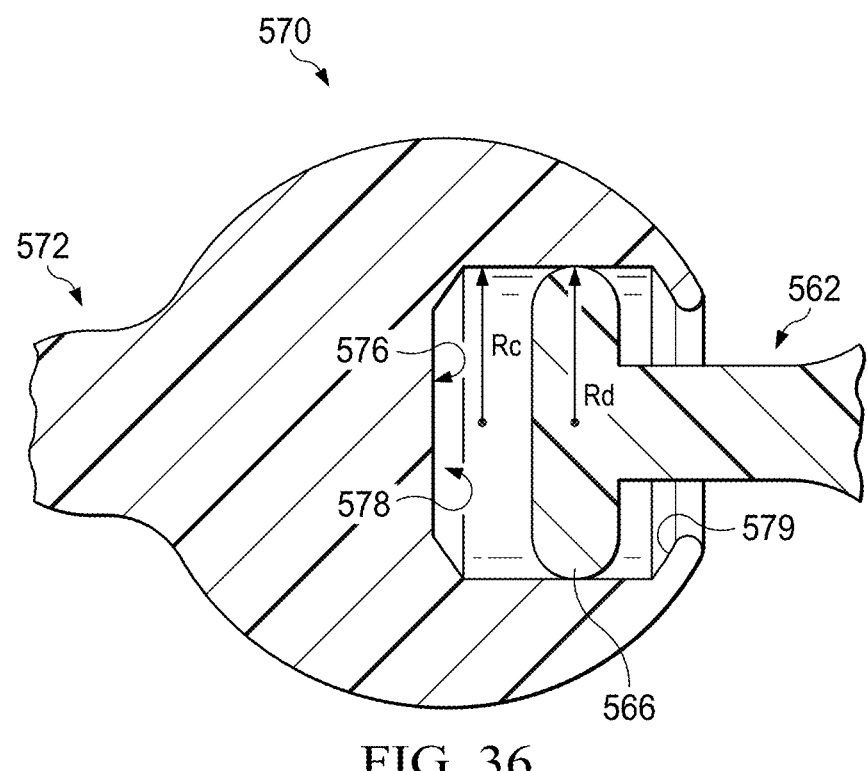
FIG. 36 is a cross sectional side view of an attachment structure for forming a stiff, collapsible chain between a first link and a second link.

FIG. 36 is a cross sectional side view of an attachment structure 570 for forming a stiff, collapsible chain 492 between a first link 572 and a second link 562. The first link in the attachment structure 560 is substantially similar to the links 484 described with reference to FIGS. 21-32, however, the first link includes a socket 574 with a socket body defining a recess 576 in the form of a column rather than a sphere. The second link in the attachment structure 570 is substantially similar to the second link 562.

The disc 566 has a radius Rd that is about equal to or less than the radius of the recess Rr. The recess column has a depth d which extends from the opening to a closed end 578. The closed end may be a flat surface or a domed end. The recessed column 576 also has a column radius Rc that is equal to or greater than the radius of the disc Rd. When the disc 566 is arranged in the recess 576, the disc is free to move axially along the link axis within the column recess 576. An edge 579 and the closed end 578 form axial stops that prevent further axial movement. In this configuration, the disc 566 and joint 488 of the second link can move axially along the length axis 114 relative to the first link 572. Additionally, the first link and second link are rotatable only on the length axis. As such, the fist link and second link connected by the attachment structure 570 do not fold.

Figure 37:
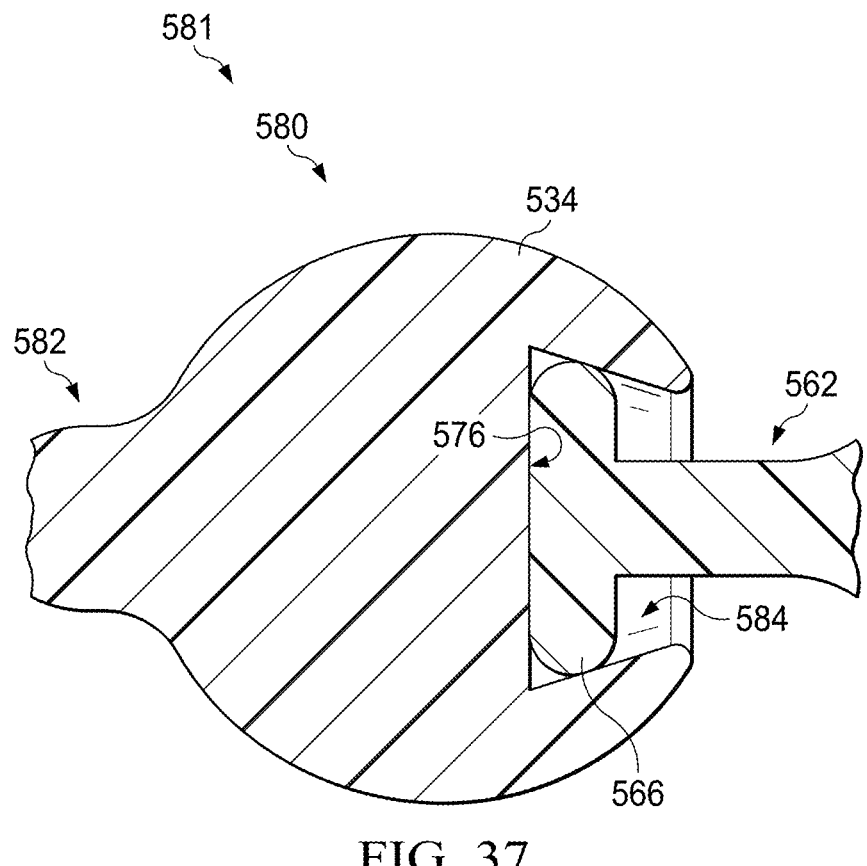
FIG. 37 is a cross sectional side view of an attachment structure for forming a stiff, non-collapsible chain between a first link and a second link.

FIG. 37 is a cross sectional side view of an attachment structure 580 for forming a stiff, non-collapsible chain 581 between a first link 582 and a second link 562. The first link in the attachment structure 580 is substantially similar to the links 521 described with reference to FIG. 33, however, the first link includes the socket body 534 has a socket recess column 584 for forming a close fit with a disc insert 566 rather than a ball insert 516. The second link in the attachment structure 570 is substantially similar to the second link 562.

The disc 566 has a radius Rd that is about equal the radius of the recess Rr. Additionally, the disc has a length ld that is about equal to a depth of the recess column de which extends from the opening to a closed end 578. The closed end may be a flat surface or a domed end. When the disc 566 is arranged in the recess 576, the disc is free to move rotate only amount the central link axis. Additionally, the second link 562 is axially constrained to the first link 582. In this configuration, the first link and second link are rotatable only on the length axis. As such, the fist link and second link connected by the attachment structure 580 do not fold and from a stiff chain.

While simple variations of the attachment structure have been described, some chains of connected links include a modified joint and/or a modified socket.

Figure 38A:
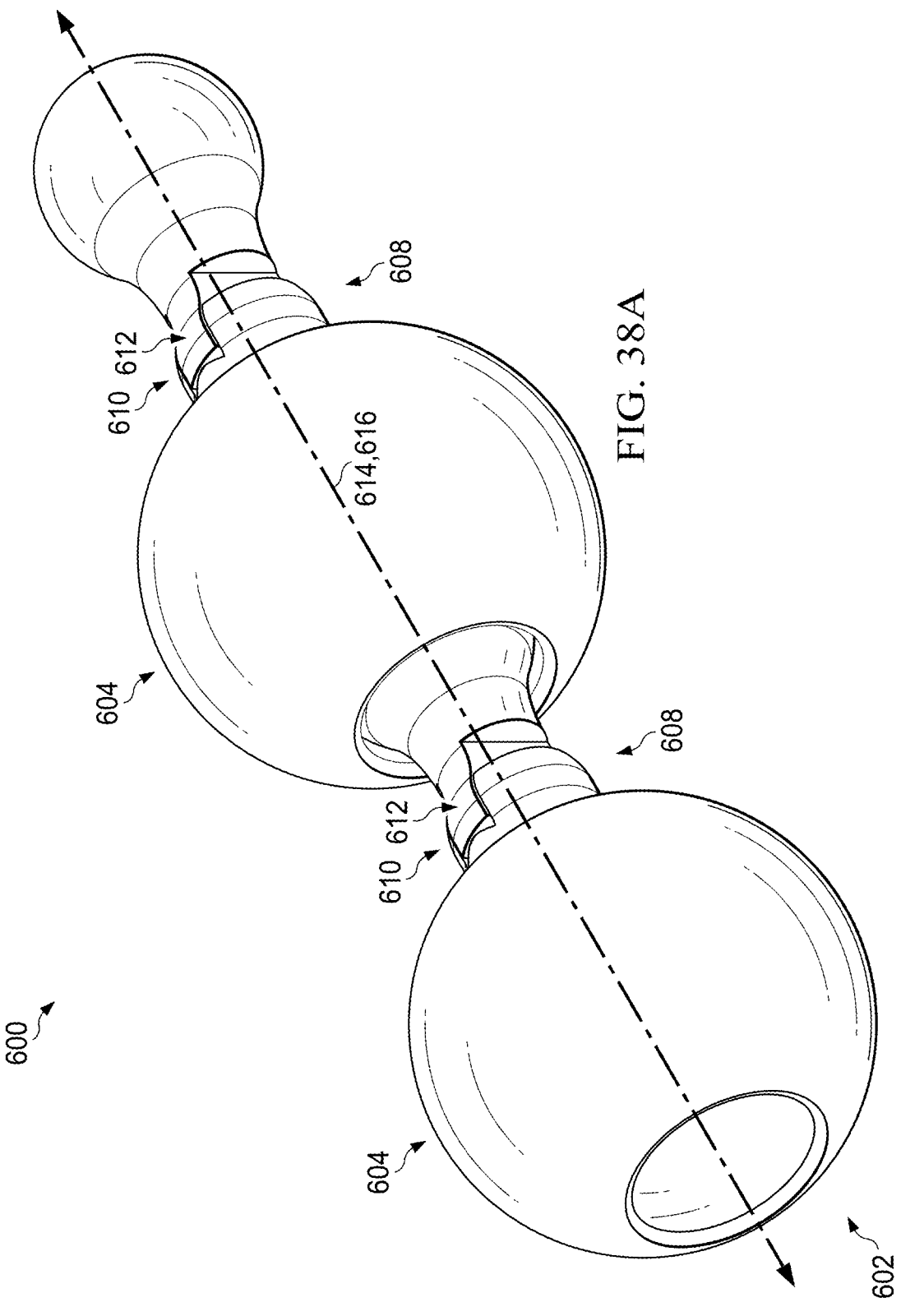
FIGS. 38A and 38B are perspective views of a spinal implant device with a flexible chain formed by connected pivotable links, in the straightened position and the folded position, respectively.
Figure 38B:
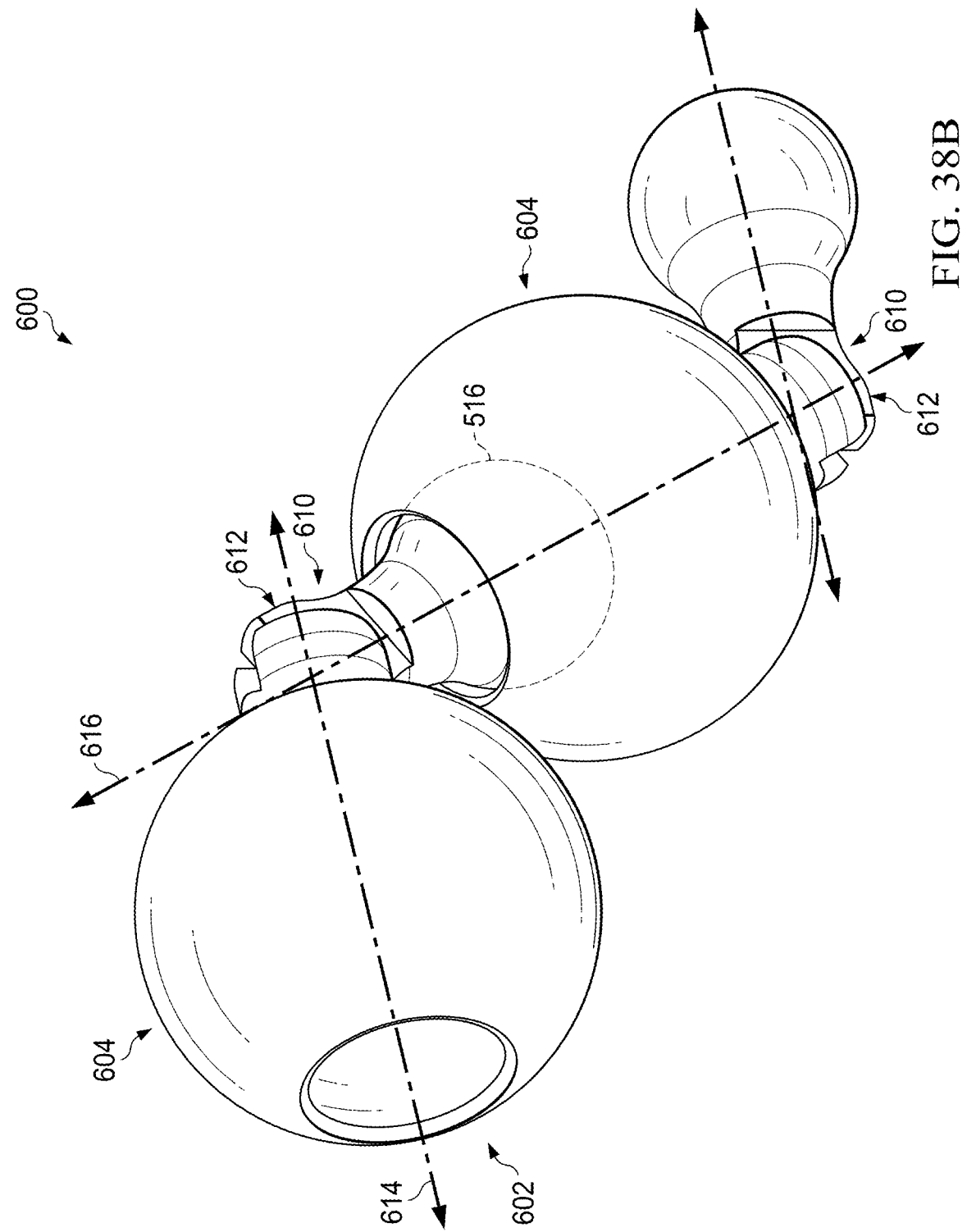
Figure 39A:
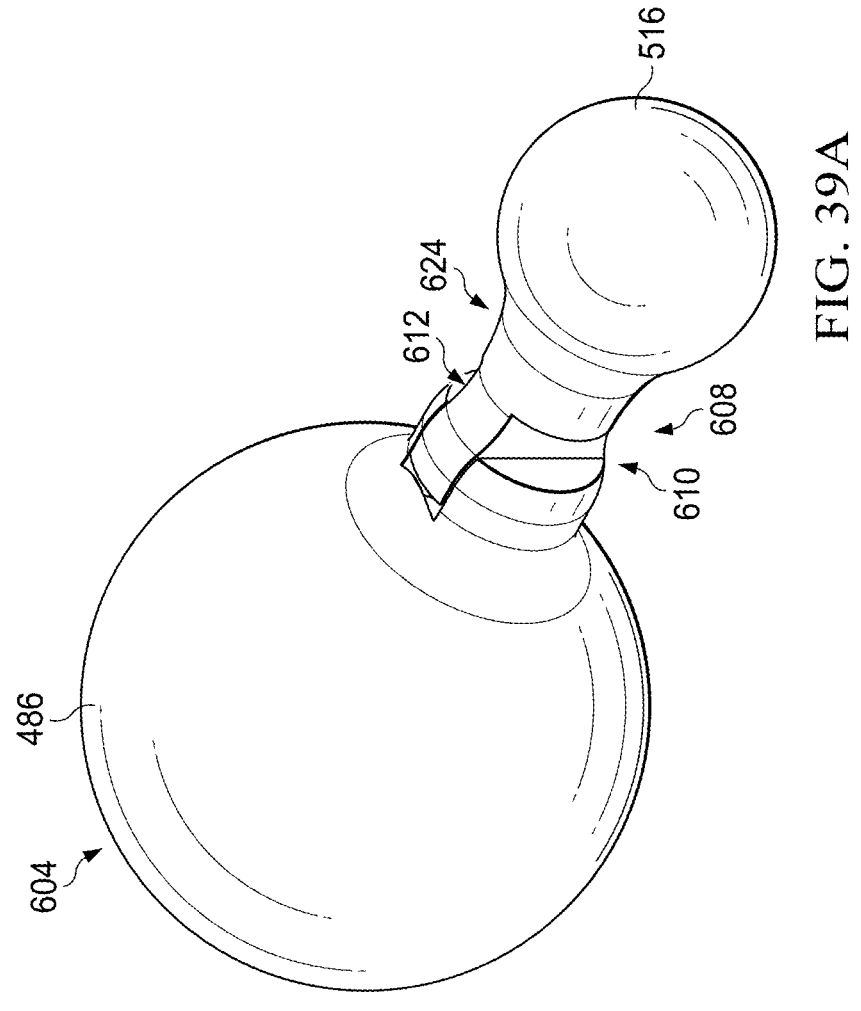
FIGS. 39A and 39B are a perspective view and an exploded view of the pivotable link.
Figure 39B:
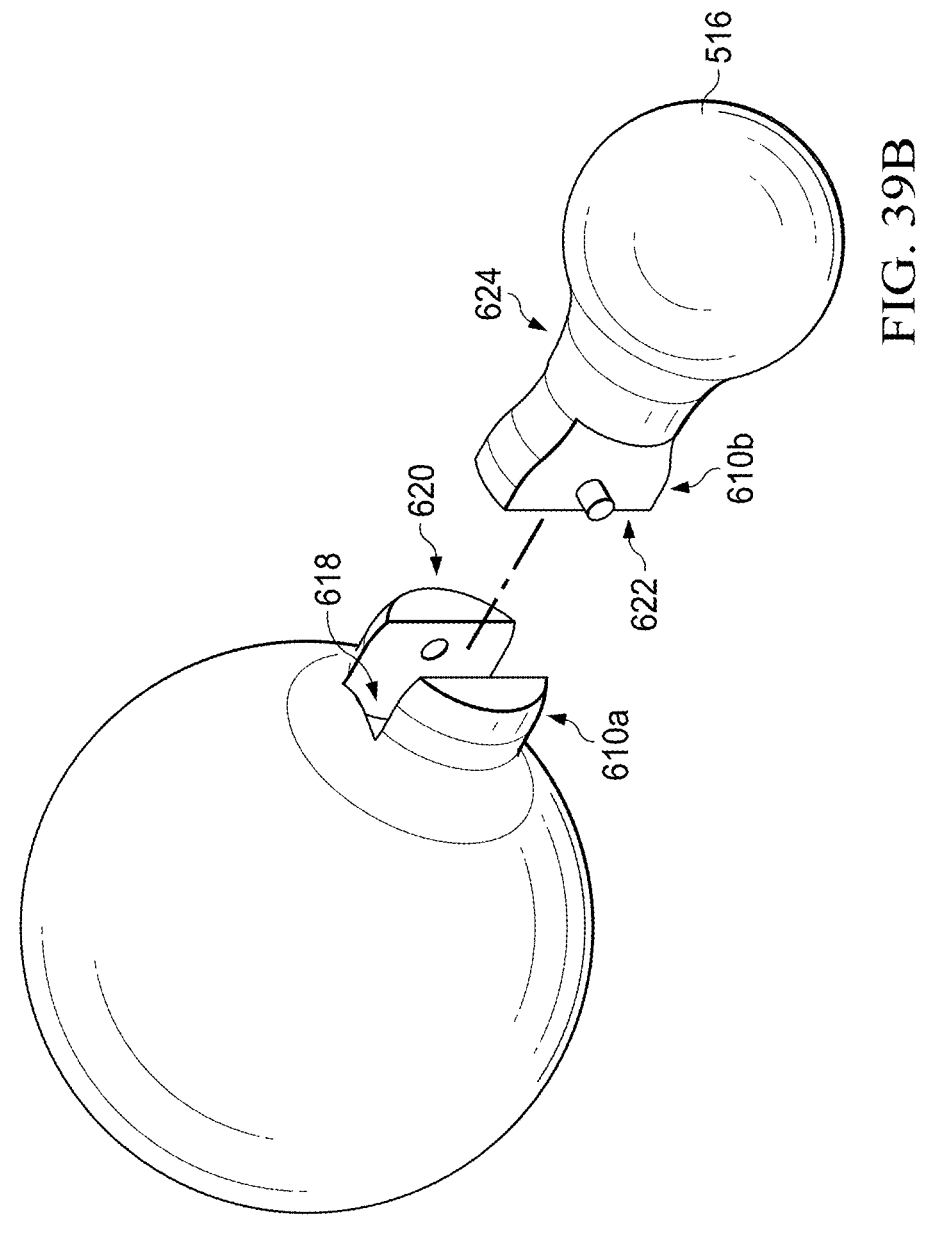

FIGS. 38A and 39B are perspective views of a spinal implant device 600 with a flexible chain 602 formed by connected pivotable links 604, in its straightened position and its folded position, respectively. The spinal implant device 600 and chain 602 are substantially similar to the implant device 480 and chain 482, however, the spinal implant device 600 and chain 602 include at least one pivotable link 604 with a pivotable joint 608. The implant device 600 has an increased range of motion as compared to the implant device 480 due to the pivotable joint 608 in the pivotable link 604.

In the folded position, the pivotable portion and/or the attachment structure can be rotated to fold a flexible chain. In the chain 602, both the pivotable portion 612 and the attachment structure fold. The link 604 has a socket axis 614 defined by the socket and a joint axis 616 defined by the insert 516. In the straightened position (FIGS. 39, 41), the socket axis 614 and the joint axis 616 align along the length axis 114. In the folded position (FIG. 40), the socket axis 614 and the joint axis 616 intersect at an angle. The angle of intersection is the degree of motion provided by the pivotable portion 612 of the shaped body 610.

FIGS. 39A and 39B are a perspective view and an exploded of the pivotable link 604. The pivotable joint 608 is substantially similar to the joint 488, however the pivotable joint 608 includes a shaped body 610 with pivotable portion 612 arranged between the divot and the socket 486. The ball 516 of the link 604 is configured to pivot about the pivotable portion 612 so that the ball 516 of the link 604 moves towards the socket 486 of the same link 604. The pivotable portion increase the total range of motion of the chain 602, for example ranges of motion greater than 20°.

Figure 40A:
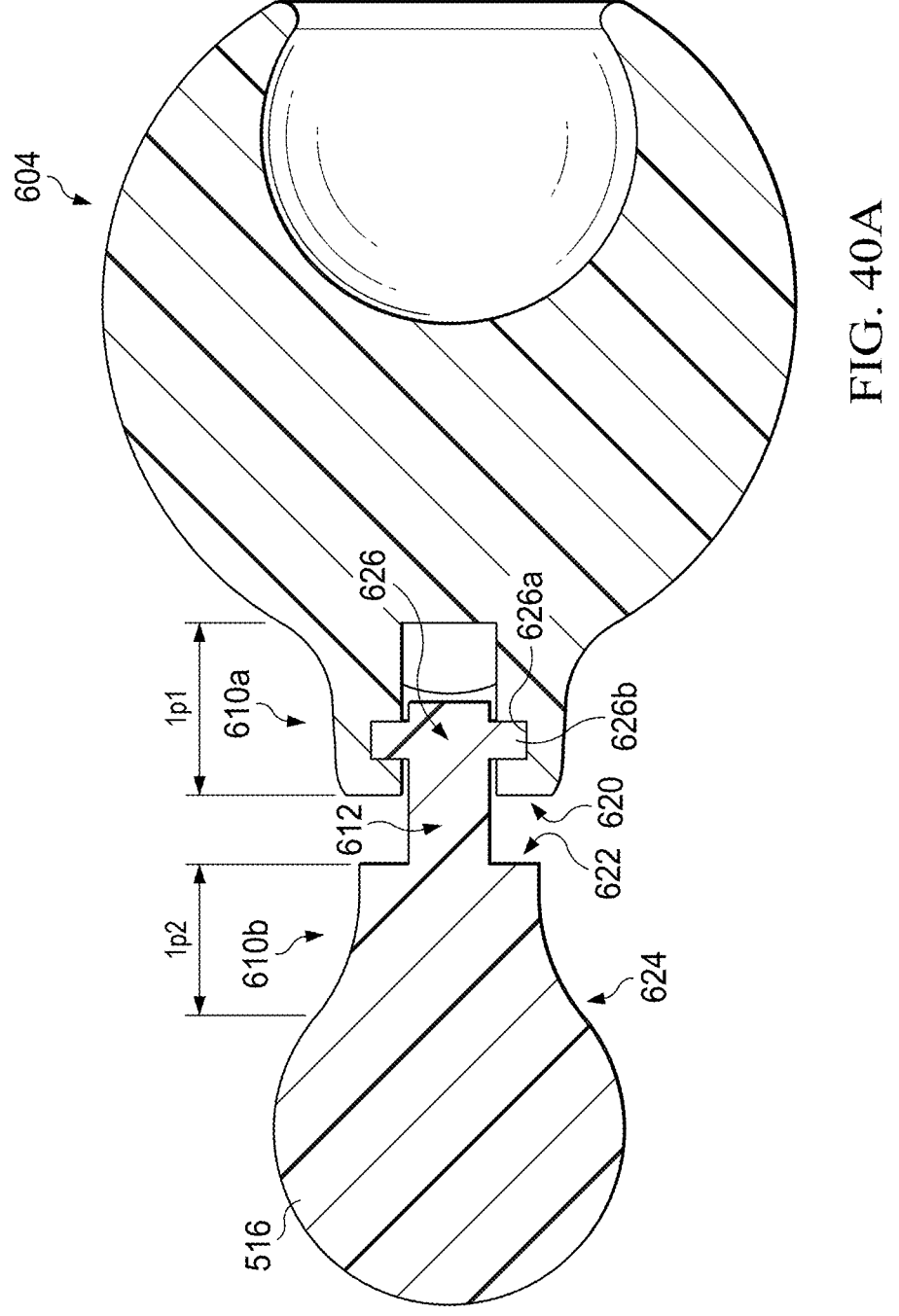
FIGS. 40A and 40B are cross sectional top views of the pivotable link the straightened position and the folded position, respectively.
Figure 40B:
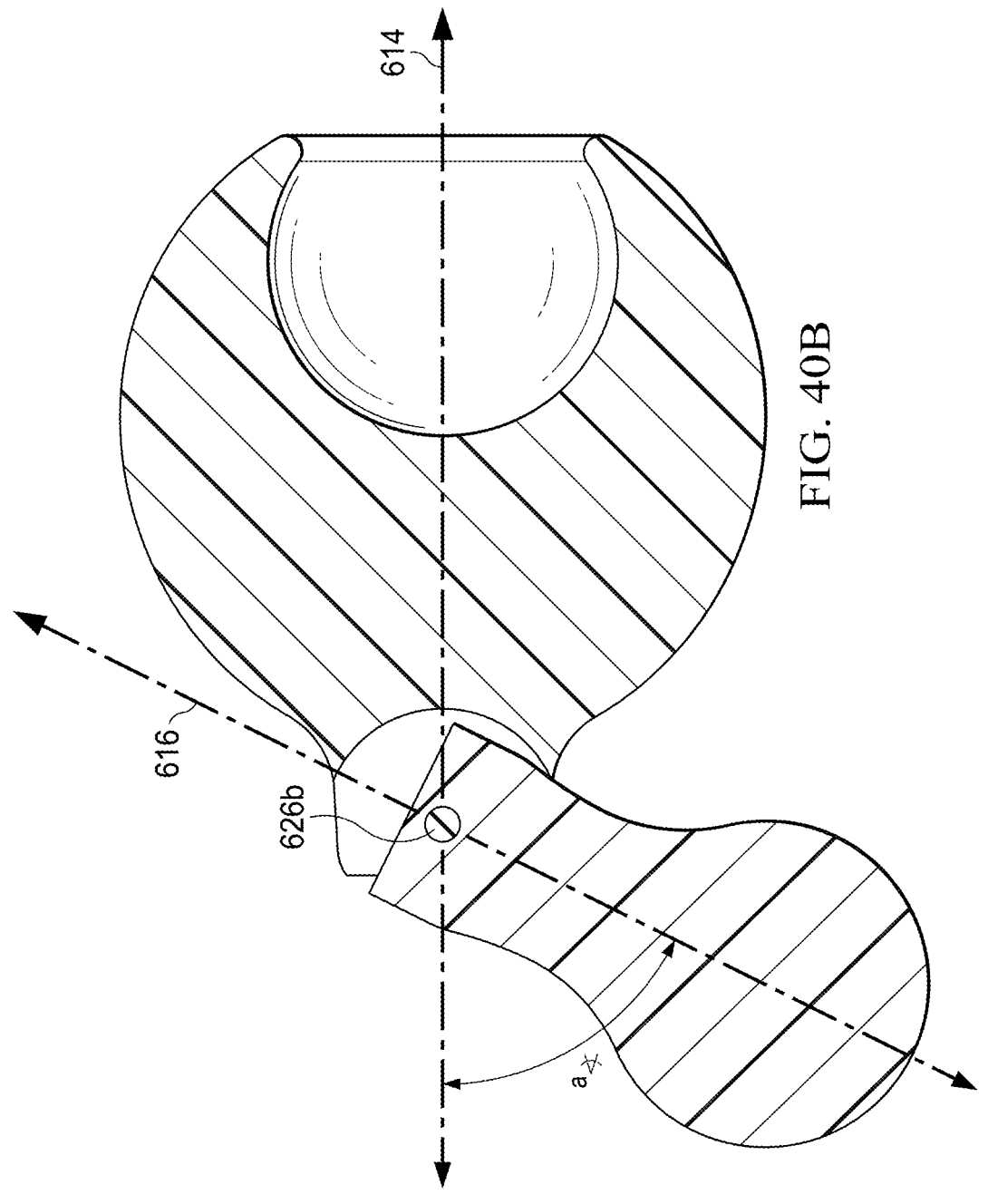

FIGS. 40A and 40B are cross sectional top views of the pivotable link 604 the straightened position and the folded position, respectively. The shaped body 610 has a first (proximal) portion 610a and a second (distal) portion 610b. The first portion 610a connects to the pivotable portion 612 at a pivot (second) end 620. The second portion 610b of the shaped body 610 has a pivot (first) end 622 connected to the pivotable portion 612 and an insert (second) end 624 connected to the ball 516. The pivotable (third, intermediary) portion 612 is arranged between the first portion 610a and the second portion 610b. The first portion 610a and second portion 610b are elongated bodies. The pivotable portion 612 includes at least one pivot 626. The pivot 626 is a hinge 626a with a hinge pin 626b, however, other pivots may be a living hinge, a strip or tab of flexible material, a revolute joint, a ball joint, or a roller joint. In some shaped bodies, the pivotable portion integrally formed or part of either the first portion of the body or the second portion of the body. The first portion 610a has a length lp1 and the second portion has a length lp2. The length of the first portion lp1 is equal to the second portion length lp2. In some cases, the lengths lp1, lp2 are different. In some cases, the first portion length lp1 is longer than the second portion length lp2. In other joints, the second portion length lp2 is longer than the first portion length lp1. In some cases, the pivotable portion includes at least two pivots, for example a first pivot and a second pivot. In this configuration, the first portion of the body may connect to the intermediary portion by the first pivot and the second portion of the body may connect to the intermediary portion by the second pivot.

In some shaped bodies, the pivot portion is a flexible portion formed by a flexible, biocompatible material. The flexible portion has a rigidity that is less than the rigidity of the first portion and/or the second portion. In some shaped bodies, the pivotable portion is arranged adjacent to the divot and/or adjacent to the insert.

The pivotable link 604 can be manufactured by the 3D printing system 410, described with reference to FIGS. 23 and 24. A method 630 for manufacturing a pivotable link with a 3D printing system, us substantially similar to the method 500, however, the method 630 can also include printing a first portion, a second portion, and/or a pivotable portion of a pivotable hinge or a pivotable link. In some cases, radio-opaque markers may be embedded into or attached to the pivotable link.

Figure 41A:
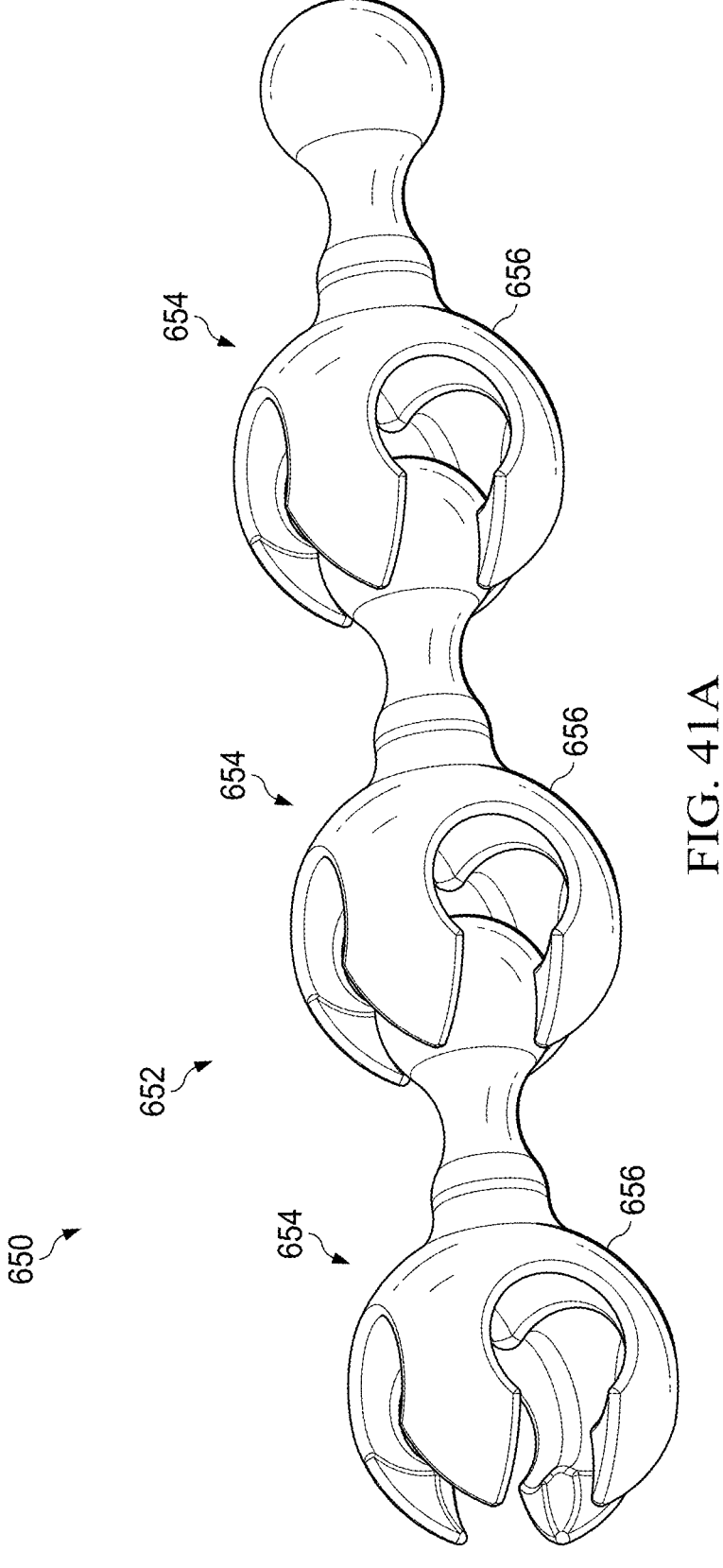
FIGS. 41A and 41B are perspective views of a spinal implant device having a flexible chain formed by connected links, in the straightened and locked position.
Figure 41B:
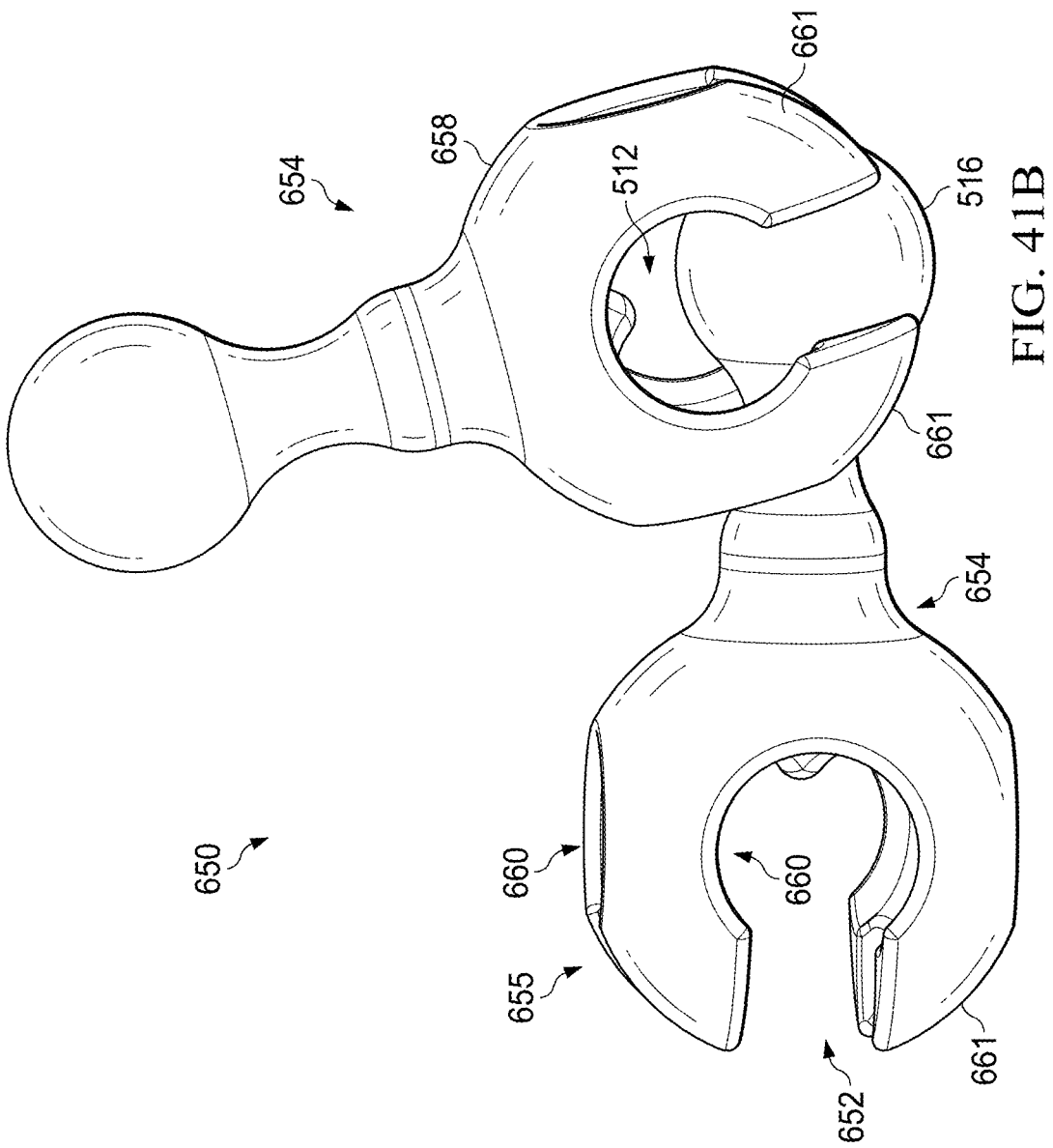

FIGS. 41A and 41B are perspective views of a spinal implant device 650 having a flexible, lockable chain 652 formed by connected links 654, in the straightened and angled position. The spinal implant device 650 and the chain 652 are substantially similar to the implant and chain 482, however, the implant device 650 and chain 652 include a lockable link 654 having a cut-out socket 656. The cutout socket 656 is substantially similar to the socket 486, however, the cutout socket 656 has a socket body 658 with multiple arced protrusions 661 and multiple slots 660 defined between the multiple arced protrusion 661. The slots 660 extend from an opening 662 to a closed end 664 and the implant 480 with the cut-out sockets in releasably angled position. In the straightened position and the angled position, the ball 516 is arranged in the recess 512 of the cutout socket 655. The ball of the connecting link rotates and pivots to move the connecting link into locked engagement with the link. The locked engagement forms due to a frictional engagement of the slot with the divot of the connecting link.

The slot extends from the opening to a closed end. The length of the slot 660 ls is greater than the socket radius Rs but less than the diameter of the socket radius (2Rs). The slot 660 includes a guide section 668 and a locking section 670. The guide section 668 extends from the opening to the locking section. The locking section extends form the guide section to the closed end of the slot 660. The locking section 670 is defined by an arced wall 672 having a diameter Dw. The guide section has a height hg and a length lg. The height hg is less than the diameter Dw. The height is greater than a divot height of the shaped body. To releasably lock a first link to a second link, the first ball arranged in the second socket, rotates the first divot into an entrance of the guide section of the slot adjacent to the opening of the socket. The first ball continues to rotate and moves the first divot through the guide section of the slot until the divot reaches the locking section. The ball then moves a small distance radially towards or away from the locking section so that a slope of the divot contacts the arced wall and forms a tight, first connection with the arced wall, thereby releasably locking the first link to the second link. The lock may be released by pressing the ball in the opposite direction used to lock the ball.

Figure 42:
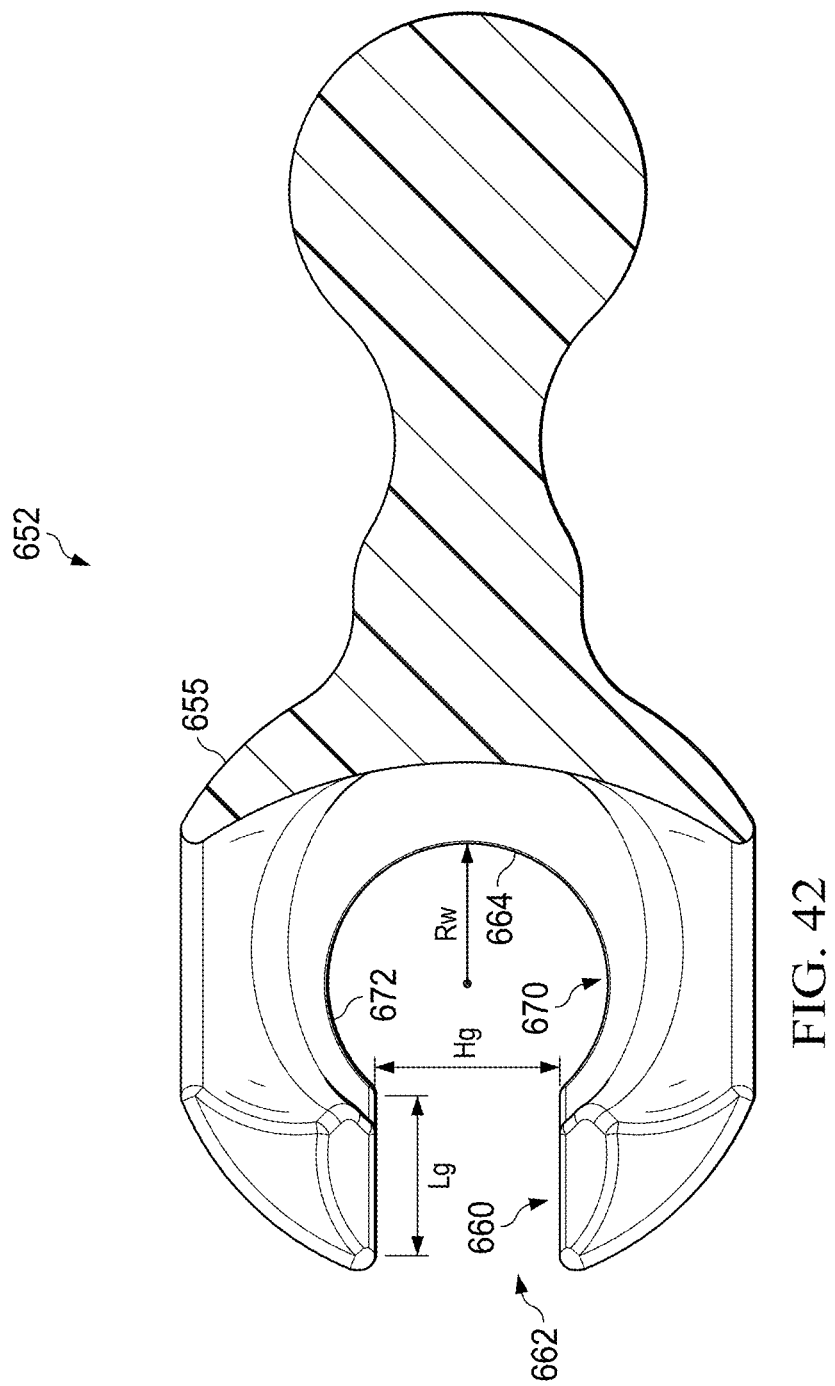
FIG. 42 is a cross-sectional side view of the lockable, flexible link.

FIG. 42 is a cross-sectional side view of the lockable, flexible link 654. The slots 660 are sized to receive the divot 520 of the shaped body 514 in the angled position. For example, in the straightened position, the shaped body of a connected link extends from the opening of the socket. In the angled position, the shaped body of the connected link extends from a slot of the socket so that the shaped body of the first link is perpendicular to the shaped body of the second link.

Figure 43:
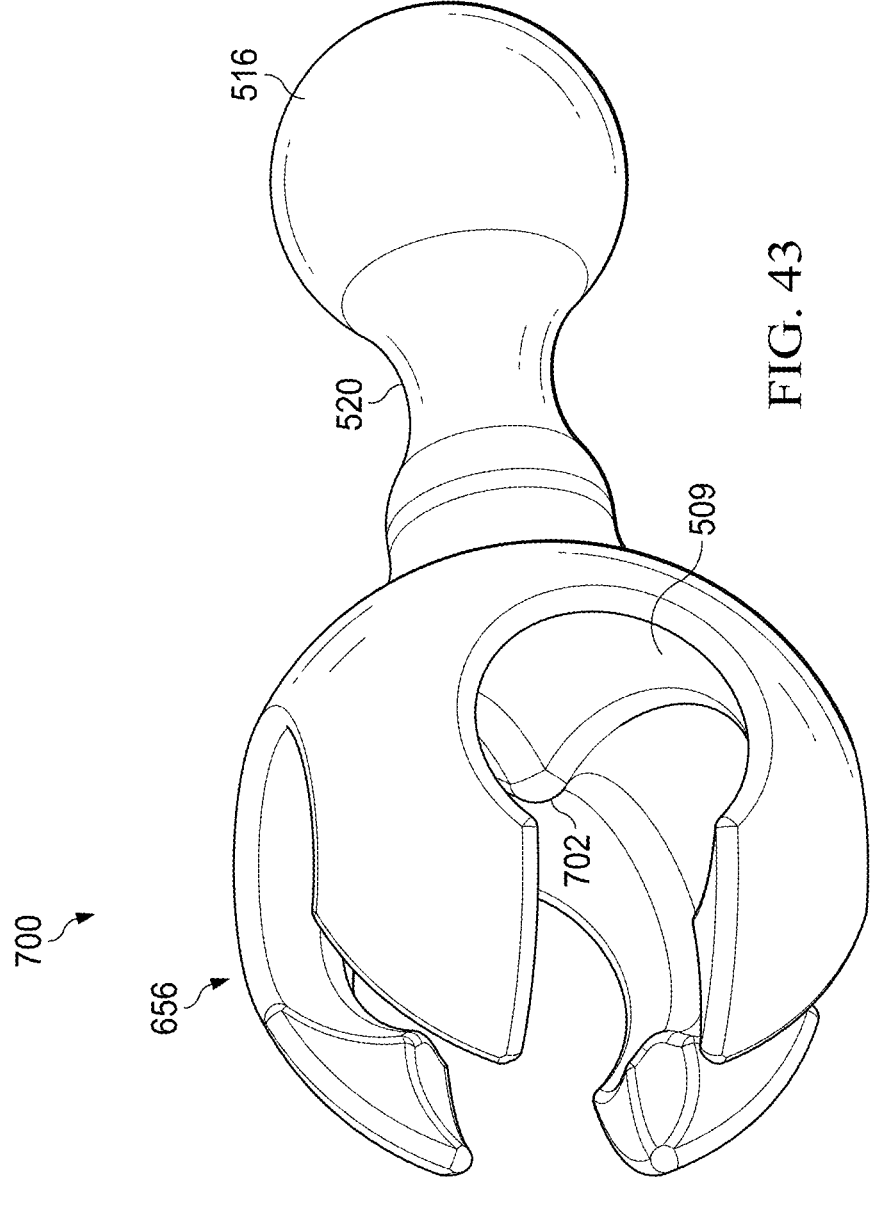
FIGS. 43 and 44 are a perspective view and a cross sectional view of a link for forming the chain having the cut-out sockets.
Figure 44:
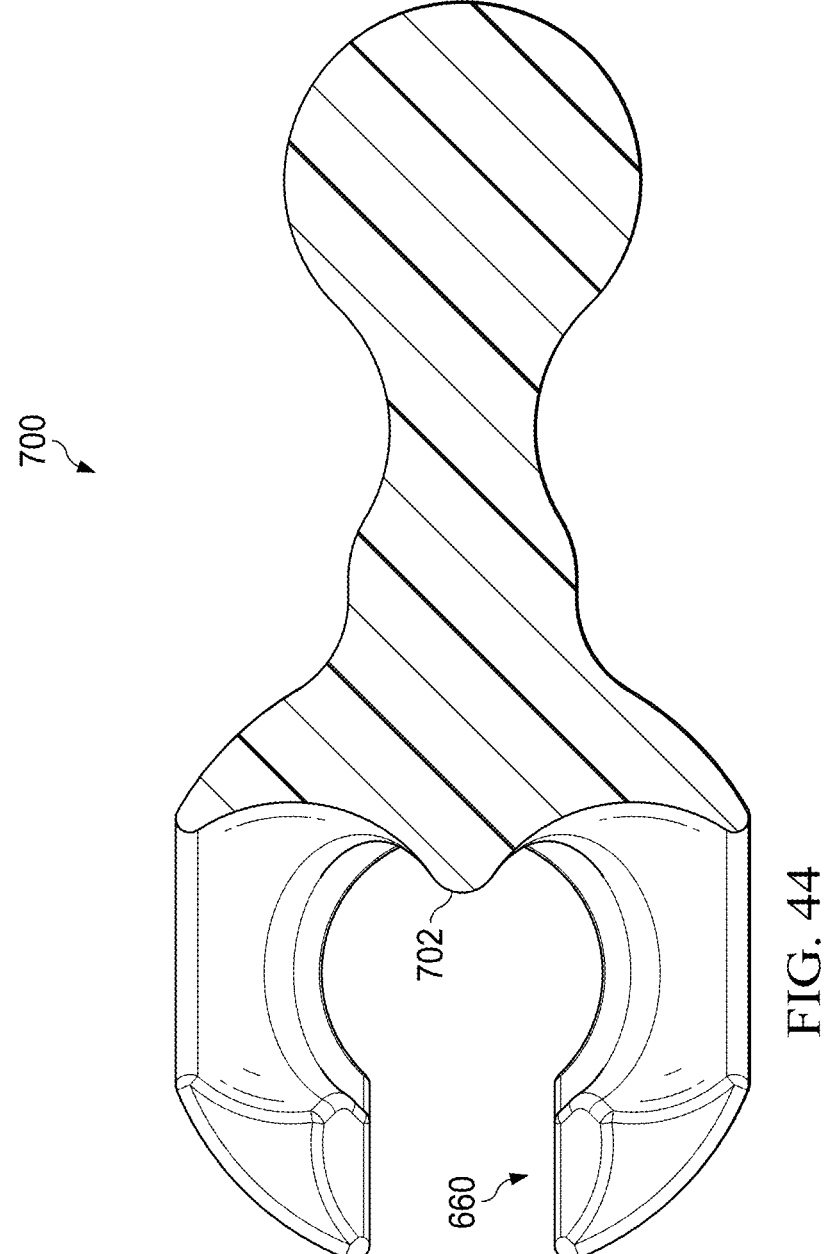

FIGS. 43 and 44 are a perspective view and a cross sectional view of a link 700 for forming the chain 602 having the cut-out sockets 656. The link 700 is substantially similar to the link 654, however the link 700 includes a protrusion or fillet 702 extending from the smooth inner surface 509. The fillet 702 contacts the ball of another link so that the ball does not rub or abut the smooth inner surface. The fillet can reduce wear on the links by stabilizing the inert location within the recess and distancing the insert location from the inner face when the insert is arranged in the recess. In addition, the fillet can reduce the risk of collapse between the connected links in the chain 602.

Figure 45:
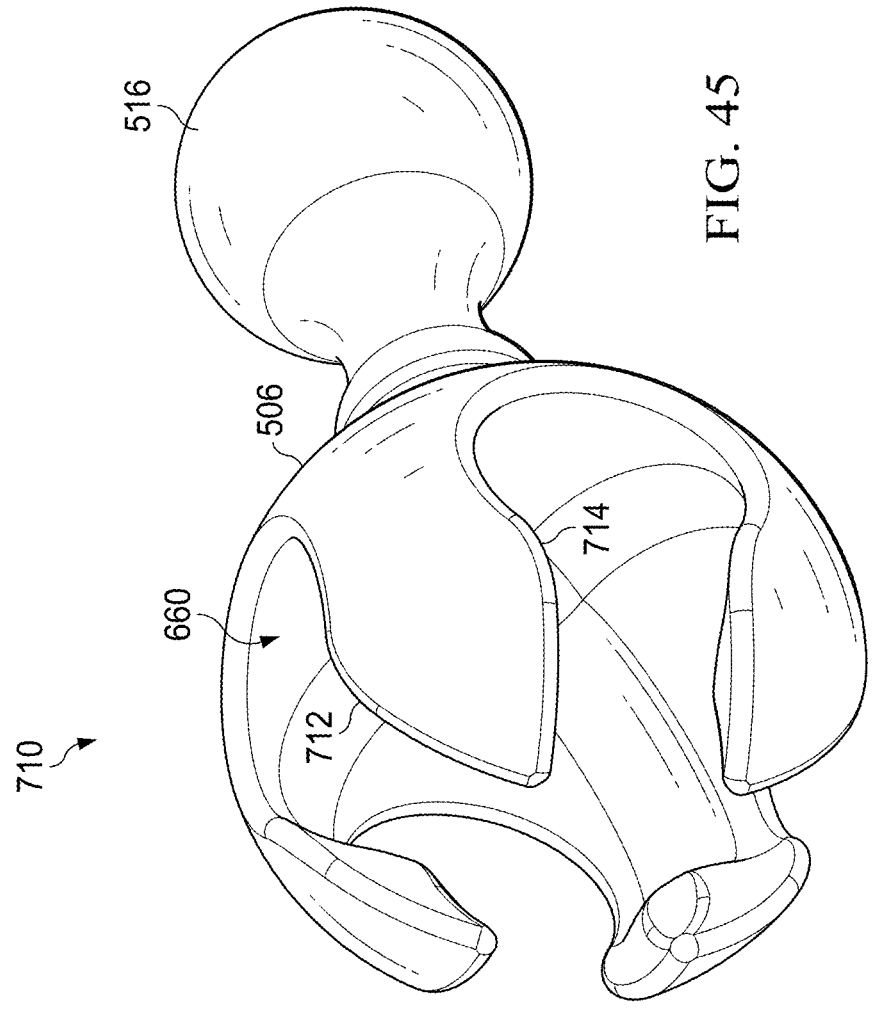
FIGS. 45 and 46 are a perspective view and a cross sectional side view of a link for forming the chain with the cut-out sockets.
Figure 46:
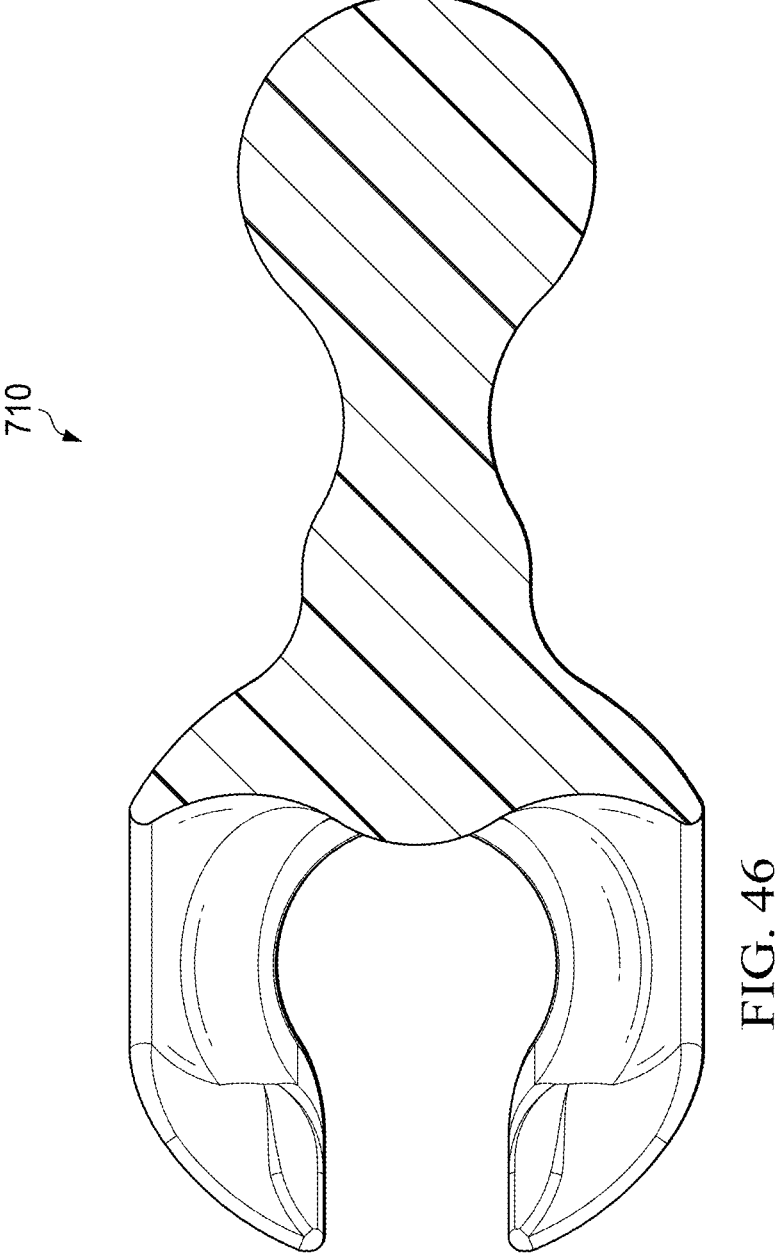

FIGS. 45 and 46 are a perspective view and a cross sectional side view of a link 710 for forming the chain 702 with the cut-out sockets 565. The link 710 is substantially similar to the link 654, however, in the link 710, the edges 712 defining the slots 660 are smooth and/or beveled rather than sharp. The slots 660 are defined by arced protrusions 714 with rounded edges 712 so that the shaped body 506 of a connecting link 700 moves smoothy from between the opening and the slots 660.

While a variety of links with various sockets, joints and attachment structures has been described as connected to similarly structured links, some chains are formed by a combination of different links disclosed herein. For example, a flexible chain may include at least one link 484, at least one lockable link 654, and/or at least one pivotable link 604, or any combination of links disclosed herein.

EXAMPLES

In some implementations, spinal implant devices include: a unitary strand extending from a first end to a second end, the unitary strand including: an exterior surface extending from the first end to the second end, and internal volume defined by the exterior, wherein the internal volume has an infill structure; a first bead formed in the strand having a first diameter, a second bead formed in the strand having a second diameter, and at least one joint formed in the strand between the first bead and the second bead, the at least one joint having a third diameter, wherein the third diameter is less than the first diameter and less than the second diameter.

In an example implementation combinable with any other example implementation, the infill structure of the internal volume is a gyroid infill structure or is a honey comb infill structure.

In an example implementation combinable with any other example implementation, the infill structure extends from the first end of the unitary strand to the second end of the unitary strand.

In an example implementation combinable with any other example implementation, the at least one joint comprises a plurality of filaments particularly wherein the filaments have a diameter of about 0.1 mm to about 2 mm.

In an example implementation combinable with any other example implementation, the plurality of filaments comprises at least four filaments. In some implementations, the plurality of filaments comprises five filaments arranged in a cross shape.

In an example implementation combinable with any other example implementation, the at least one joint is formed by PEEK or PEKK and/or the unitary strand is formed by PEEK or PEKK.

In an example implementation combinable with any other example implementation, the devices further include a set of radio-opaque markers arranged in the unitary strand. In some implementations, the set of markers includes a first marker embedded in the first bead (e.g., a tantalum sphere, a tantalum pin, omnipek, or a ligating clip). In some implementations, the devices also include a second marker embedded in the second bead (e.g., a tantalum sphere, a tantalum pin, omnipek, or a ligating clip).

In an example implementation combinable with any other example implementation, the first bead has a first modulus of elasticity, wherein the second bead has a second modulus of elasticity, and the joint has a third modulus of elasticity. In some implementations, the third modulus of elasticity is less than the first and the second modulus of elasticity and/or the first modulus of elasticity is equal to the second modulus of elasticity.

In an example implementation combinable with any other example implementation, the infill structure comprises a bead infill structure and a joint infill structure. In some implementations, the bead infill structure is different from the joint infill structure.

In an example implementation combinable with any other example implementation, the exterior surface comprises a mesh having multiple openings configured to receive new bone growth.

In some implementations, spinal implant devices include: a chain formed by multiple connected links, wherein each link is formed by an osteoconductive material, each link of the multiple links including: a socket at a first end of the link, the socket including: a socket body having a socket radius, the socket body having an outer face and a smooth inner face, an opening defined by the socket body, wherein the opening extends from the outer face to the inner face, the opening having an opening radius, and a socket recess defined by the inner face of the socket body, the recess having a recess radius, wherein the opening connects to the socket recess. A joint extending from the socket body to a second end of the link includes: a ball at the second end, the ball having a ball radius less than the socket radius and greater than the opening radius, the socket recess sized to receive a ball from another link; and a shaped body extending between the ball and socket body to connect the ball of the link and socket body of the link.

In an example implementation combinable with any other example implementation, each link of the multiple links comprises an external surface defining an internal volume, wherein the internal volume has an infill pattern (e.g., a gyroid infill pattern or a honey comb infill pattern).

In an example implementation combinable with any other example implementation, the socket radius is about 1 or about 5.

In an example implementation combinable with any other example implementation, wherein the socket radius is double the ball radius. In some implementations, the shaped body has a length and a height. In some implementations, the body height is two thirds of the socket radius.

In an example implementation combinable with any other example implementation, the multiple connected links comprise a first link having a first ball and first socket inserted into a second link having a second ball and socket, wherein the first ball is arranged in a socket recess defined by an inner face of the second socket, wherein the first ball is distanced from the inner surface by a distance. In some implementations, the distance is about 8% of the socket radius. In some implementations, the distance is about 10% of the socked radius.

In an example implementation combinable with any other example implementation, the shaped body comprises a pivot, wherein the ball is rotatable around the pivot. In some implementations, the pivot is a hinge (e.g., a living hinge). In some implementations, the shaped body has a first portion and a second portion, wherein the pivot connects first portion to the second portion. In some implementations, the pivot is formed by a flexible material. In some implementations, the pivot is a revolute joint. In some implementations, wherein the pivot is a ball joint. In some implementations, the pivot is a roller joint. In some implementations, the first portion of the shaped body of the joint extends from the socket body, and the second portion of the shaped body extends from the ball of the joint. In some implementations, the pivot is arranged in the second portion of the shaped body. In some implementations, the pivot of the joint is adjacent to the ball of the joint.

In an example implementation combinable with any other example implementation, the pivot of the joint is adjacent to the ball wherein the link comprises titanium.

In an example implementation combinable with other example implementations, the socket comprises at least three arced protrusions extending from the joint, wherein the at least three arced protrusions define the recess. In some implementations, the socket comprises at least four arced protrusions. In some implementations, the socket further comprises slots defined between the at least three arced protrusions. In some implementations, the slots are sized to receive the body of a link. In some implementations, the slots each comprises an inlet portion and a cavity portion.

In an example implementation combinable with any other example implementation, the socket comprises a protrusion arranged on a wall of the socket defining the recess, wherein the protrusion extends into the recess.

In an example implementation combinable with any other example implementation, devices also include a set of radio-opaque markers, each marker attached to a corresponding link. In some implementations, devices also include a first marker attached to a first link of the chain. In some implementations, the first marker is omnipek or a ligating clip. In some implementations, devices also include a second marker attached to a second link of the chain, the wherein a ball of the first link is arranged in a socket of the second link.

In some implementations, spinal implant devices include: a foldable chain extending from a first end to a second end, the chain including: multiple rotatably connected links formed by at least one osteoconductive material, the multiple connected links including a first link and a second link. The first link includes: a first socket at a proximal end of the first link, and a first joint extending from the first socket to a distal end of the first link, the first joint including, a first insert at the distal end, a first shaped body extending between the first insert and first socket body to connect the first insert of the first link and first socket of the first link. The second link includes: a second socket at a proximal end of the second link, and a second joint extending from the second socket to a distal end of the second link, the second joint including, a second insert at the distal end, wherein the second insert is arranged in the first socket, a second shaped body extending between the second insert and second socket body to connect the second insert of the second link and second socket of the second link, the second shaped body including a first pivot. The second insert and first pivot form a rotatable connection, wherein the chain is configured to fold at least at the rotatable connection.

In an example implementation combinable with any other example implementation, the first link comprises a first external surface defining a first internal volume, wherein the first internal volume has a first infill pattern. In some implementations, the first infill pattern is a gyroid infill pattern. In some implementations, the first infill pattern is a honeycomb infill pattern.

In an example implementation combinable with any other example implementation, the second link comprises a second external surface defining a second internal volume, wherein the second internal volume has a second infill pattern. In some implementations, the second infill pattern is a gyroid infill pattern. In some implementations, the second infill pattern is a honeycomb infill pattern.

In an example implementation combinable with any other example implementation, the first socket includes: a first socket body having a first socket radius, the first socket body having a first outer face and a smooth first inner face, a first opening defined by the first socket body, wherein the first opening extends from the first outer face to the first inner face, the first opening having a first opening radius, and a first socket recess defined by the smooth first inner face of the first socket body, the first recess having a first recess radius, wherein the first opening connects to the first socket recess. In some implementations, the first insert having a first insert radius less than the first socket radius and greater than the first opening radius. In some implementations, the first insert is a disc or a ball. In some implementations, the first socket radius is double the first insert radius. In some implementations, the second insert is distanced from the first inner surface by a distance (e.g., about 8% of the first socket radius or about 10% of the first socked radius).

In an example implementation combinable with any other example implementation, the first shaped body has a first length and a first height. In some implementations, the first body height is two thirds of the first socket radius.

In an example implementation combinable with any other example implementation, the first shaped body comprises a first pivot, wherein the first insert is rotatable around the first pivot. In some implementations, the first pivot is a hinge (e.g., a living hinge). In some implementations, the first shaped body has a proximal portion and a distal portion, wherein the pivot connects proximal portion to the distal portion. In some implementations, the proximal portion of the first shaped body of the first joint extends from the first socket body, wherein the distal portion of the first shaped body extends from the first insert of the first joint. In some implementations, the first pivot is arranged in the distal portion of the first shaped body. In some implementations, the first pivot of the joint is adjacent to the first insert of the first joint.

In an example implementation combinable with any other example implementation, the second socket includes: a second socket body having a second socket radius, the second socket body having a second outer face and a smooth second inner face, a second opening defined by the second socket body, wherein the second opening extends from the second outer face to the second inner face, the second opening having a second opening radius, and a second socket recess defined by the smooth second inner face of the second socket body, the second recess having a second recess radius, wherein the second opening connects to the second socket recess.

In some implementations, methods for manufacturing a flexible spinal implant include: extruding, by a 3D printer, a shell of a first portion of the flexible spinal implant, the shell forming an exterior surface of the implant, wherein the shell of the first portion defines a first internal volume; and infilling, by the 3D printer, the first internal volume of the first portion of the implant with a bone-like infill pattern (e.g., a honeycomb pattern or a gyroid pattern).

In an example implementation combinable with any other example implementation, the flexible spinal implant has a unitary strand extending along a first axis. In some implementations, an extruder nib of the 3D printer is oriented perpendicular to the first axis. In some implementations, the first portion extends from the first end of the implant to the second end of the implant. In some implementations, the first portion forms a first half of the implant. In some implementations, the first half the implant comprises at least two partially formed beads and at least one partially formed joint connecting the at least two partially formed beads. In some implementations, the first half of the implant comprises a first partially formed barrel, a second partially formed barrel, and a partially formed joint connecting the first partially formed barrel to the second partially formed barrel. In some implementations, the first half of the implant has an open end oriented towards the nib of the 3D printer.

In an example implementation combinable with any other example implementation, methods also include extruding a second half of the implant to form a flexible, unitary spinal implant. In some implementations, methods also include extruding a second portion of the shell of the implant, the second shell of the implant defining an interior volume, and infilling the interior volume with the bone-like infill pattern. In some implementations, methods also include extruding a plurality of layers of the second portion, each layer of the plurality of layers including a layer of the external shell and a layer of an infill pattern. In some implementations, methods also include extruding final layer of the second portion of the shell to form the second half of the implant.

In an example implementation combinable with any other example implementation, an extruder nib of the 3D printer is oriented parallel to the first axis. In some implementations, the first portion of the implant forms a first end of a unitary strand of the flexible spinal implant. In some implementations, the shell of the first portion is a series of external layers of at least one bead of the flexible spinal implant, the shell of the first portion having a closed first end centered on the first axis and an open second end centered on the first axis. In some implementations, infilling the first internal volume with the bone-like infill pattern comprises infilling the shell of the first portion along the first axis from the closed end of the external layer to the open end of the external layer. In some implementations, the infill pattern comprises a series of internal layers. In some implementations, the series of internal layers are arranged adjacent to corresponding external layers of the shell. In some implementations, methods also include closing, the open second end of the external layer to form the at least one bead. In some implementations, methods also include extruding a joint extending from the closed end of the external layer, wherein the joint is centered on the first axis. In some implementations, the joint is a set of filaments (e.g., arranged in a cross pattern). In some implementations, methods also include extruding the joint extending from the closed end of the at least one bead comprises extruding a shell of the joint and infilling the shell of the joint with a bone-like pattern. In some implementations, methods also include extruding a second portion of a shell of the implant extending from the joint. In some implementations, the second portion of the shell is a second external layer of at least one bead, the second external layer having a closed first end centered on the first axis and an open second end centered on the first axis.

In an example implementation combinable with any other example implementation, the first portion is a joint of a link of the implant, wherein the implant comprises multiple connected links.

In an example implementation combinable with any other example implementation, the first portion is a socket of a link of the implant, wherein the implant comprises multiple connected links.

In an example implementation combinable with any other example implementation, methods also include extruding a second portion of the link, wherein the second portion has a shell defining an internal volume of the second portion, wherein the internal volume of the second portion has the bone-like infill, wherein the second portion is a joint. In some implementations, the shell of the second portion forms a plurality of openings, wherein the apertures expose the bone-like infill.

In an example implementation combinable with any other example implementation, the first portion is a partially formed socket at a first end of the link and a partially formed joint at the second end of the link, wherein the first end of the link and the second end of the link define a first axis, wherein a nib of the 3D printer is oriented perpendicular to the first axis. In some implementations, the first portion is a first half of the link. In some implementations, methods also include extruding a second half of the link, wherein the second half of the link has the bone-like infill pattern.

In an example implementation combinable with any other example implementation, the shell of the first portion forms a plurality of openings, wherein the apertures expose the bone-like infill.

What is claimed is:

1. A method of treating a vertebral injury, the method comprising:
receiving a dehydrated implant comprising beads of a first diameter connected by joints of a second diameter that is less than the first diameter, the beads each comprising a core of mineralized material and a demineralized layer around the core of mineralized material, and the joints comprising demineralized material;
soaking the dehydrated implant in a biologically compatible solution for less than 10 minutes to partially rehydrate the implant, and
inserting the partially rehydrated implant into a vertebra to complete rehydration of the partially rehydrated implant.

2. The method of claim 1, wherein soaking the dehydrated implant includes soaking the dehydrated implant in the solution for at least 1 minute and for less than 10 minutes.

3. The method of claim 2, wherein soaking the dehydrated implant includes soaking the dehydrated implant in the solution to at least 2 minutes and for less than 10 minutes.

4. The method of claim 3, wherein soaking the dehydrated implant includes soaking the dehydrated implant in the solution for about 3 minutes.

5. The method according to claim 3, wherein the completely rehydrated implant has a rehydrated volume at least 20% larger than a dehydrated volume of the dehydrated implant.

6. The method according to claim 5, wherein the completely rehydrated implant has a rehydrated volume at least 40% larger than a dehydrated volume of the dehydrated implant.

7. The method of claim 1, wherein the first diameter is between about 3.2 mm and about 3.7 mm.

8. The method of claim 7, wherein the second diameter is between about 0.5 mm and about 3 mm.

9. The method of claim 8, wherein the partially rehydrated implant is more flexible than the dehydrated implant.

10. The method of claim 1, further comprising storing the dehydrated implant at room temperature.

11. The method of claim 1, wherein completing rehydration of the partially rehydrated implant comprises rehydration of the partially rehydrated implant with patient blood.

12. The method of claim 1, wherein soaking the dehydrated implant in a biologically compatible solution comprises soaking the dehydrated implant in saline or a fluid with a medicament, medicament agents, or other therapeutic agents.

13. The method of claim 1, wherein the demineralized material comprises demineralized bone.

14. The method of claim 13, wherein the core of mineralized material comprises mineralized bone.

15. The method of claim 1, wherein soaking the dehydrated implant in the biologically compatible solution for less than 10 minutes to partially rehydrate the implant increases flexibility of the implant.

16. The method of claim 15, wherein soaking the dehydrated implant in the biologically compatible solution for less than 10 minutes to partially rehydrate the implant increases flexibility of the implant to a flexibility equal to or slightly less than a flexibility of the implant in the completely rehydrated state.

17. A method of treating an injury in a bone, the method comprising:

receiving a dehydrated implant comprising beads of a first diameter connected by joints of a second diameter that is less than the first diameter, the beads each comprising a core of mineralized material and a demineralized layer around the core of mineralized material, and the joints comprising demineralized material;

soaking the dehydrated implant in a biologically compatible solution for less than 10 minutes to partially rehydrate the implant, and inserting the partially rehydrated implant into the bone to complete rehydration of the partially rehydrated implant.

18. The method of claim 17, wherein soaking the dehydrated implant includes soaking the dehydrated implant in the solution to at least 2 minutes and for less than 10 minutes.

19. The method according to claim 18, wherein the completely rehydrated implant has a rehydrated volume at least 20% larger than a dehydrated volume of the dehydrated implant.

20. The method of claim 17, wherein the first diameter is between about 3.2 mm and about 3.7 mm.

21. The method of claim 20, wherein the second diameter is between about 0.5 mm and about 3 mm.

22. The method of claim 21, wherein the partially rehydrated implant is more flexible than the dehydrated implant.

* * * * *